(12) United States Patent
Del Campo Ascarateil et al.

(10) Patent No.: US 9,388,225 B2
(45) Date of Patent: *Jul. 12, 2016

(54) MODIFIED COILED COIL TYPE PROTEINS HAVING IMPROVED PROPERTIES

(71) Applicant: Imaxio, Paris (FR)

(72) Inventors: Judith Del Campo Ascarateil, Taverny (FR); Imene Turki Hani, Lyons (FR); Fergal Hill, Lyons (FR)

(73) Assignee: Imaxio (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/570,133

(22) Filed: Dec. 15, 2014

(65) Prior Publication Data

US 2015/0093406 A1    Apr. 2, 2015

Related U.S. Application Data

(63) Continuation of application No. PCT/EP2013/076289, filed on Dec. 11, 2013.

(60) Provisional application No. 61/802,836, filed on Mar. 18, 2013.

(30) Foreign Application Priority Data

Dec. 11, 2012  (EP) .................... 12306560

(51) Int. Cl.

| | |
|---|---|
| *A61K 39/00* | (2006.01) |
| *C07K 14/47* | (2006.01) |
| *A61K 39/002* | (2006.01) |
| *A61K 39/04* | (2006.01) |
| *A61K 39/085* | (2006.01) |
| *A61K 39/12* | (2006.01) |
| *A61K 39/385* | (2006.01) |
| *C07K 7/06* | (2006.01) |
| *C07K 14/005* | (2006.01) |
| *C07K 14/31* | (2006.01) |
| *C12N 7/00* | (2006.01) |

(52) U.S. Cl.
CPC ........... *C07K 14/4703* (2013.01); *A61K 39/002* (2013.01); *A61K 39/0005* (2013.01); *A61K 39/0006* (2013.01); *A61K 39/04* (2013.01); *A61K 39/085* (2013.01); *A61K 39/12* (2013.01); *A61K 39/385* (2013.01); *C07K 7/06* (2013.01); *C07K 14/005* (2013.01); *C07K 14/31* (2013.01); *C12N 7/00* (2013.01); *A61K 39/00* (2013.01); *A61K 2039/53* (2013.01); *A61K 2039/55561* (2013.01); *A61K 2039/55566* (2013.01); *A61K 2039/57* (2013.01); *A61K 2039/6031* (2013.01); *A61K 2039/627* (2013.01); *A61K 2039/64* (2013.01); *C07K 2319/00* (2013.01); *C07K 2319/40* (2013.01); *C07K 2319/73* (2013.01); *C12N 2760/16034* (2013.01); *C12N 2760/16134* (2013.01)

(58) Field of Classification Search
None
See application file for complete search history.

(56) References Cited

U.S. PATENT DOCUMENTS

| | | | | |
|---|---|---|---|---|
| 7,270,821 B2 * | 9/2007 | Gehin et al. | ............... | 424/192.1 |
| 7,270,921 B2 * | 9/2007 | Ogasawara | .................... | 430/30 |
| 7,928,185 B2 * | 4/2011 | Mattsby-Baltzer et al. | .. | 530/300 |

OTHER PUBLICATIONS

Birnbaum et al., Journal of Virology, 1990, 53:3319-3330.*
Swanson et al., PNAS USA, 2011, 108(23):9619-9624.*
Anderson et al., Future Microbiol., 2010, 5(4):585-602.*
Vogel, Maren, et al. "Quaternary Structure is Critical for Protein Display on Capsid-Like Particles (CLPs): Efficient Generation of Hepatitis B Virus CLPs Presenting Monomeric but not Dimeric and Tetrameric Fluorescent Proteins" PROTEINS: Structure, Function, and Bioinformatics 58:478-488 (2005) Wiley-Liss, Inc.

* cited by examiner

*Primary Examiner* — Stacy B Chen
(74) *Attorney, Agent, or Firm* — Banner & Witcoff, Ltd.

(57) ABSTRACT

The present application is related to a modified protein comprising a protein having a coiled coil domain and a peptide having the sequence such as shown in SEQ ID NO 1: ZXBBBBZ that is linked to the coiled coil domain wherein:
  Z is any amino acid or is absent;
  X is any amino acid;
  B is an arginine (R) or a lysine (K).
Said modified protein is in particular an antigen or a carrier protein, associated to an antigen. This modified protein has an increased affinity for negatively charged polymers such as nucleic acids or heparin, and shows an increased immunogenicity.

16 Claims, 16 Drawing Sheets

MODIFIED COILED COIL TYPE PROTEINS HAVING IMPROVED PROPERTIES

RELATED APPLICATION DATA

This application is a continuation of PCT application PCT/EP2013/076289 designating the United States and filed Dec. 11, 2013; which claims U.S. Provisional Application No. 61/802,836, filed on Mar. 18, 2013; which claims the benefit of EP application number 12306560.9 and filed Dec. 11, 2012 each of which are hereby incorporated by reference in their entireties.

The present invention is related to recombinant antigens containing coiled coil domains or to antigens fused to proteins containing coiled coils, wherein the coiled coils are modified. The modification improves the immunogenicity of the said antigens. Simultaneously, it improves their capacities to bind to negatively charged polymers such as nucleic acids including DNA and RNA, and to heparin.

BACKGROUND

A coiled coil is a structural motif in proteins, in which alpha-helices are coiled together like the strands of a rope. Coiled coil domains are abundant in natural proteins (1, 2), and they may be the commonest method in nature of oligomerising proteins. Coiled-coils consist of two or more alpha-helices winding around each other in a supercoil, a simple yet versatile protein fold (3). A typical coiled-coil primary sequence is repetitive, made of seven-residue repeats called a 'heptad'.

Many coiled coil type proteins are involved in important biological functions. Of particular interest herein, are those found in antigens or in carrier proteins.

Examples of coiled coils found in antigens include, but are not limited to:
  i) the dimeric coiled coils found in the OCA family (where OCA means oligomeric coiled coil adhesion): examples are NadA, a *Neisseria meningitidis* protective antigen (4); YadA from *Yersinia enterocolitica* (5); UspA2 from *Moraxella catarrhalis* (6); BadA from *Bartonella henselae* (7) and HadA from *Haemophilus influenzae* (8).
  ii) the trimeric coiled coils found in, amongst others, the influenza hemagglutinin HA2 protein (9), the F glycoprotein of Respiratory Syncytial virus (10), the gp41 glycoproteins of HIV-1 (11) and HIV-2 (12), and gp1,2 of Ebolavirus (13).
  iii) the tetrameric coiled coils found in the Newcastle Disease FIN (hemagglutinin-neuraminidase) glycoprotein and other paramyxoviruses (14, and references therein).

Carrier proteins are in particular used to improve the immunogenicity of antigens. Carrier proteins containing coiled coils have been described previously, notably a pentamer derived from COMP (15) and an artificial sequence which also forms pentamers (34), and heptamers derived from mammalian C4bp oligomerisation domains, such as the murine domain IMX108 (16), or avian C4bp oligomerisation domains (16, WO 2005/077976 and WO 2007/062819). A hybrid avian oligomerisation domain called IMX313 (WO 2007/062819) is used as an example here.

PRIOR ART

In the prior art, coiled coils have been the subject of extensive investigations to understand what determines their oligomerisation states and the relevant orientation (parallel or anti-parallel) of their helices (35). But studies to improve the immunogenicity of antigens by modifying their coiled coils have been lacking Two noteworthy examples in the prior art concern groups associated within the vaccine industry who needed to purify two separate antigens containing coiled coils with a view to vaccination (10, 36, 37); neither group modified the coiled coils in the antigen.

In the prior art, some specific peptides have been shown to improve the binding properties of monomeric proteins, which lack coiled coils. It has been shown that when a polyarginine tail is fused to recombinant proteins, they are easier to purify by ion-exchange chromatography (17, 18). In previous uses, the additional arginines were removed after purification by enzymatic means (17, 18) or alternatively left in place and used for enzyme immobilization and/or refolding (19, 20). A peptide as short as six consecutive arginines was used to immobilize a monomeric enzyme on a heparin-Sepharose column, preventing the aggregation of monomers by matrix binding and enabling the re-use of the enzyme (19, 20). Fuchs and Raines have shown that a polyarginine tag of nine amino acids can be used to immobilize a monomeric enzyme (RNase A) on a variety of supports such as glass and silica resin (22).

Other nucleic acid binding peptides have been disclosed, such as the motif SPKK which was identified in the 1980s as a DNA binding motif, and peptides containing the motif SPKK can bind double-stranded DNA (21). However, binding to RNA or to single-stranded DNA was not demonstrated, and Suzuki's data strongly suggest that binding to single-stranded DNA would not occur, as the minor groove only exists in double helical molecules.

Other peptides that have been shown to bind DNA include the protamine like domain of the Hepatitis B core antigen (38) which contains the peptide sequence SPRRRS, used in some of the examples herein.

However polyarginine tails are very susceptible to cleavage by proteases, especially serine proteases, and they have been replaced in routine use by polyhistidine tags, both for purification and immobilization purposes (45).

Separately in the prior art peptides have been fused to monomeric proteins to improve their immunogenicity. Shibagaki and colleagues have shown that protein transduction domains (PTDs) can be used to improve the transduction of dendritic cells (DCs) in vitro, and that when the transduced DCs are re-injected into the animals, improved immunogenicity of the antigen is obtained (43). Furthermore, Shimada and colleagues have shown that polyarginine peptides can improve the immunogenicity of a protein, ovalbumin, to which it is fused (42), either when injected directly into a tumour expressing the protein or when injected intradermally (41).

Most purified antigens are weakly immunogenic. Adjuvants have been used for increasing their immunogenicity. The use of a small domain, containing a coiled coil, of C4bp proteins to increase the immunogenicity of antigens has been demonstrated previously:

WO 2007/062819 describes complexes comprising as first component an avian C4bp domain and as second component an antigen, said components being in the form of a fusion protein or being non-covalently associated. This complex shows an increased immunogenicity of the antigen when administered to an organism.

WO 2011/045612 describes a fusion protein containing a fragment of the C4bp protein from the chicken, and the mycobacterial antigen 85A. Said hybrid protein improves 85A immunogenicity, not only in animals such as rodents, but also in primates.

Besides, to improve methods of immunization, it is also of great importance to induce signaling through TLR receptors, but it is at least as important to be able to limit this signaling. Toll-like receptors (TLRs) are a class of proteins that play a key role in the innate immune system. Once microbes have breached physical barriers of organisms, they are recognized by TLRs. The recognized features from microbes include double-stranded RNA of viruses, unmethylated CpG sites of bacterial and viral DNA, and certain other RNA and DNA molecules.

There is substantial interest in such nucleic acids as they are ligands for a class of Toll-Like Receptors (hereafter TLRs), and notably for TLR3, TLR7, TLR8, TLR9 and TLR13 (23 and references therein). These are sometimes classed as the "Intracellular Toll-like Receptors", but at least TLR3 is also present on some cell surfaces (24). TLR7 and TLR9 are localized in intracellular compartments (notably the endoplasmic reticulum and endosomes) and it has been shown clearly for TLR9 and TLR7 that cleavage of the receptor is necessary for activation of MyD88, through which the receptors' ligands signal (25, 26). As this cleavage occurs only in endolysosomes, it is possibly an evolutionary adaptation to prevent inappropriate signaling from self-nucleic acids.

TLR3 is expressed by a variety of epithelial cells including airway, uterine, corneal, vaginal, cervical, biliary and intestinal epithelial cell, and these cells appear to express TLR3 on their cell surfaces (24). It is perhaps not surprising, therefore, that the administration of poly I:C has been associated with a number of adverse effects (26). In that study, repeated administration at doses of 3 milligrams per gram was used. If the average mouse weighs nearly 35 g, a dose of 100 mg administered repeatedly can induce these effects. We needed only 2.5 µg of poly I:C per dose in the immunizations described here.

The importance of limiting signaling through these receptors, and notably the TLR3 receptor, is dose-dependent. An advantage of binding nucleic ligands tightly to the antigen is thus essential. Tightly bound intracellular TLR ligands are therefore highly preferred over formulations in which binding is less tight. Therefore, the man skilled in the art is looking for antigenic compositions able to bind efficiently TLR ligands, so that they are not separated from the antigen before the antigen arrives in the cells where it will trigger an immune response, with the goal of diminishing the potential adverse effects mediated by the binding of the ligands to TLR receptors elsewhere.

DESCRIPTION OF THE INVENTION

The invention is related to proteins comprising coiled coil domains that are modified by the linkage of a positively charged peptide to the coiled coil domain. The modified coiled coil type proteins have improved immunogenicity and simultaneously improved binding properties for negatively charged polymers such as heparin and nucleic acids. All the coiled coil proteins are recombinant, and the modification is obtained by fusing short peptide sequences to the termini of the coiled coils. In the examples herein the modification is carried out by genetic engineering techniques, but other methods of obtaining the modified coiled coils exist, such as peptide synthesis.

This positively charged peptide comprises preferentially arginines, but can also comprise instead lysines, or a combination of both. This peptide is short, comprising seven amino acids or less, particularly 5, 6 or 7 amino acids. One or more peptides may be used for each strand of the coiled coil.

Linkage is made directly to the coiled coil domain or through a linker peptide comprising one or more amino acids which does not affect the technical effects of the coiled coil domain, the positively charged peptide and their combination. Linkers may contain any amino acids, but preferred linkers contain glycine, serine or proline, or combinations thereof.

In one set of examples, the modified protein is the carrier protein IMX313, derived from the C4bp proteins of chicken.

The invention is also related to a fusion protein comprising a modified coiled-coil carrier protein fused to an antigen.

The invention is also related to a modified antigen comprising a modified coiled-coil domain.

The invention is also related to an immunogenic composition comprising the modified fusion protein or a modified antigen, and nucleic acid ligands for intracellular TLRs.

The invention is also related to a support carrying the modified protein of the invention, the link to the support being formed through the peptide linked to the coiled coil domain. The support heparin can be used in vitro or in vivo. Methods for using heparin to improve the immunogenicity of positively charged proteins are well known (47, and references therein).

The present application is also related to use of a modified antigen or of a modified fusion protein or an immunogenic composition such as described above, to induce an immune response in a patient.

A modified coiled coil type protein according to the present application, wherein the positively charged peptide is linked to the coiled coil domain of the modified protein, presents advantages in comparison with the corresponding non-modified protein, and notably:
  a better binding to negatively charged chromatography
    columns such as the cationic ion exchange column SP
    FF and especially to Heparin-Sepharose columns;
  a better binding to nucleic acids;
  in the case of carrier proteins and antigens, an increased
    immunogenicity of the antigens that are these modified
    coiled coil type proteins, or of the antigens associated
    with said modified carrier proteins.

DETAILED DESCRIPTION OF THE INVENTION

Before describing the present invention in detail, it is to be understood that this invention is not limited to particularly exemplified methods and may, of course, vary. In particular, the present invention is related to modified antigens possessing coiled coil domains, and not limited to specific carrier proteins or to specific antigens containing coiled coils.

All publications, patents and patent applications cited herein, whether supra or infra, are hereby incorporated by reference in their entirety. However, publications mentioned herein are cited for the purpose of describing and disclosing the protocols, reagents and vectors that are reported in the publications and that might be used in connection with the invention.

Furthermore, the practice of the present invention employs, unless otherwise indicated, conventional protein purification and molecular biological techniques within the skill of the art. Such techniques are well known to the skilled worker, and are explained fully in the literature. In the claims that follow and in the consecutive description of the invention, except where the context requires otherwise due to express language or necessary implication, the word "comprise", "contain", "involve" or "include" or variations such as "comprises", "comprising", "containing", "involved", "includes", "including" are used in an inclusive sense, i.e. to specify the presence of the stated features but not to preclude the presence or addition of further features in various embodiments of the invention.

The following terms are defined for a better understanding of the invention:

A "coiled coil type protein" also referenced as "coiled-coil containing protein" or "protein having a coiled coil domain" designates a protein comprising a coiled coil motif, i.e. at least two alpha-helical strands winding around each other in a supercoil. Several proteins containing such coiled coils have been reported in the literature. According to the invention, the preferred coiled-coil type proteins are antigens and carrier proteins.

A "carrier protein" designates generally a protein to which antigens are conjugated or fused and thereby the antigens are rendered more immunogenic. Here the term is used specifically in the meaning of a protein carrying an antigen. The function of the protein is to increase the immunogenicity of said antigen to which it is conjugated or fused. Fusion has the advantage of creating a homogenous product. More formally, the "conjugation" can be described as genetic: the DNA encoding the pro-immunogenic tag or carrier protein is spliced to the DNA encoding the antigen. With traditional, chemical conjugation methods, one is not always able to control precisely at which positions the antigen is joined to the protein. In this form, this subclass of carrier proteins is also called "pro-immunogenic tags" or even "adjuvant" (16) or "genetic adjuvant".

According to the invention, a "modified protein" designates a protein having a modified sequence compared to the wild-type sequence, with the addition or partial substitution of a positively charged peptide according to the invention. The difference between the unmodified protein and the modified protein of the invention lies in the positively charged peptide linked to the coiled coil domain, either added or partially substituted. It is understood by the skilled person that the modified protein of the invention is a recombinant protein, or a chimera not found in nature. Natural proteins comprising a coiled coil domain and a charged peptide domain modified elsewhere but not in the charged peptide domain are not part of the present invention.

The invention is related to a modified protein comprising (i) a protein having a coiled coil domain and (ii) at least one positively charged peptide linked to the coiled coil domain, the positively charged peptide having the sequence ZXBBBBZ (SEQ ID NO 1), wherein:

Z is any amino acid or is absent;
X is any amino acid;
B is an arginine (R) or a lysine (K).

The last amino acid of the peptide may be neither an arginine nor a lysine residue when it is desired to protect the peptide against destruction by exoproteases such as carboxypeptidase B.

When the modified protein of the invention comprises more than one positively charged peptide of SEQ ID NO1, the peptides are preferably fused together to form one single positively charged peptide being a repetition of SEQ ID NO1 of formula (ZXBBBBZ)n wherein n is an integer of 1 or more, up to at least 6, particularly 1, 2, 3, 4, 5 or 6, preferably 2.

In another embodiment, the 2, 3, 4, 5 or 6 peptides may be separated by one of more linkers as defined below.

In a preferred embodiment of the invention, the peptide has a sequence selected from the group consisting of the sequences SPRRRRS (SEQ ID NO 2), GRRRRR (SEQ ID NO 3), SPKKKK (SEQ ID NO 4), GKKKK (SEQ ID NO 5) and GRRRRRS (SEQ ID NO 36) particularly for heptameric coiled coils. Particularly for trimeric coiled coils, a fusion of two positively charged peptides is preferred, more preferably with a sequence selected from the group consisting of the sequences SPRRRRRRRRRS (SEQ ID NO 37), a combination of a first peptide SPRRRR (SEQ ID NO 38) with a second peptide RRRRRS (SEQ ID NO 39) and GRRRRRRRRRS (SEQ ID NO 40), a combination of a first peptide GRRRRR (SEQ ID NO 41) with the peptide RRRRRS (SEQ ID NO 39).

The peptide may be fused to the coiled coil at the C-terminus, or at the N-terminus. The fusion of the peptide to the protein can be performed with a linker, a short peptidic sequence linking the peptide and the protein, or without. Linkers may contain any amino acids, but preferred linkers contain glycine, serine or proline, or combinations thereof.

In a particular embodiment, a few amino acids of the C-terminus of the protein can be deleted, and replaced with one or more copies of the peptide ZXBBBBZ.

In a preferred aspect of the invention, the peptide is linked to the coiled coil at its C-terminal extremity.

In an aspect of the invention, the modified protein has a function of carrier protein, in particular acts as a carrier for antigens.

In a preferred aspect of the invention, the modified protein is the chicken-derived carrier C4-binding protein called IMX313, comprising a heptameric coiled coil, described in the patent application WO 2007/062819.

A specific modified protein according to the invention is the protein IMX313 wherein the peptide GRRRR (SEQ ID NO 3) is linked to the coiled-coil domain of IMX313.

Another specific modified protein according to the invention is the protein IMX313 wherein the peptide SPKKKK (SEQ ID NO 4) is linked to the coiled-coil domain of IMX313.

Another specific modified protein according to the invention is the protein IMX313 wherein the peptide GKKKK (SEQ ID NO 5) is linked to the coiled-coil domain of IMX313.

A preferred specific modified protein according to the invention is the protein IMX313 wherein the peptide SPRRRRS (SEQ ID NO 2) is linked to the coiled-coil domain of IMX313.

The amino acid sequences of IMX313, IMX313T and IMX313P are shown below (the * represents the STOP codon):

```
IMX313
                                            (SEQ ID NO 6)
KKQGDADVCGEVAYIQSVVSDCHVPTAELRTLLEIRKLFLEIQKL
KVELQGLSKE*

IMX313T
                                            (SEQ ID NO 7)
KKQGDADVCGEVAYIQSVVSDCHVPTAELRTLLEIRKLFLEIQKL
KVELQSPRRRRS*

IMX313P
                                           (SEQ ID NO 42)
KKQGDADVCGEVAYIQSVVSDCHVPTAELRTLLEIRKLFLEIQKL
KVEGRRRRRS*.
```

In a preferred embodiment, the protein having function of a carrier protein is IMX313P (SEQ ID NO 42). A protein comprising the sequence of IMX313P (SEQ ID NO 42) is also per se an object of the present invention, alone or fused with one or more positively charged peptide and an antigen or another protein.

In a most preferred embodiment, the coiled coil domain of IMX313P (SEQ ID NO 42) is linked to a fusion of 2 positively charged peptides of SEQ ID NO 1, more preferably the peptide of sequence SPRRRRRRRRRS (SEQ ID NO 37), or the peptide of sequence GRRRRRRRRRRS (SEQ ID NO 40).

In another aspect of the invention, the modified protein is not a carrier protein, but is an antigen. Said oligomeric antigen is in particular selected from the group consisting of:
- the influenza hemagglutinin HA protein,
- the F glycoprotein of Respiratory Syncytial virus,
- the gp41 glycoprotein of HIV-1,
- the gp41 glycoprotein of HIV-2,
- gp1,2 of Ebolavirus,
- NadA from *Neisseria meningitidis,*
- YadA from *Yersinia enterocolitica,*
- UspA2 from *Moraxella catarrhalis,*
- BadA from *Bartonella henselae* and
- HadA from *Haemophilus influenza.*

The invention is also related to an association between a modified carrier protein and an antigen. Such association of a carrier protein (IMX313) and an antigen has already been shown to increase the immunogenicity of said antigen (see patent application WO 2007/062819). With a modified carrier protein, the increase of immunogenicity is even better than with the unmodified IMX313 protein.

In particular, the modified carrier protein associated with an antigen is IMX313P having the sequence SEQ ID NO 42.

In one alternative, the two associated components are non-covalently associated with each other.

In a preferred alternative, the two associated components are coupled chemically, and are in the form of a fusion protein. The man skilled in the art knows how to connect two peptidic components, in the aim of producing a fusion protein.

The invention is in particular related to a fusion protein comprising a carrier protein with a modified coiled coil and one or more antigens.

In a preferred aspect of the invention, one of the following antigens is fused to the IMX313T or IMX313P modified protein:
  i) the *Staphylococcus aureus* Protein A protein, mutated as described (27, 44), or the *Staphylococcus aureus* protein hemolysin alpha, or *Staphylococcus aureus* protein ClfB or *Staphylococcus aureus* protein Sortase A;
  ii) 85A, a protein secreted by *Mycobacterium tuberculosis* (28);
  iii) the self-antigen GnRH;
  iv) the cryptosporidial antigen Cp15;
  v) the influenza nucleoprotein.

A specific fusion protein according to the invention is the protein IMX313P (SEQ ID NO 42) wherein the peptide GRRRRRS (SEQ ID NO 36) is linked to the coiled-coil domain of IMX313, and the modified protein is fused with the *Staphylococcus aureus* Protein A protein.

Another specific fusion protein according to the invention is the protein IMX313P (SEQ ID NO 42) wherein the peptide GRRRRRS (SEQ ID NO 36) is linked to the coiled-coil domain of IMX313, and the modified protein is fused with the protein 85A.

Another specific fusion protein according to the invention is the protein IMX313 (SEQ ID NO 6) wherein the peptide SPKKKK (SEQ ID NO 4) is linked to the coiled-coil domain of IMX313, and the modified protein is fused with the *Staphylococcus aureus* Protein A protein.

Another specific fusion protein according to the invention is the protein IMX313 (SEQ ID NO 6) wherein the peptide SPKKKK (SEQ ID NO 4) is linked to the coiled-coil domain of IMX313, and the modified protein is fused with the protein 85A.

Another specific fusion protein according to the invention is the protein IMX313 (SEQ ID NO 6) wherein the peptide GKKKK (SEQ ID NO 5) is linked to the coiled-coil domain of IMX313, and the modified protein is fused with the *Staphylococcus aureus* Protein A protein.

Another specific fusion protein according to the invention is the protein IMX313 (SEQ ID NO 6) wherein the peptide GKKKK (SEQ ID NO 5) is linked to the coiled-coil domain of IMX313, and the modified protein is fused with the protein 85A.

Another specific fusion protein according to the invention is the protein IMX108T (SEQ ID NO 64) wherein the peptide SPRRRRS (SEQ ID NO 2) is fused to the coiled coil domain of the protein IMX108 (SEQ ID NO 63).

A preferred specific modified protein according to the invention is the protein IMX313 (SEQ ID NO 6) wherein the peptide SPRRRRS (SEQ ID NO 2) is linked to the coiled-coil domain of IMX313, and the modified protein is fused with the *Staphylococcus aureus* Protein A protein.

Another preferred specific modified protein according to the invention is the protein IMX313 (SEQ ID NO 6) wherein the peptide SPRRRRS (SEQ ID NO 2) is linked to the coiled-coil domain of IMX313, and the modified protein is fused with the protein 85A.

As shown in the examples, these two model antigens were used to demonstrate that the modification of coiled coils improved their immunogenicity. Both B and T cell responses were improved. Furthermore, the modified coiled coils were more immunogenic when administered either as proteins or as nucleic acids.

The invention is also related to an immunogenic composition comprising a modified coiled coil type protein such as described above, or a fusion protein such as described above, and nucleic acid ligands for intracellular TLRs. These nucleic acid ligands for TLRs are preferentially complexed with a modified carrier protein. Advantageously, the nucleic acid ligands are bound to the modified protein, although the corresponding unmodified carrier protein was unable to bind significantly these nucleic acid ligands for TLRs.

The invention is also related to an immunogenic composition comprising a modified coiled coil type protein such as described above, or a fusion protein such as described above, and heparin. Heparin is preferentially complexed with a modified carrier protein. Advantageously, heparin is bound to the modified protein, although the corresponding unmodified carrier protein was unable to bind significantly to heparin.

The invention is also related to a solid support carrying a modified protein, wherein said protein is bound to the support with the peptide ZXBBBBZ. Indeed, the abundance of charges in the peptide is sufficient to bind strongly the modified protein to the surface.

The invention is also related to a method for increasing the binding capacities to a support of a protein comprising a coiled coil domain, comprising the linking of at least one peptide ZXBBBBZ to the coiled coil domain, wherein:
  Z is any amino acid, or is absent,
  X is any amino acid;
  B is an arginine (R) or a lysine (K).

In particular, the support is a chromatography column. All soluble modified coiled coils proteins can be bound to such columns, using the positively charged peptide as an affinity tag. The operator can modify the number of arginine residues in the peptide of general sequence ZXBBBBZ to strengthen or diminish the binding. Alternatively the operator can modify the number of peptides of the general sequence ZXBBBBZ to strengthen the binding. The smaller the number of protein chains in the oligomer, the larger the number of arginines in the peptide or peptides that should be used. Thus, for example, with a trimeric coiled coil, nine or more arginines per chain should preferably be used to ensure similar purification on heparin-sepharose.

The invention is also related to a method for increasing the immunogenicity of a carrier protein or of an antigen comprising a coiled coil domain, comprising the linking of at least one peptide ZXBBBBZ to the coiled coil domain of said protein wherein:

Z is any amino acid, or is absent,

X is any amino acid;

B is an arginine (R) or a lysine (K).

The invention is also related to a method for increasing the immunogenicity of an antigen comprising:

preparing a modified carrier protein such as described above; and associating said antigen to said modified carrier protein and to nucleic acid ligands for intracellular TLRs or heparin.

The invention is in particular related to a method for increasing the Th1 immunogenicity of an antigen, characterized by a very high IgG2a to IgG1 ratios such as exemplified below, comprising:

preparing a modified carrier protein such as described above; and associating said antigen to said modified carrier protein and to nucleic acid ligands for intracellular TLRs or heparin.

The invention is also related to a modified antigen according to the invention, or of a fusion protein according to the invention, for its use as a vaccine.

The present application is also related to a method for inducing an immune response in a patient in need, comprising the administration to the patient of a vaccine composition comprising a fusion protein comprising a modified carrier protein and an antigen.

The present application is also related to a method for inducing an immune response in a patient in need, comprising the administration to the patient of a vaccine composition comprising an immunogenic composition comprising a modified protein and nucleic acid ligands for intracellular TLRs or heparin.

The invention is also related to the nucleic acid molecules encoding the modified proteins and fusion proteins such as described above.

Moreover, the present invention concerns a vaccine composition comprising at least one nucleic acid molecule such as described above. Vaccine compositions comprising nucleic acids molecules are well known by the man skilled in the art, and are in particular described in the patent application WO2008/122817, hereby incorporated by reference.

Such nucleic acids can be used per se, or they can be administered in viral vectors which are also described in the patent application WO2008/122817. Some viral vectors have been modified to produce nucleic acids which could then bind to the modified antigens which are encoded in viral vectors. Modification of viral vectors to produce nucleic acids is disclosed in WO2007/100908, hereby incorporated by reference.

The present invention is also related to a method for purifying a modified coiled-coil type proteins such as described above, comprising the following successive steps:

loading a heparin-sepharose chromatography column with the modified protein, and eluting said protein with a salt concentration superior to 500 mM.

EXAMPLES

Figure 1:
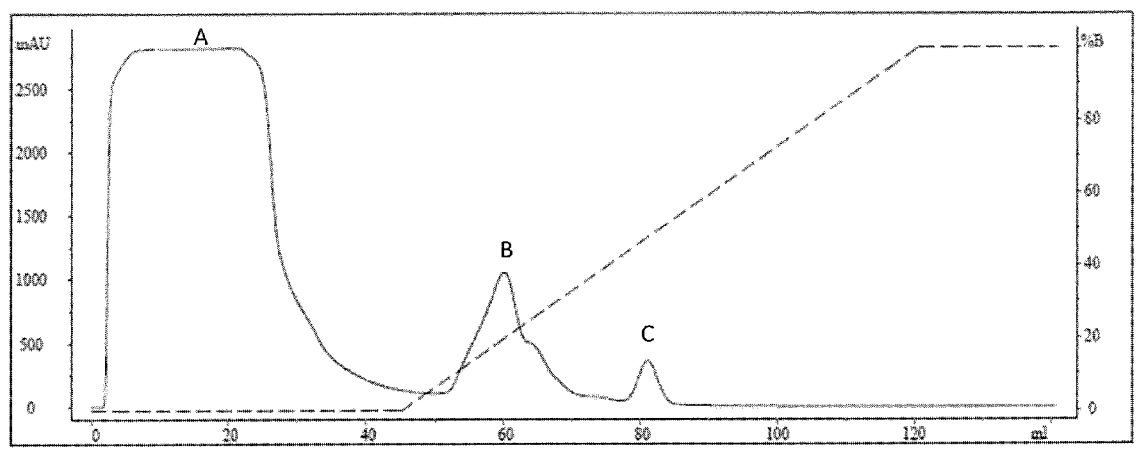
FIG. 1. Chromatogram of IMX313T purified on a Hi Trap heparin HP column. A Heparin-sepharose column clearly separates contaminants (peaks A and B) from the largely pure IMX313T protein (peak C). The dotted line shows the salt gradient used to elute the modified protein.

1. Production of the IMX313, IMX313T and IMX313P Proteins

IMX313 was produced by cloning this oligomerisation domain in a T7-based expression vector by standard methods. The PCR product contained an NdeI site at the N-terminus and a HindIII site overlapping the second stop codon. The nucleotide sequence is:

```
SEQ ID NO 8:
CATATGTCAAAGAAGCAAGGTGATGCTGATGTGTGCGGAGAGGTTGC

TTATATTCAGAGCGTCGTCTCCGATTGCCACGTGCCTACAGCGGAAC

TGCGTACTCTGCTGGAAATACGAAAACTCTTCCTGGAGATTCAAAAA

CTGAAGGTGGAATTGCAAGGACTGAGCAAGGAGTAATAAGCTT
```

This gene encodes the following protein sequence (SEQ ID NO 9):
MSKKQGDADVCGEVAYIQSVVSDCHVP-TAELRTLLEIRKLFLEIQKLKVELQGLSKE**

Asterisks represent stop codons. The serine in the second position enabled complete removal of the initiating methionine, as determined by mass spectrometry.

IMX313 was expressed in the *Escherichia coli* strain C43 (DE3). The transformed cells were grown in Terrific Broth medium at 37° C. to an OD600 of approximately 0.6, then expression was induced with IPTG at a concentration of 1 mM, and the culture was grown overnight at 37° C. The harvested bacteria were lysed by sonication in a buffer containing 50 mM sodium phosphate pH 7.4 and centrifuged at 18,000 rpm for 30 minutes at 4° C. The IMX313 protein was found in the soluble fraction.

IMX313T was generated by replacing the last five C-terminal amino acids (GLSKE) of IMX313 with the positively charged peptide (SPRRRS) as follows: a PstI restriction site (CTGCAG: encoding the amino acids leucine and glutamine) was created by site-directed mutagenesis immediately preceding the amino acids to be substituted (GLSKE). This permits the substitution of the last five amino acids of IMX313 by any amino acids encoded by two complementary oligonucleotides which can be annealed and ligated to the PstI site and the Hind III site just downstream of the stop codons.

The following phosphorylated oligonucleotides replaced the sequence encoding LQGLSKE (SEQ ID NO 10) by LQSPRRRRS (SEQ ID NO 11, where * represents a stop codon), when annealed and cloned between the PstI and HindIII sites:

```
SEQ ID NO 12:
5' GTCTCCGCGTCGCCGTCGCTCCTAATA 3'
and

SEQ ID NO 13:
5' AGCTTATTAGGAGCGACGGCGACGCGGAGACTGCA 3'.
```

The nucleotide sequence encoding IMX313T is as follows (SEQ ID NO 14):
atgtcaaagaagcaaggtgatgctgat-
gtgtgcggagaggttgcttatattca-
gagcgtcgtctccgattgccacgtgcctacagcggaact gcgtactctgctg-
gaaatacgaaaactcttcctggagattcaaaaactgaaggtggaactgcagtctc
cgcgtcgccgtcgctcctaataa IMX313T was also expressed in the *Escherichia coli* strain C43(DE3). The transformed cells were grown in Terrific Broth medium at 37° C. to an OD600 of approximately 0.6, then expression was induced by adding IPTG to 1 mM, and the culture was grown overnight at 37° C. The bacteria were lysed by sonication in a buffer containing 50 mM sodium phosphate pH 7.4 and centrifuged at 18,000 rpm for 30 minutes at 4° C. The IMX313T protein was also found in the soluble fraction.

IMX313P was constructed by mutating the plasmid expressing IMX313T with the oligonucleotides:

```
IMX205:
                                    (SEQ ID NO 43)
5' GGAGATTCAAAAACTGAAGGTGGAAGGTCGCCG
TCGCCGTCGCTCC 3'
and IMX139:
                                    (SEQ ID NO 44)
5' GGGCGATCGGTGCGGGCCTCTTCGC 3'.
```

The PCR product was inserted by the method of Geiser (29) into a T7 vector expressing the IMX313T protein.

The nucleotide sequence encoding IMX313P is as follows (SEQ ID NO 45):

```
ATGTCAAAGAAGCAAGGTGATGCTGATGTGTGCGGAGAGGTTGCT

TATATTCAGAGCGTCGTCTCCGATTGCCACGTGCCTACAGCGGAA

CTGCGTACTCTGCTGGAAATACGAAAACTCTTCCTGGAGATTCAA

AAACTGAAGGTGGAAGGTCGCCGTCGCCGTCGCTCCTAA
```

The IMX313P protein was purified produced in the same manner as the IMX313T protein except that the lysis buffer also contained 1M NaCl. The clarified bacterial lysate was heated at 80° C. for 20 minutes and clarified again by centrifugation at 18,000 rpm for 30 minutes are 4° C.

2. IMX313P and IMX313T, like IMX313, are Heptameric

The protein IMX313T was purified on a Hi Trap SP FF 5 ml column equilibrated with 50 mM sodium phosphate pH 7.4. The protein was eluted in a 0 to 1M NaCl gradient. Fractions containing the protein IMX313T were pooled, dialyzed against 1× PBS and applied to a Hi Load 26/60 Superdex 75 pg column which was equilibrated with 1× PBS. The elution volume for IMX313T (Ve 170 ml) was very similar to that of IMX313 (Ve 162 ml).

The protein IMX313P was purified on a Heparin Sepharose column. The protein was first dialyzed against a solution of Tris-HCl pH8.0 and 150 mM NaCl, before being loaded onto the column. The column was then developed with Tris-HCl pH8.0 and 2M NaCl. The eluted IMX313P protein fractions were pooled, dialyzed against PBS containing 500 mM NaCl, and applied to a Hi Load 26/60 Superdex 75 pg column which was equilibrated with 1× PBS containing 500 mM NaCl. The elution volume was indistinguishable from that of IMX313T.

To demonstrate heptamer formation on SDS-PAGE gels, the purified IMX313T and IMX313P proteins were analyzed under native, denaturing and reducing conditions. In the absence of reducing agent, IMX313T and IMX313P oligomerized, as did IMX313, and all migrated with a much higher molecular weight than their monomers.

3. Fusion of a Short, Positively Charged Peptide to IMX313 Facilitates Protein Purification The IMX313T protein purified as above was subsequently loaded onto a HiTrap Heparin HP 5 ml column in a buffer consisting of 10 mM Tris-HCl and 150 mM NaCl pH 7.5. Elution of bound proteins was carried out with a salt gradient: 15 column volumes of 2M NaCl in the same buffer.

The positively charged IMX313T protein bound to the heparin column and was eluted with approximately 1M NaCl. In a separate column run, it was shown that IMX313 did not bind to the heparin-sepharose column but was found instead in the flow through fraction.

Heparin sepharose is an affinity chromatography column. It is widely used for purifying serum proteins including coagulation factors, lipases, lipoproteins and hormone receptors and has also been used successfully for purifying growth factors. The polyanionic structure of heparin, which serves as an analogue of DNA and RNA, has enabled the purification of many types of proteins that interact with DNA or RNA, including polymerases, ligases, kinases, and ribosomal proteins.

We showed here that modification of coiled coils by fusion of a positively charged peptide (such as a polyarginine tail), confers the useful ability to bind to the negatively charged heparin sepharose column which greatly simplifies purification.

This was unexpected because when Stempfer et al. (19,20) used six arginine residues fused to an enzyme to immobilize the enzyme on Heparin-Sepharose, the enzyme could be eluted from the column with only 0.35 M NaCl. At this concentration of salt, other proteins in cell extracts will also elute as shown in example 4, and there is a significant advantage in being able to elute the vast majority of proteins which do bind to the column with concentrations of salt, such as less than 500 mM NaCl, and then eluting the modified coiled coil fusion protein with even higher concentrations of salt in a substantially pure form. This enables a step gradient or batch purifications to be performed. Thus Heparin-Sepharose columns can be used as affinity columns for proteins fused to IMX313T, and other coiled coils modified in the manner described here.

Compared to cation exchange columns such as Hi Trap SP FF, Heparin-Sepharose columns are more useful because they are more specific for modified coiled coils. In our study, the protein IMX313T which eluted from the cation exchange column (Hi Trap SP FF; pH 7.4) was not totally pure. When this SP FF and S75 purified protein was loaded onto a heparin-sepharose column (HiTrap Heparin HP), the trace contaminants were removed in the flow through, and the IMX313T protein was eluted with a purity >98% showing that heparin column is more specific than SP FF for the coiled coil modified by the addition of the peptide SPRRRRS, although the protein was eluted from both columns at similar concentrations of NaCl.

4. Heparin Sepharose Acts as an Affinity Column for Modified Coiled Coils

IMX313 was produced as described in example 1. The soluble fraction was obtained after sonication of the bacterial lysate in a buffer containing 10 mM Tris-HCl, 150 mM NaCl pH7.5 and centrifugation at 18,000 rpm for 30 minutes at 4° C. in a Sorvall SS34 rotor.

The supernatant containing the fusion protein was loaded on Hi Trap heparin HP column equilibrated with 10 mM Tris-HCl and 150 mM NaCl pH7.5. Elution was carried out with a salt gradient: 2M NaCl in the same buffer. Almost all contaminants were removed in the flow through, or with low concentration of salt; and the IMX313T protein was eluted later with approximately 1M NaCl with a very high purity (approximately 95%) in just a single chromatographic step. Further purification by gel filtration produces an essentially pure protein. Results are presented in FIG. 1.

5. Other Short Positively Charged Peptides Fused to IMX313

Three other modifications of IMX313T were made in order to compare different linkers (glycine versus serine and proline) or to compare arginine with lysine. The plasmid expressing IMX313T was mutated by amplifying with the oligonucleotides:

```
IMX206:
                                    (SEQ ID NO 46)
5' GGAGATTCAAAAACTGAAGGTGGAAGGTCGCCGTCGCCGTT
AATAAGCTTGATCCGGC 3'
or

IMX207:
                                    (SEQ ID NO 47)
5' CTGAAGGTGGAATCTCCGaaaaagaaaaagTAATAAGCTTG
ATCCGGCTG 3'
or IMX208:
                                    (SEQ ID NO 48)
GGAGATTCAAAAACTGAAGGTGGAAGGTAAAAAGAAAAAGTAAT
AAGCTTGATCCGGC 3'
and IMX139
                                    (SEQ ID NO 49)
5' GGGCGATCGGTGCGGGCCTCTTCGC 3'
``` and the PCR product was inserted by the method of Geiser (29) into a T7 vector expressing the IMX313T protein.

The resulting plasmids, called pIMX427, pIMX428 and pIMX429 encode the proteins:

```
IMX427:
                                    (SEQ ID NO 50)
MSKKQGDADVCGEVAYIQSVVSDCHVPTAELRTLLEIRKL
FLEIQKLKVEGRRRR*

IMX428:
                                    (SEQ ID NO 51)
MSKKQGDADVCGEVAYIQSVVSDCHVPTAELRTLLEIRKL
FLEIQKLKVESPKKKK*

IMX429:
                                    (SEQ ID NO 52)
MSKKQGDADVCGEVAYIQSVVSDCHVPTAELRTLLEIRKL
FLEIQKLKVEGKKKK*
```

These were purified as IMX313P was, and then their behaviour on a 5 ml heparin-Sepharose column was examined in comparison with IMX313T and IMX313P.

|         | Ve (ml) | NaCl (mM) | C-terminus | pI   |
|---------|---------|-----------|------------|------|
| IMX428  | 34.4    | 786       | SPKKKK     | 8.88 |
| IMX429  | 37.38   | 817       | GKKKK      | 8.88 |
| IMX313T | 41.18   | 901       | SPRRRRS    | 9.18 |
| IMX427  | 44.24   | 968       | GRRRR      | 9.02 |
| IMX313P | 48.38   | 1058      | GRRRRS     | 9.41 |

The conditions were as follows: Loading buffer 20 mM Tris pH 7.5 150 mM NaCl. Then a gradient elution using a second buffer was carried out. The second buffer was 20 mM Tris pH 7.5 and 2M NaCl.

These results can be compared to the experiments of Fromm and colleagues (47), who showed that a peptide of seven arginines eluted from Heparin Sepharose at a concentration of NaCl of 820 mM, and a peptide of seven lysines eluted at a concentration of 640 mM NaCl. Clearly, the fusion of positively charged peptides to a coiled coil improves their binding to heparin.

6. Production and Purification of the Antigen PAm, and of the Fusion Proteins PAm-IMX313 and PAm-IMX313T To produce the antigen PAm fused to IMX313, the protein A from Staphylococcus aureus open reading frame was amplified from the plasmid pEZZ 18 (Amersham Pharmacia) using the oligonucleotides:

```
IMX1078:
                                    SEQ ID NO 15
5' CTTTAAGAAGGAGATATACATATGgctgatgcgcaacaa
aataac 3'
and IMX1079:
                                    SEQ ID NO 16
5' CCGCACACAtcagcatcaccttgcttttttggtgcttga
gcatcatttagc 3'
``` and the PCR product of ~233 bp base pairs was inserted by the method of Geiser (29) into a T7 vector expressing the IMX313 protein. The protein A reading frame was then mutated using the oligonucleotides:

```
IMX1080:
                                    SEQ ID NO 17
5' cttcaacaaagaAAaaAaGaAcgccttctatg 3'
and IMX1081:
                                    SEQ ID NO 18
5' gcgctttggcttggagccgcttttaagctttgg 3'
``` to introduce the mutations described by Kim et al. (27), creating the expression vector pIMX494, which has the following expression cassette (SEQ ID NO 19):

```
atggctgatgcgcaacaaaataacttcaacaaaggaaaaaagaacgc cttctatgaaatcttgaatatgcctaacttaaacgaagaacaacgca
```

-continued
```
atggtttcatccaaagcttaaaagcggctccaagccaaagcgctaac cttttagcagaagctaaaaagctaaatgatgctcaagcaccaaaaaa gcaaggtgatgctgatgtgtgcggagaggttgcttatattcagagcg tcgtctccgattgccacgtgcctacagcggaactgcgtactctgctg gaaatacgaaaactcttcctggagattcaaaaactgaaggtggaatt gcaataataa
```

This encodes the following protein (SEQ ID NO 20):

```
MADAQQNNFNKGKKNAFYEILNMPNLNEEQRNGFIQSLKAAPSQSAN

LLAEAKKLNDAQAPKKQGDADVCGEVAYIQSVVSDCHVPTAELRTLL

EIRKLFLEIQKLKVELQ**
```

Note that this version of IMX313 lacks the last five amino acids (GLSKE) found in the fifty-five amino acid version to facilitate the interpretation of the planned immunizations. The IMX494 fusion protein (PAm-IMX313) was expressed in the C43(DE3) strain on induction with IPTG. The cell pellet was lysed by sonication in 20 mM Tris-HCl pH 7 and centrifuged at 18,000 rpm for fifteen minutes at 4° C. The fusion protein was found in the pellet which was then sonicated in a buffer composed of 50 mM Tris-HCl, 3M urea pH 7.4 and centrifuged again at 18 000 rpm. This time, the fusion protein was in the supernatant, which was loaded on Hi Trap Q FF 5 ml column and the column developed with a 1M NaCl gradient.

Fractions containing the IMX494 protein were pooled dialysed against PBS and further purified by gel filtration on a Hi Load 26/60 Superdex 75 column.

To produce the antigen PAm unfused to the carrier protein, the IMX313 coding sequence was deleted from the vector pIMX494 using the oligonucleotides: SEQ ID NO 21—IMX1279 5' gcagccggatcaagcttattattttggtgcttgagcatc 3' and SEQ ID NO 22—T7 Forward: 5' TAATACGACTCACTATAGGG 3'. The PCR product was inserted (27) into the parental vector creating the plasmid pIMX495.

A 500 ml culture of pIMX495 in the strain C43(DE3) was induced with 1 mM IPTG and grown overnight. The harvested bacteria were lysed by sonication in the buffer: 50 mM sodium phosphate pH 7.4 and centrifuged at 18,000 rpm for 15 minutes at 4° C. in a Sorvall SS34 rotor. The protein IMX495 (PAm without its N-terminal methionine) was found in the supernatant, and purified by heating the supernatant at 76° C. for fifteen minutes followed by a second centrifugation at 18 k for 15 minutes. Once again, IMX495 was found in the supernatant, which was dialysed against a buffer of 50 mM MES pH6. The supernatant was loaded onto a Hi Trap SP FF 5 ml column and eluted with a gradient of NaCl. Finally, the IMX495 protein was polished by gel filtration in PBS on a Hi prep 26/60 sephacryl S-100 HR column.

To produce the vector pIMX497 encoding the fusion protein PAm-IMX313T, the vector pIMX494 was modified by synonymously mutating the sequence encoding the last two amino acids leucine and glutamine from TTGCAA to CTGCAG, and then cloning between the newly created Pst I site and the Hind III site overlapping the second stop codon the oligonucleotides;

SEQ ID NO 23
5' GTCTCCGCGTCGCCGTCGCTCCTAATA 3'
and

SEQ ID NO 24
5' AGCTTATTAGGAGCGACGGCGACGCGGAGACTGCA 3' changing the C-terminus of IMX313 from LQ to LQSPRRRRS (SEQ ID NO 11).

The encoded protein IMX497 was then expressed in the C43(DE3) strain and purified by lysing the bacterial pellet in 50 mM sodium phosphate pH 7.4 and centrifuging at 18 k rpm. The fusion protein was found in the pellet and was resuspended by sonication in 50 mM sodium phosphate, 8M urea, pH 7.4. After a further centrifugation, the supernatant was dialysed against 50 mM sodium phosphate pH 7.4 and the dialysate was centrifuged. The supernatant was heated to 75° C. for fifteen minutes and then centrifuged again. The supernatant was purified on a Hi Trap SP FF column developed with an NaCl gradient to 2M, and fractions containing the IMX497 fusion protein were pooled, dialysed against PBS and polished by gel filtration on a Hi Load 26/60 superdex 75 column.

7. Binding of Intracellular TLR Ligands

To determine whether these proteins could bind intracellular TLR ligands, electrophoretic mobility shift assays (EMSAs) were carried out.

Different combinations of intracellular TLR ligands and the IMX497 protein (PAm-IMX313T) were prepared, and complex formation was analyzed by agarose gel electrophoresis.

The TLR ligands used were as follows:
For TLR3: poly I:C being a duplex of a polynucleotide of polyinosinic acid hybridized to polycytidylic acid, an analogue of double-stranded RNA. The chain length was twenty nucleotides for each strand.
For TLR7: an oligonucleotide, called ssRNA40, with the sequence 5' GsCsCsCsGsUsCsUsGsUsUsGsUsG-sUsGsAsCsUsC 3' where "s" represents a phosphothioate linkage (SEQ ID NO 25);
For TLR9: an oligonucleotide called ODN1826 with the sequence: 5' tccatgacgttcctgacgtt 3' (SEQ ID NO 26).

Figure 2:
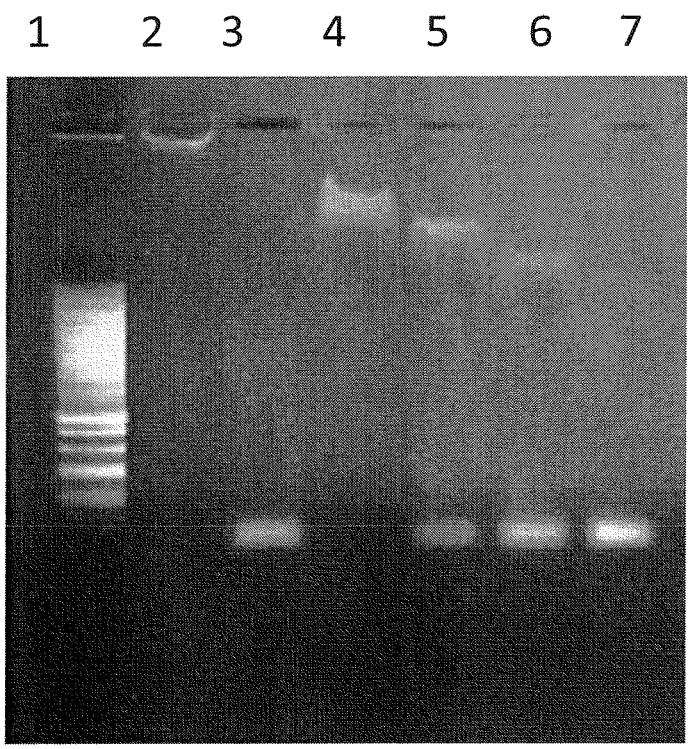
FIG. 2. TLR 9 ligands and the IMX497 protein (PAm-IMX313T)—Agarose gel electrophoresis (0.8% in TAE buffer). The position in the gel to which the oligonucleotide migrated is observable under ultraviolet light when the gel is stained with ethidium bromide.

For the TLR9 ligands, results are presented on FIG. 2. From left to right:
Lane 1: Low molecular mass ladder (NEB);
Lane 2: Protein IMX497 (1 mg/ml);
Lane 3: FITC CpG ODN (Eurogentec) 10 μM;
Lane 4: Protein IMX497 (1 mg/ml) & FITC CpG ODN 10 μM;
Lane 5: Protein IMX497 (0.5 mg/ml) & FITC CpG ODN 10 μM;
Lane 6: Protein IMX497 (0.25 mg/ml) & FITC CpG ODN 10 μM;
Lane 7: Protein IMX497 (0.125 mg/ml) & FITC CpG ODN 10 μM.

Complex formation was clearly detectable, because the complexes migrated much more slowly than the uncomplexed ligand, thus "shifting" the ligand on the gel. As the concentration of the protein was decreased, the observed complexes became more diffuse, and a band of unbound TLR ligand became visible (it migrated the same distance as the sample containing only the TLR ligand used as a control).

Figure 3:
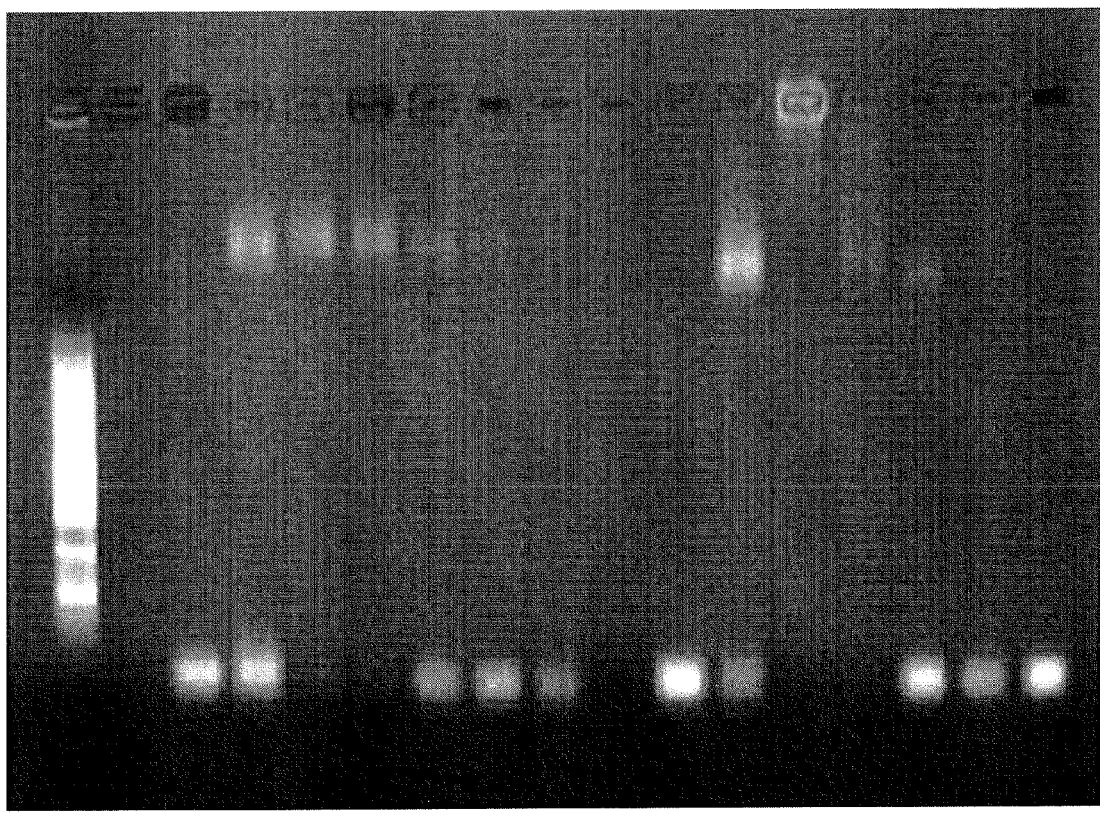
FIG. 3. TLR7 and TLR3 ligands and the IMX497 protein (PAm-IMX313T)—Agarose gel electrophoresis (0.8% in TAE buffer).

Combinations of the protein IMX497 with TLR7 and TLR3 ligands are shown on FIG. 3; these nucleic acids also formed complexes which were easily detected by EMSAs.

Legend of FIG. 3 (TLR7 ligands or TLR3 ligands+IMX497):
Lane 1: low mass ladder (NEB);
Lane 2: Protein IMX497(1 mg/ml);
Lane 3: FITC ssRNA (Eurogentec) 10 μM;
Lane 4: Protein IMX497 (1.5 mg/ml)/FITC ssRNA 10 M;
Lane 5: Protein IMX497 (1 mg/ml)/FITC ssRNA 10 M;
Lane 6: Protein IMX497 (0.5 mg/ml)/FITC ssRNA 10 M;
Lane 7: Protein IMX497 (0.25 mg/ml)/FITC ssRNA 10 M;
Lane 8: Protein IMX497 (0.125 mg/ml)/FITC ssRNA 10 M;
Lane 9: FITC ssRNA 10 M;
Lane 10: Negative Control;
Lane 11: Poly (I:C)(R&D TOCRIS Bioscience) 0.5 mg/ml;
Lane 12: Protein IMX497 (1.5 mg/ml)/Poly (I:C) 0.5 mg/ml;
Lane 13: Protein IMX497 (1 mg/ml)/Poly (I:C) 0.5 mg/ml;
Lane 14: Protein IMX497 (1 mg/ml)/Poly (I:C) 0.25 mg/ml;
Lane 15: Protein IMX497 (0.5 mg/ml)/Poly (I:C) 0.5 mg/ml;
Lane 16: Protein IMX497 (0.5 mg/ml)/Poly (I:C) 0.25 mg/ml
Lane 17: Protein IMX497 (0.25 mg/ml)/Poly (I:C) 0.5 mg/ml We also examined whether IMX494 (PAm-IMX313) and IMX495 (PAm) could also produce such gel shifts with the CpG oligonucleotide (TLR9 ligands). Results are shown on FIG. 4.

Figure 4:
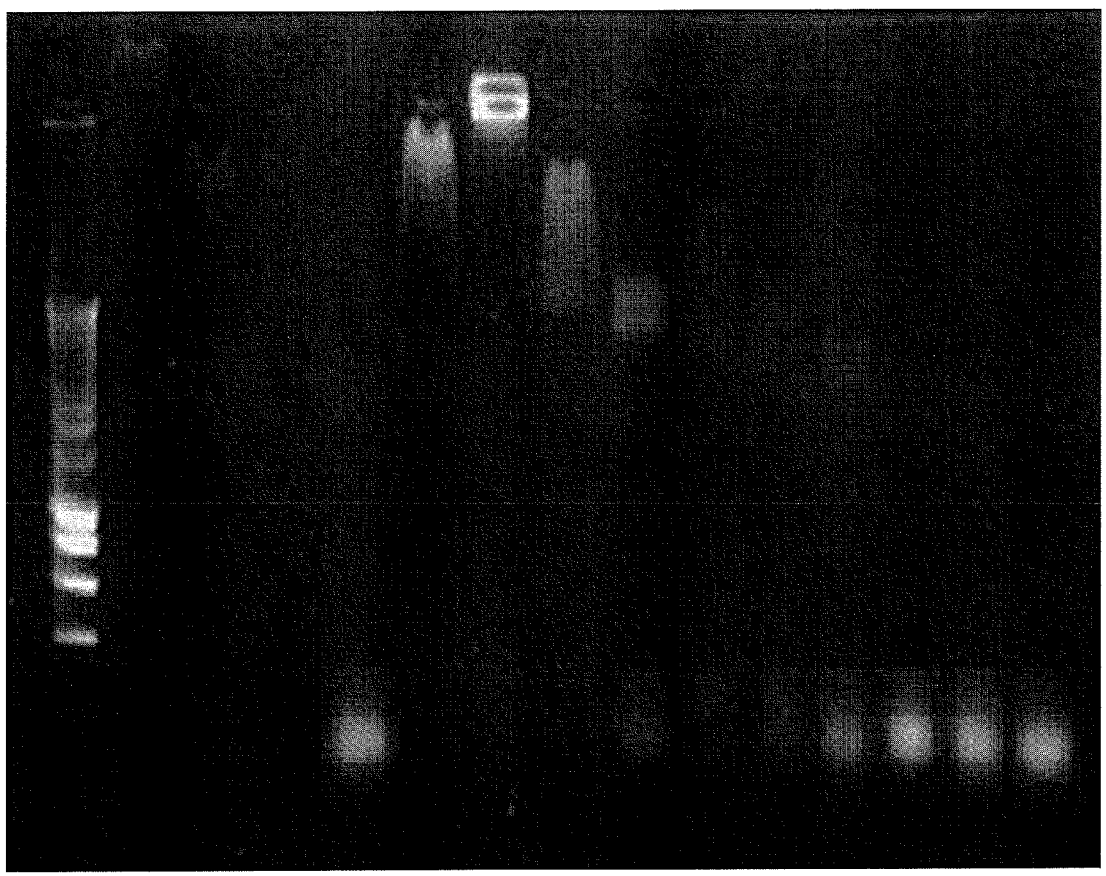
FIG. 4. TLR7 ligands and the IMX495 (PAm), IMX494 (PAm-IMX313) and IMX497 (PAm-IMX313T) proteins—Agarose gel electrophoresis (0.8% in TAE buffer).

Legend of FIG. 4:
Lane 1: low molecular mass ladder (NEB);
Lane 2: Protein IMX497 (1 mg/ml);
Lane 3: Protein IMX494 (1 mg/ml)
Lane 4: Protein IMX495 (1 mg/ml)
Lane 5: FITC CpG ODN (Eurogentec) 10 μM;
Lane 6: Protein IMX497 (1.5 mg/ml) & FITC CpG ODN 10 μM;
Lane 7: Protein IMX497 (1 mg/ml) & FITC CpG ODN 10 μM;
Lane 8: Protein IMX497 (0.5 mg/ml) & FITC CpG ODN 10 μM;
Lane 9: Protein IMX497 (0.25 mg/ml) & FITC CpG ODN 10 μM;
Lane 10: Protein IMX494 (1 mg/ml) & FITC CpG ODN 10 μM;
Lane 11: Protein IMX494 (0.5 mg/ml) & FITC CpG ODN 10 μM;
Lane 12: Protein IMX494 (0.25 mg/ml) & FITC CpG ODN 10 μM;
Lane 13: Protein IMX495 (1 mg/ml) & FITC CpG ODN 10 μM;
Lane 14: Protein IMX495 (0.5 mg/ml)& FITC CpG ODN 10 μM;
Lane 15: Protein IMX495 (0.25 mg/ml) & FITC CpG ODN 10 μM The gel in FIG. 4 shows that the gel shift is reproducible with IMX497, but that IMX495 (lanes 13-15) produces no detectable gel shift and that the gel shifts seen with IMX494 (lanes 10-12) are barely detectable, and much less marked than those seen with IMX497.

The difference between IMX494 and IMX497 is the presence of the sequence SPRRRRS present in IMX497, fused to the C-terminus of the coiled coil of the protein.

Conclusion: without the peptide, the fusion protein IMX313 and antigen PAM is unable to bind nucleic acid ligands for TLR receptors.

8. Immunogenicity of Antigens Associated with IMX313T

Immunisations of mice were then performed to determine the immunogenicity of PAm, whether alone or fused to IMX313 or IMX313T, and with or without formulation with the intracellular TLR ligands. PAm formulated with complete or incomplete Freund's adjuvant (CFA/IFA) was used as a control.

To this end, female BALB/C mice were immunized subcutaneously twice, with a 14 day interval, using 2 nanomoles of each protein per injection, with PAm, PAm-IMX313, PAm-IMX313T or PAm formulated first in CFA and then in IFA. Twenty-eight days after the first immunization, the PAm-specific IgG titers in sera were determined using an ELISA in which plates were coated with PAm. Results are expressed as the OD of samples measured at 405 nm+SEM. Significant differences between the means of different groups were determined by one-way ANOVA followed by Tukey's multiple comparison test. A p-value of <0.05 was considered statistically significant. and is represented by different *, whereas * represents p<0.001 and  is represents p<0.01.

Figure 5:
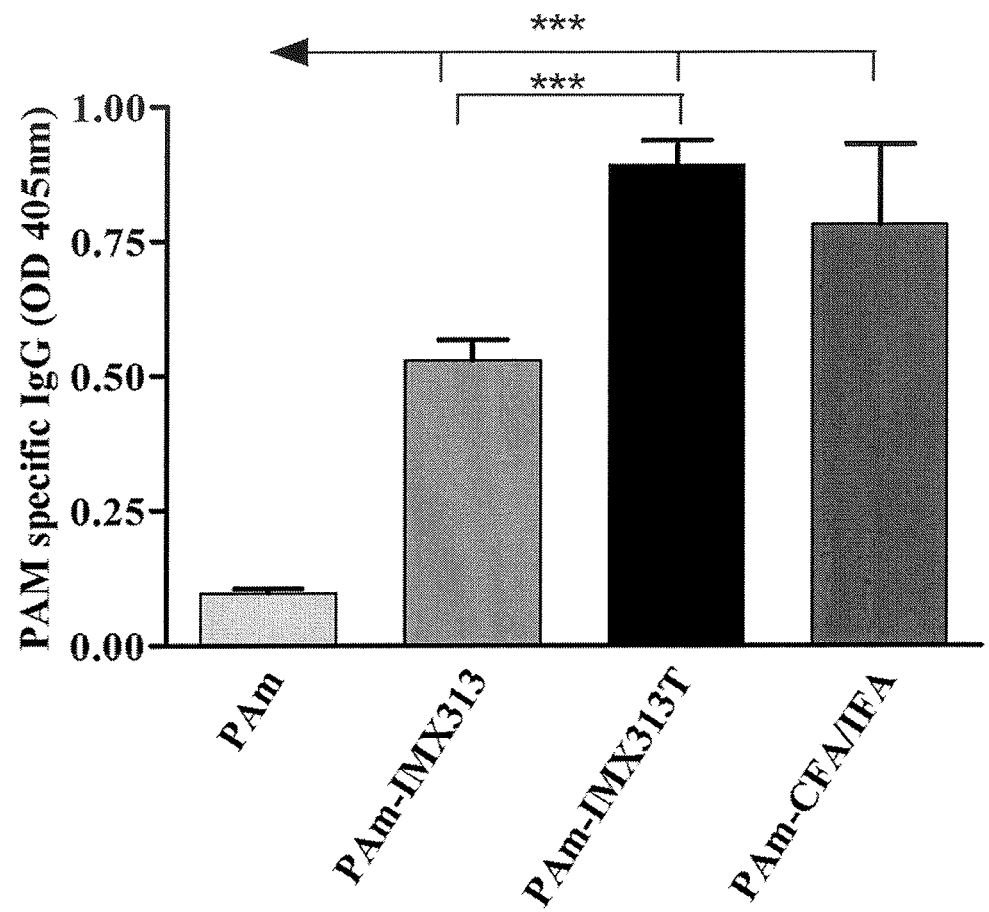
FIG. 5. Groups of female BALB/C mice (n=5) were subcutaneously immunized twice, at a fourteen day interval, with PAm, PAm-IMX313, PAm-IMX313T or PAm formulated first in CFA and then in IFA. Twenty-eight days after the first immunization, the PAm-specific IgG titers in sera were determined using an ELISA in which plates were coated with PAm. Results are expressed as the OD of samples measured at 405 nm+SEM. Significant differences between the means of different groups were determined by one-way ANOVA followed by Tukey's multiple comparison test. A p-value of <0.05 was considered statistically significant. and is represented by different *, whereas * represents p<0.001 and  represents p<0.01.

Results are shown on FIG. 5. Mice immunized with PAm alone had no or very low levels of anti-PAM IgG antibody in their sera. Mice immunized with PAm-IMX313 or PAm-IMX313T on the other hand, showed high levels of systemic PAm-specific IgG antibody responses; however, the PAm-IMX313T immunized mice had significantly higher (p<0.001) IgG antibody responses compared to those of the PAm-IMX313 immunized mice; responses similar to PAm-IMX313T were obtained with PAm+CFA/IFA as adjuvants.

This shows that the addition of the peptide SPRRRRS confers a significantly improved immunogenicity to the antigen compared to the parental sequence IMX313.

When the antigen PAm was formulated with the intracellular TLR ligands (whether single-stranded DNA or RNA or double-stranded RNA), its immunogenicity was substantially improved, and similar improvements were seen when the antigen was fused to IMX313 before formulation. However, clearly the best results were seen when the antigen was fused to IMX313T before being formulated with the TLR ligands.

The results are tabulated here and shown diagrammatically below.

TABLE 1

| IgG End Point Dilution Titers against PAm | | | |
|---|---|---|---|
| | PAm | PAm-IMX313 | PAm-IMX313T |
| Without adjuvant | 0 | 800 | 1600 |
| With Poly I:C | 100 | 3200 | 12800 |
| With ODN CpG | 100 | 3200 | 6400 |
| With ssRNA | 0 | 2400 | 6400 |
| With CFA/IFA | 1600 | — | — |

An interesting question is whether these improvements modify the types of immune responses obtained against the antigen, in this case PAm. Are Th1 or Th2 responses selectively improved? To answer this, we compared the IgG1 responses with IgG2a responses, as IgG1 titers are representative of Th2 type responses, while IgG2a represent Th1 type responses. Results are presented in table 2.

It is clear that PAm on its own induces almost equally Th1 and Th2 responses, but its formulation with Freund's adjuvant changes this dramatically, with the Th2 response (IgG1) being now predominant. Fusion of PAm to IMX313 shows that both Th1 and Th2 responses are both increased, and there is no significant shift in the type of response. With IMX313T, the Th1 response (IgG2a) starts to predominate, but the effect is much less marked than with Freund's and in the opposite direction. The consensus among immunologists is that Th1 responses are preferable to Th2 responses.

Taking this analysis further, we examined whether the formulation with intracellular TLR ligands could be used to re-direct the immune system to produce either Th1 or Th2 responses. IgG antibody isotype data were used to evaluate the type of Th response, with a predominance of IgG2a or IgG1 antibodies indicating a Th1- or Th2-like response, respectively. Th1-like responses had very high IgG2a-to-IgG1 ratios, such that the group mean was also high. IgG2a/IgG1 ratio was used as an indicator of either a predominantly Th1 (IgG2a >IgG1), predominantly Th2 (IgG1>IgG2a), or a mixed Th1/Th2 (Th0, IgG1=IgG2a) response.

The results are shown in the table 2 below:

| Immunogenic composition | PAm specific IgG1 | PAm specific IgG2a | IgG2a/IgG1 ratio | TH response |
|---|---|---|---|---|
| PAm | 0.147 | 0.150 | 1.02 | Th0 |
| PAm-CFA/IFA | 0.530 | 0.241 | 0.45 | Th2 |
| PAm-IMX313 | 0.387 | 0.497 | 1.28 | Th1 |
| PAm-IMX313T | 0.436 | 0.686 | 1.57 | Th1 |
| PAm-IMX313T + TLR9 ligands | 0.301 | 0.896 | 2.97 | Th1 |
| PAm-IMX313T + TLR7 ligands | 0.391 | 0.71 | 1.81 | Th1 |
| PAm-IMX313T + TLR3 ligands | 0.424 | 1.28 | 3.25 | Th1 |

It is immediately apparent that formulation of PAm-IMX313T with the TLR ligands increases the tendency of the Th1 response to predominate, with each of the three ligands; the effect is most marked with the TLR3 ligand poly I:C and almost as marked with the TLR9 ligand.

9. T Cell Responses

To determine whether the modification of the IMX313 coiled coil with the positively charged peptide could also improve T cell responses, we used the mycobacterial antigen 85A as a model, because IMX313 has been shown to improve T cell responses to this antigen in mice and monkeys (28). A series of recombinant plasmids expressing the antigen 85A alone or fused to IMX313T or to two truncated versions of IMX313, containing only fourteen or eighteen amino acids thereof, was made by first subcloning the 85A-IMX313 coding sequence from the pSG2-85A-IMX313 vector described by Spencer et al. (28) into the Gateway plasmid pENTR4-LP. In this pENTR4 backbone, derivatives were made either to delete or modify IMX313.

The amino acid sequences of the IMX313 variants are shown here:

```
IR14
                                           (SEQ ID NO 27)
IRKLFLEIQKLKVE*

TL18
                                           (SEQ ID NO 28)
TLLEIRKLFLEIQKLKVE*

IMX313
                                           (SEQ ID NO 6)
KKQGDADVCGEVAYIQSVVSDCHVPTAELRTLLEIRKLFL
EIQKLKVELQGLSKE*

IMX313T
                                           (SEQ ID NO 7)
KKQGDADVCGEVAYIQSVVSDCHVPTAELRTLLEIRKLFL
EIQKLKVELQSPRRRRS*
```

The 14-mer and 18-mer fragments of IMX313 were chosen because they remained heptameric at 37° C., (and even 42° C.), and should thus form heptameric fusion proteins when expressed after DNA vaccination. The modifications of IMX313 were carried out as follows:

The forward primers IMX043 and IMX044 and the reverse primer IMX045 were used to amplify the fragments of IMX313 and this PCR product was used (29) to replace IMX313 in the parental plasmid.

```
IMX043:
                                           (SEQ ID NO 29)
5' gaagcccgacctgcaacgtggatccATACGAAAACTC
TTCCTGGAGA 3'

IMX44:
                                           (SEQ ID NO 30)
5' gaagcccgacctgcaacgtggatccACTCTGCTGGAA
ATACGA 3'

IMX45:
                                           (SEQ ID NO 31)
5' agggccctctagatgcatgctcgagcggccgcttatt
aTTCCACCTTCAGTTTTTG 3'
```

The IMX313 coding sequence was deleted using the primers IMX037 and IMX047 and the parental plasmid as a template; the resulting PCR product was then used (29) to replace the IMX313 sequence.

```
IMX037:
                                           (SEQ ID NO 32)
5' cagaatagaatgacacctactcag 3'

IMX047:
                                           (SEQ ID NO 33)
5' GAAGCCCGACCTGCAACGTTAATAAgcggccgctcgagcatg 3'
```

To make 85A-IMX313T, the following oligos were used to amplify IMX313T from the plasmid pIMX497; the PCR product was then inserted (29) into the parental plasmid:

```
IMX1030:
                                           (SEQ ID NO 34)
5' GTGCCTACAGAGGACGTGAAAATGCTGCTGGAAATACG
AAAACTCTTCCTGG 3'

IMX046:
                                           (SEQ ID NO 35)
5' Agggccctctagatgcatgctcgagcggccgcttatta
GGAGCGACGGCGACGCGGAGA 3'
```

These five plasmids (encoding 85A, 85A-IR14, 85A-TL18, 85A-IMX313 and 85A-IMX313T) were then used for DNA immunizations.

Fives groups of BALB/c mice were immunized intramuscularly with each of the five plasmids on days 0 and 14, using 25 μg per injection. The induction of antigen-specific T-cell responses were measured by ELISPOTs, using splenocytes, on day 28. Purified spleen CD4+, CD8+ and Total T cells isolated from the immunized mice were co-cultured with either recombinant 85A protein (Clinibiosciences) or the peptides p11 or p15 (26) purchased from Eurogentec.

ELISPOT Assays: Flat-bottomed, 96-well nitrocellulose plates (Millititer; Millipore) were coated with IFN-γ mAb (15 μg/ml; MABTECH, Stockholm) and incubated overnight at 4° C. After washing with PBS, plates were blocked with 10% fetal bovine serum for one hour at 37° C. $2 \times 10^6$ cells per well were stimulated with relevant peptides at a final concentration of 2 μg/ml (CD8 epitope p11, CD4 epitope p15 or 85A protein) on IPVH-membranes coated with 15 μg/ml anti-human IFN- and incubated for 20 hours. After incubation, the plates were washed thoroughly with PBS to remove cells, and IFN-γ mAb (1 μg/ml of biotin, MABTECH) was added to each well. After incubation for 2 h at 37° C., plates were washed and developed with streptavidin-HRP (1 μg/ml; MABTECH) for one hour at room temperature. After washing, the substrate (3-amino-9-ethycarbazol (Sigma)) was added and incubated for 15 minutes. After further washing, the red spots were counted under the microscope.

Figure 6:
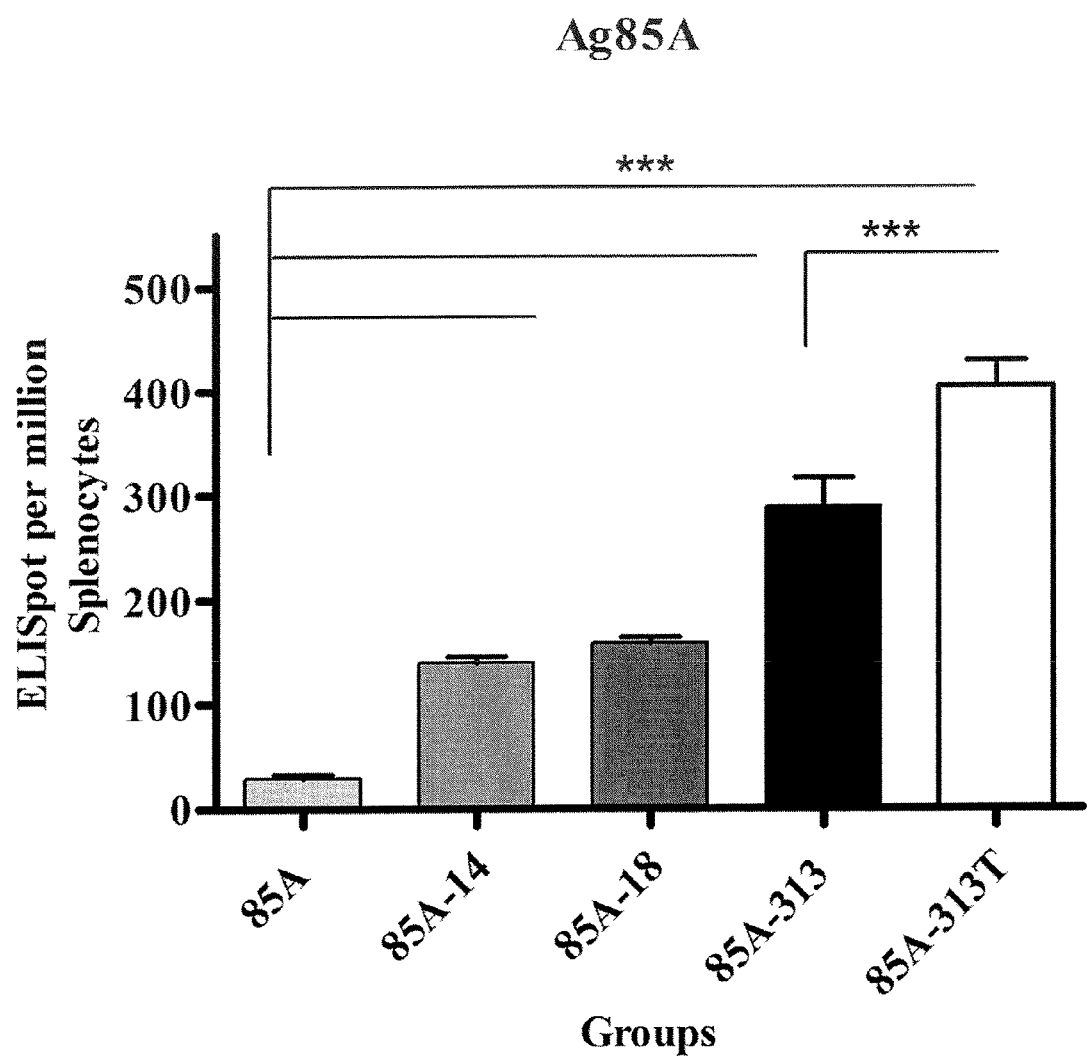
FIG. 6. IFN-γ expression levels in total T cell populations. 85A-specific cell-mediated immune responses in intramuscularly immunized mice. Groups of female BALB/c mice (n=5) immunized twice, 14 days apart, with plasmids expressing: 85A, 85A-IR14, 85A-TL18, 85A-IMX313 or 85A-IMX313T. Two weeks after the last immunization, the mice were sacrificed and spleen T cells were purified. Cells were co-cultured with recombinant 85A protein. Significant differences between the means of different groups were determined by one-way ANOVA followed by Tukey's multiple comparison test. A p-value of <0.05 was considered statistically significant. IFN-γ responses in co-culture supernatants are expressed as cells secreting IFN-γ/million of cells.

Purified spleen CD4+ T, CD8+ T and Total T cells isolated from the 85A-IMX313, 85A-IR14 or 85A-TL18 or 85A-IMX313T immunized mice showed significantly higher IFNγ responses compared with those of the 85A immunized mice, and confirmed the ability of IMX313 and the other modified sequences to increase T cell responses. Further, spleen CD4+, CD8+ and total T cells from the 85A-IMX313T vaccinated mice produced significantly more IFNγ than those of any of the other immunized groups (p<0.001) (FIGS. 6, 7, 8).

Figure 7:
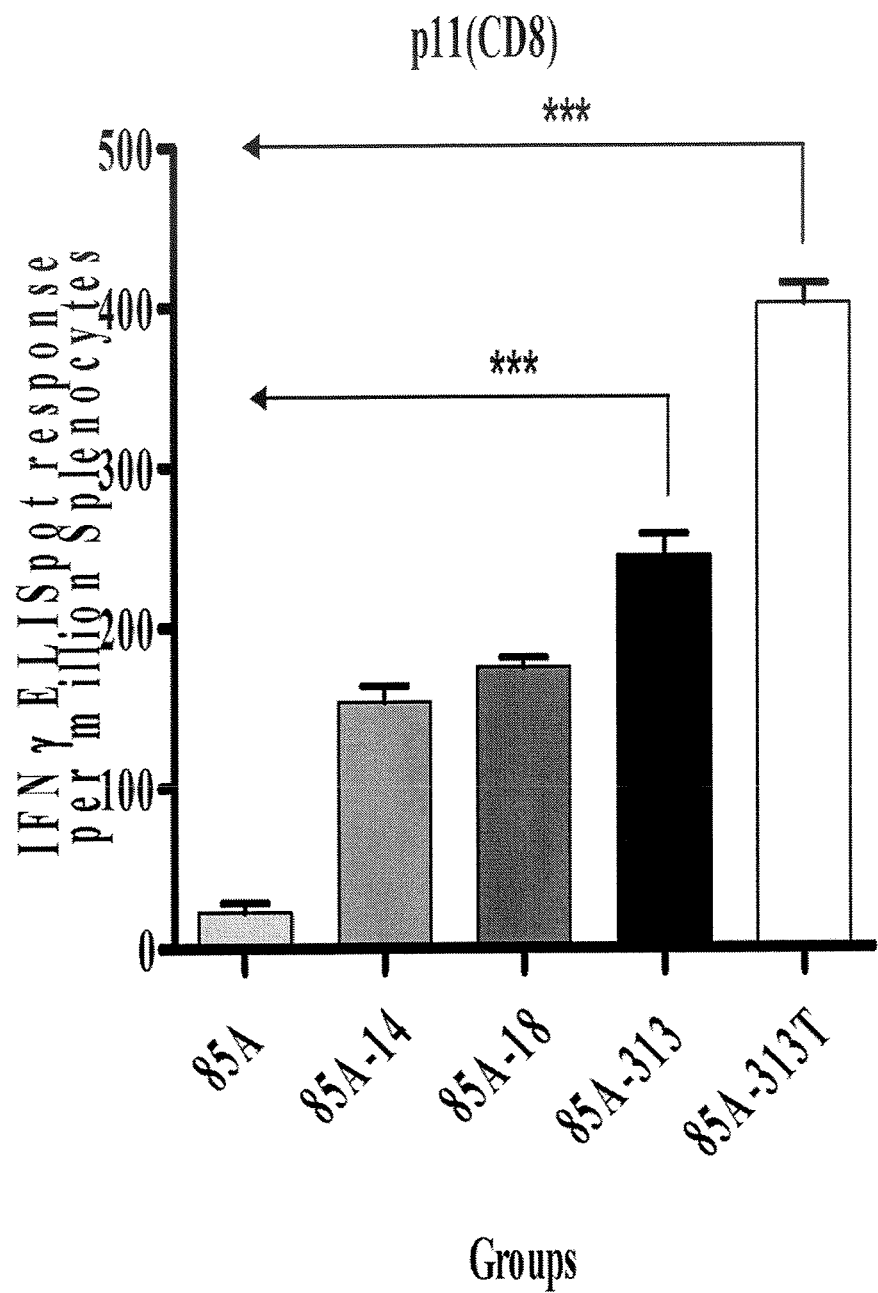
FIG. 7. IFN-γ expression levels in CD8+T cell populations. 85A-specific cell-mediated immune responses in intramuscularly immunized mice. Groups of female BALB/c mice (n=5) immunized twice, 14 days apart, with plasmids expressing: 85A, 85A-IR14, 85A-TL18, 85A-IMX313, or 85A-IMX313T. Two weeks after the last immunization, the mice were sacrificed and purified splenic CD8+ T cells. Cells were co-cultured with the 85A peptide p11. Significant differences between the means of different groups were determined by one-way ANOVA followed by Tukey's multiple comparison test. A p-value of <0.05 was considered statistically significant. IFN-γ responses in co-culture supernatants were expressed as cells secreting IFN-γ/million of cells.
Figure 8:
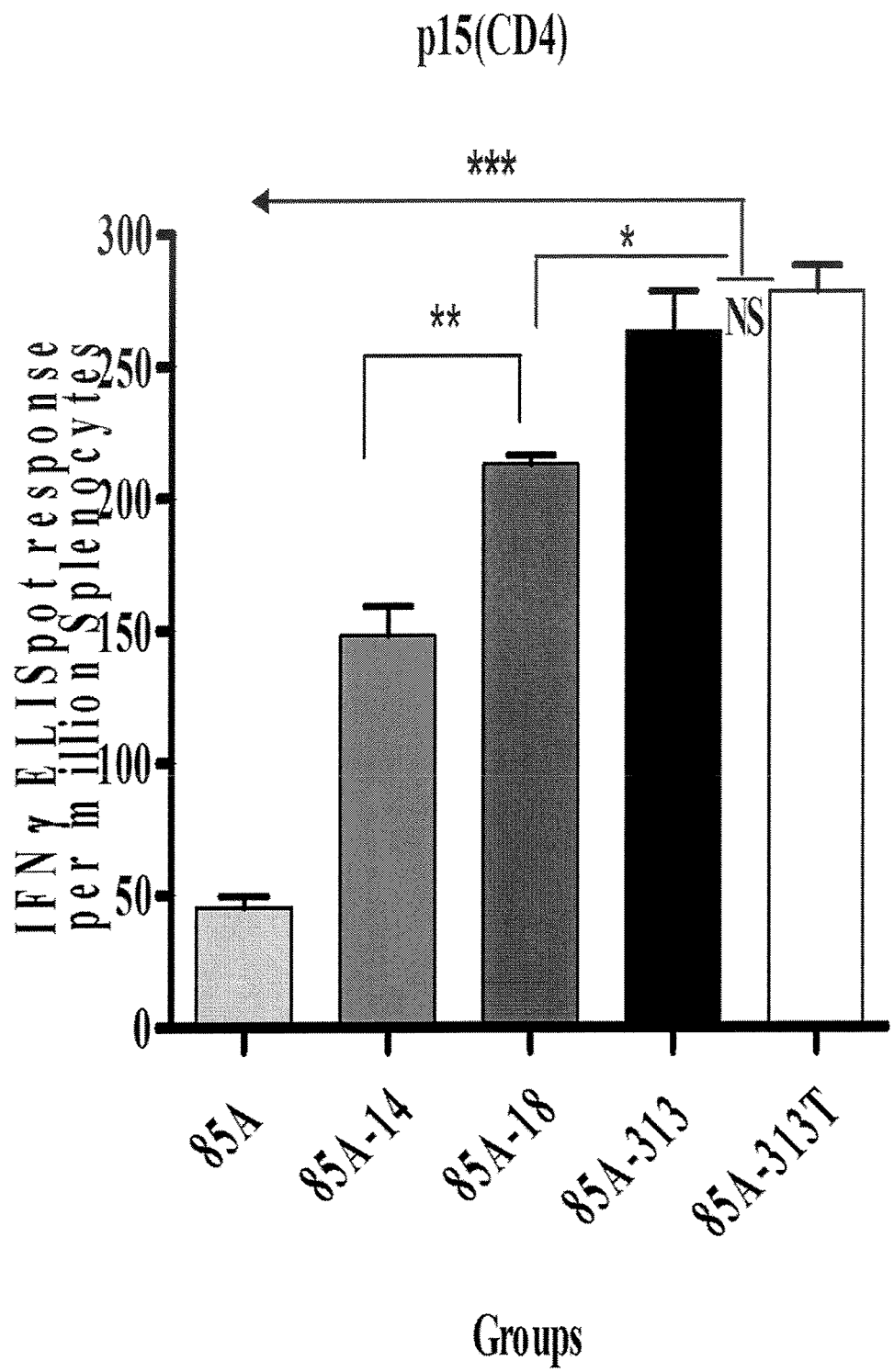
FIG. 8. IFN-γ expression levels in CD4+T cell populations. 85A-specific cell-mediated immune responses in intramuscularly immunized mice. Groups of female BALB/c mice (n=5) immunized twice, 14 days apart, with plasmids expressing: 85A, 85A-IR14, 85A-TL18, 85A-IMX313 or 85A-IMX313T. Two weeks after the last immunization, the mice were sacrificed and purified splenic CD8+ T cells. Cells were co-cultured with the 85A peptide p15. Significant differences between the means of different groups were determined by one-way ANOVA followed by Tukey's multiple comparison test. A p-value of <0.05 was considered statistically significant. IFN-γ responses in co-culture supernatants were expressed as cells secreting IFN-γ/million of cells.

The CD8+ T cells demonstrated a different cytokine profile compared to CD4+ T cells; the predominant cytokine producing population observed was CD8+ T cells that produced IFN-γ (FIGS. 7 & 8).

It is noteworthy that both CD4+ and CD8+ antigen-specific T cells responses are enhanced when IMX313 is replaced by IMX313T.

In conclusion, T cell responses to the antigen 85A, which are improved by IMX313 are further improved by the use of IMX313T instead.

10. B Cells Responses Induced by DNA Vaccination

Figure 9:
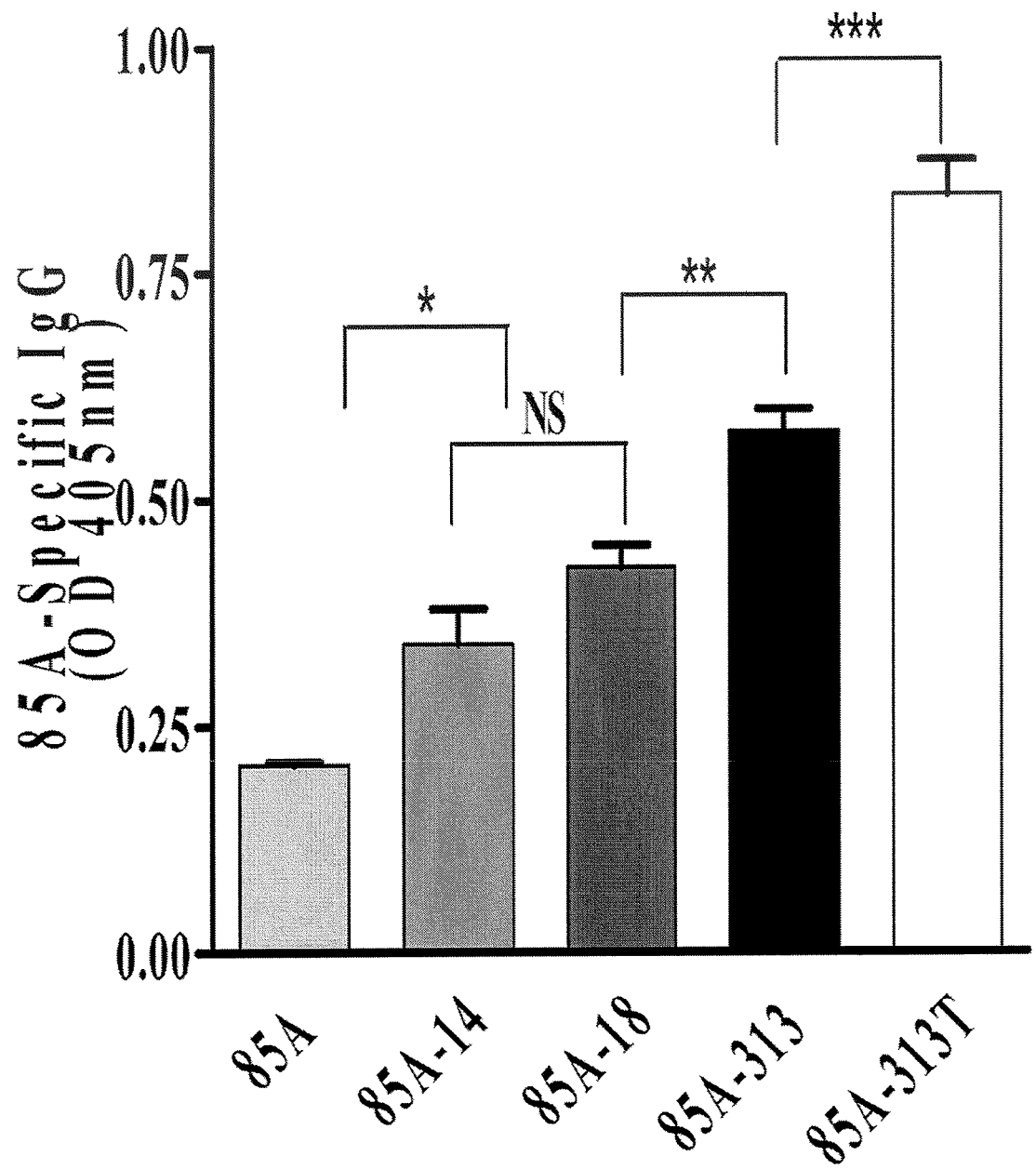
FIG. 9. Groups of female BALB/C mice (n=5) were immunized intramuscularly twice, 14 days apart, with the 85A-IMX313 plasmid, the 85A-IMX313T plasmid and the shorter sequences 85A-IR14 and 85A-TL18. Twenty-eight days after the first immunization, the 85A-specific IgG levels in sera were determined using an 85A-specific ELISA. Results are expressed as the OD of samples measured at 405 nm+SEM. Significant differences between the means of different groups were determined by one-way ANOVA followed by Tukey's multiple comparison test. A p-value of <0.05 was considered statistically significant. NS, means not significant; significance values are shown by asterisks: *(p<0.001), (p<0.01),* (p<0.05)

Antibody titers to the antigen 85A were measured by ELISAs in the sera of the mice which were immunized with DNA vaccines (FIG. 9).

Mice immunized with the 85A-IMX313 plasmid, the 85A-IMX313T plasmid and the shorter versions of IMX313 (IR14 and TL18) developed significantly higher antigen-specific total IgG titers (FIG. 9) those immunized with the plasmid expressing 85A. The group immunized with 85A-IMX313T showed the highest IgG responses (p<0.001). Mice immunized with 85A alone had very low levels of anti-85A IgG antibody in their sera.

The redirection of immune responses towards Th1 when the short positively charged peptide SPRRRRS is added was also seen when DNA is used for vaccination. We measured the IgG isotypes specific for the 85A protein in ELISAs (table 3). The IgG2a isotype is associated with a Th1 and the IgG1 isotype is associated with a Th2 type immune response in BALB/c mice.

Of note, the use of either IMX313 or IMX 313T led to a shift toward T helper type 1 (Th1) associated antigen-specific IgGs, with significantly elevated levels of IgG2a and reduced levels of IgG1 compared to antigen 85A alone (table 3) and these results constitute direct evidence of a Th1 polarization; these results are consistent with the results seen with the cellular immune responses.

Table 3. Groups of female BALB/C mice (n=5) were immunized intramuscularly twice, 14 days apart, with plasmids expressing 85A-IMX313, 85A-IMX313T, the shorter IMX313 sequences 85A-IR14 and 85A-TL18, and 85A alone. Twenty-eight days after the first immunization, the 85A-specific IgG1 and IgG2a levels in sera were determined using an 85A-specific ELISA. Results are expressed as the OD of samples measured at 405 nm+SEM. When we analyse as above, the same data to classify these isotype data, we see:

TABLE 3

|  | IgG2a/IgG1 ratio | TH response |
| --- | --- | --- |
| 85A | 0.8 | Th2 |
| 85A-IR14 | 1.6 | Th1 |
| 85A-TL18 | 1.47 | Th1 |

TABLE 3-continued

|  | IgG2a/IgG1 ratio | TH response |
| --- | --- | --- |
| 85A-IMX313 | 1.73 | Th1 |
| 85A-IMX313T | 2.57 | Th1 |

Clearly, all versions of IMX313 tend to augment preferentially the Th1 responses, and the effect is most marked with the version of IMX313T which has the short positively charged peptide fused to the coiled coil.

Figure 10:
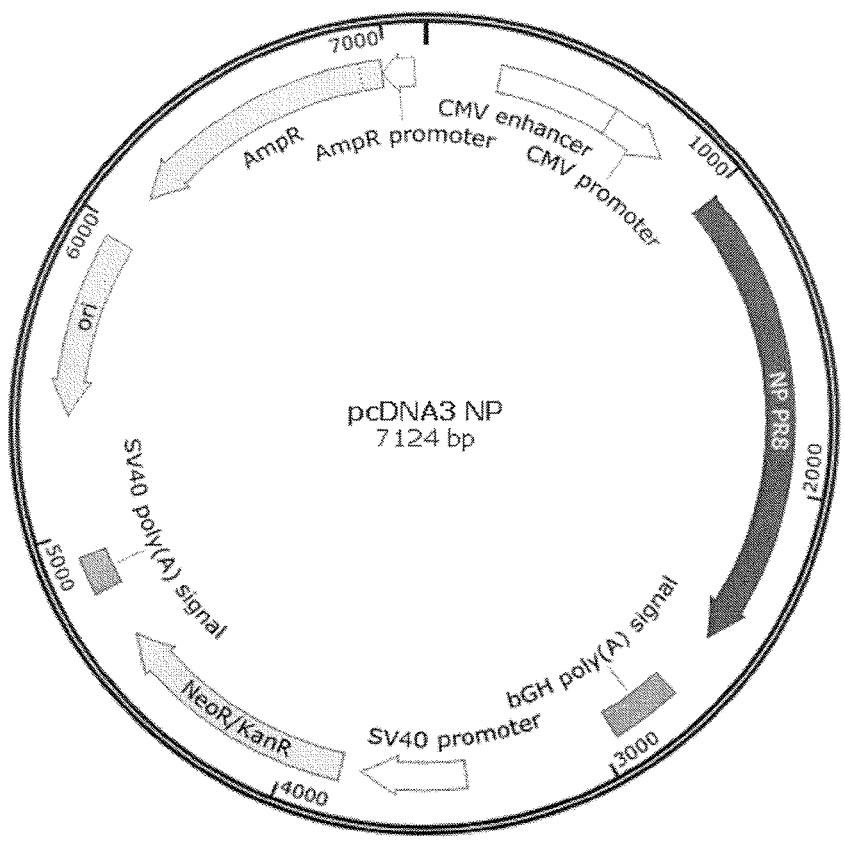
FIG. 10: map of the parental plasmid pcDNA3 NP—This plasmid and its derivatives, constructed as described in the Examples, were used for DNA vaccination.

11. Use of a Particular Fusion Protein IMX313T+Nucleoprotein (NP) Antigen from Influenza For DNA vaccinations, the parent plasmid pcDNA3-NP, as shown in FIG. 10, was modified as described in the example below.

11.1—Insertion of IMX313 into NP Encoding Plasmids

The IMX313 coding sequence was amplified from the plasmid pIMX494 using the oligonucleotide primers IMX1289 5' caatgcagaggagtacgacaatggatccaagaagcaaggtgatgctgatg 3' (SEQ ID NO 53) and IMX1290 5' GTAGAAACAAGGGTATTTTTCTTtattactccttgctcagtccttgc 3' (SEQ ID NO 54) and inserted into the plasmid pcDNA3-NP as described by Geiser (29).

11.2—Insertion of the tPA Signal Peptide

The tPA signal peptide was amplified from the vector pSG2-85A (28) using the oligonucleotides IMX1305 5' cactgagtgacatcaaaatcatgGATGCAATGAAGAGAGGGC 3' (SEQ ID NO 55) and IMX1306 5' cgtaagaccgtttggtgccttggctagctcttctgaatcgggcatggatttcc 3' (SEQ ID NO 56) and inserted in-frame with the N-terminus of the NP coding sequence in a number of plasmids as described by Geiser (29).

11.3—Creation of Two Point Mutations of NP to Render it Monomeric

The oligonucleotide primers IMX1287 5' ccattctgccgcatttgCagatctaagag 3' (SEQ ID NO 57) and IMX1288 5' CAAAAGGGAGATTTGCCTGTACTGAGAAC 3' (SEQ ID NO 58) were used to amplify an internal fragment of the NP gene, and the resulting PCR product was inserted into NP-encoding plasmids as described by Geiser. Because both oligonucleotides were imperfectly matched to the NP gene, the insertion of the PCR product generated two point mutations. The IMX1287 primer created the mutation E339A (GAA to GCA), whereas the IMX1288 primer created the mutation R416A in the NP gene (AGA to GCA).

11.4—Insertion of IMX313T

The IMX313T coding sequence was amplified from the plasmid pIMX497 using the oligonucleotide primers IMX1289 (SEQ ID NO 53) and IMX051 5' GTAGAAACAAGGGTATTTTTCTTtattaggagcgacggcgacgc 3' (SEQ ID NO 59) and inserted into the various pcDNA3-NP-derived plasmids as described by Geiser.

11.5—DNA Immunizations with the Nucleic Acids According to the Invention 11.5.1. Protocol Groups of five female BALB/C mice were immunized intramuscularly twice, 14 days apart, with various plasmid DNAs, using 20 g of each plasmid per injection. Immune responses were measured on day 28, to determine the influence of various modifications: +/– IMX313 or IMX313T; +/– the tPA signal peptide; +/– the monomerizing mutations.

Antigen-specific T-cell responses were measured by ELISPOTs, using splenocytes, on day 28. Purified spleen CD4+, CD8+ and Total T cells isolated from the immunized mice were co-cultured with NP A Influenza peptide (amino acids 366-374) purchased from Eurogentec. ELISPOT Assays: Flat-bottomed, 96-well nitrocellulose plates (Millititer; Millipore) were coated with IFN-γ mAb (15 µg/ml; MABTECH, Stockholm) and incubated overnight at 4° C. After washing with PBS, plates were blocked with 10% fetal bovine serum for one hour at 37° C. $2 \times 10^6$ cells per well were stimulated with relevant peptides at a final concentration of 2 µg/ml (NP A Influenza peptide) on IPVH-membranes coated with 15 g/ml anti-human IFN- and incubated for 20 hours. After incubation, the plates were washed thoroughly with PBS to remove cells, and IFN- mAb (1 g/ml of biotin, MABTECH) was added to each well. After incubation for 2 h at 37° C., plates were washed and developed with streptavidin-HRP (1 g/ml; MABTECH) for one hour at room temperature. After washing, the substrate (3-amino-9-ethycarbazol (Sigma)) was added and incubated for 15 minutes. After further washing, the red spots were counted under the microscope.

To study the humoral immune responses, we evaluated the antibody levels by ELISAs specific for total IgG, and separately for IgG1 and IgG2a to evaluate the relative proportions of Th1 and Th2 BALB/c mice typically respond to influenza vaccines with a Th2-type immune response, which is associated with the stimulation of IgG1 antibodies. However, the major antibody isotype present in the sera of mice that survive viral infections is IgG2a, which is stimulated during Th1-type immune responses (32). Stimulation of IgG2a antibodies has been associated with increased efficacy of influenza vaccination.

For the ELISAs, antigens were diluted to a concentration of 5 mg/ml in 0.1 M sodium carbonate/bicarbonate (pH 9.6) and were then used to coat the wells of MaxiSorb plates (Nunc-Immulon, Denmark). Twofold serial dilutions of the test sera were added to the wells, and following washing, bound antibodies were detected with anti-mouse IgG, or anti-mouse IgG1 or anti-mouse IgG2a (Sigma) conjugated to horseradish peroxidase. Absorbance at 490 nm was determined after o-phenylenediamine (Sigma) and $H_2O_2$ were added; the reactions were stopped with 1 M Sulphuric acid.

Results are shown in FIGS. 11 to 14.

11.5.2. In preliminary experiments, we tested the total T cells responses to NP induced by DNA vaccines encoding either NP or NP fused to IMX313. Total T cells isolated from the NP-IMX313 immunized mice showed significantly higher IFN responses compared with those of the NP immunized mice and confirmed the ability of IMX313 to increase T cell responses.

Figure 11:
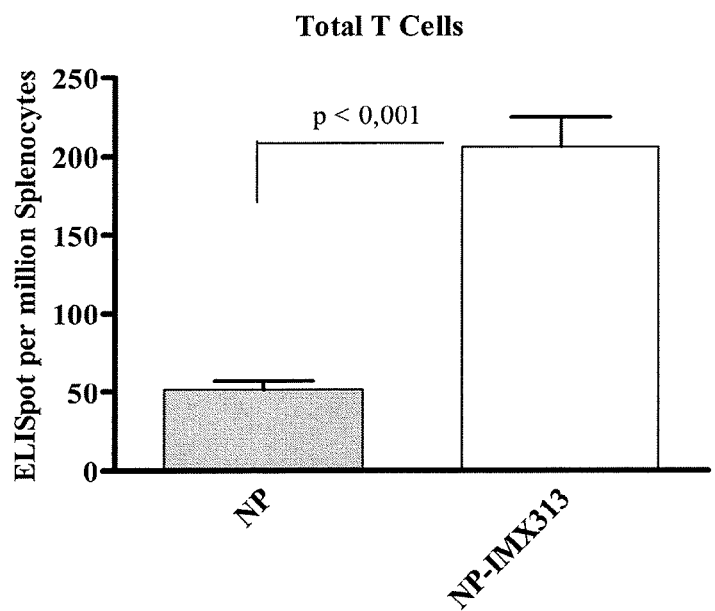
FIG. 11: Comparison of total T cells secreting IFN-γ in response to immunization with plasmids encoding NP, on NP fused to IMX313.

FIG. 11 shows that fusing the parental NP antigen gene to the IMX313 gene improves T cell responses to NP.

11.5.3. To determine whether the IFN- detected in the ELISPOTs was produced by CD4 or CD8 T cells, we purified spleen CD4+ and CD8+ T cells from the immunized mice, and these were co-cultured with an Influenza A NP peptide. A significant increase in IFN- production from CD8+ T cells was detected in the group immunized with NP-IMX313. The percentage of antigen-specific CD8+ cells producing IFN- was higher than the corresponding population of CD4+ T (FIG. 12).

Figure 12:
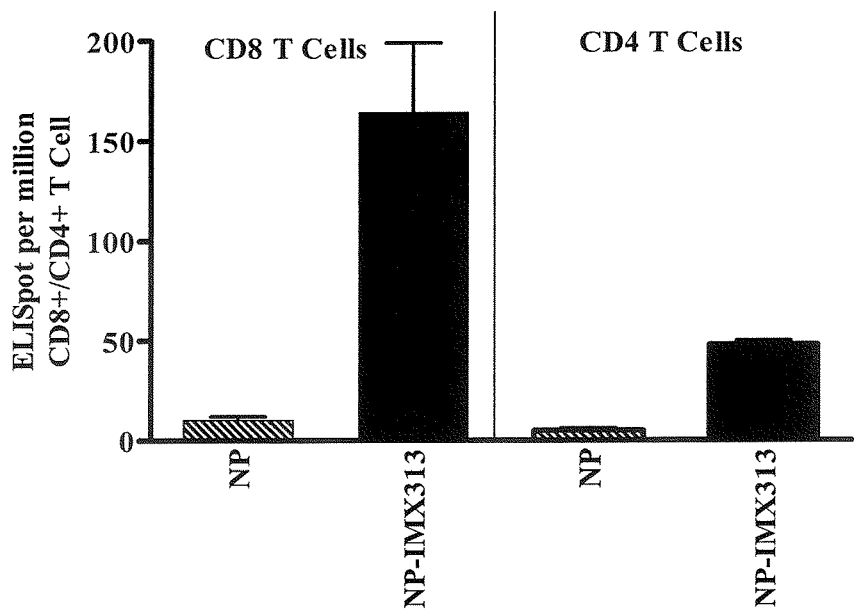
FIG. 12: Comparison of CD8 and CD4 T cells secreting IFN-γ in response to immunization with a plasmid encoding NP or a plasmid encoding NP fused to IMX313.

FIG. 12 shows that fusing the NP antigen gene to the IMX313 gene improves both CD4+ and CD8+ responses to the NP antigen.

11.5.4. We then examined the antibody response to NP after immunization and 14 days after the last immunization, NP-specific IgG Ab responses were measured in sera. NP control mice and mice given NP-IMX313 showed moderate NP-specific IgG Abs (FIG. 13), which were higher in the group immunized with NP-IMX313.

Figure 13:
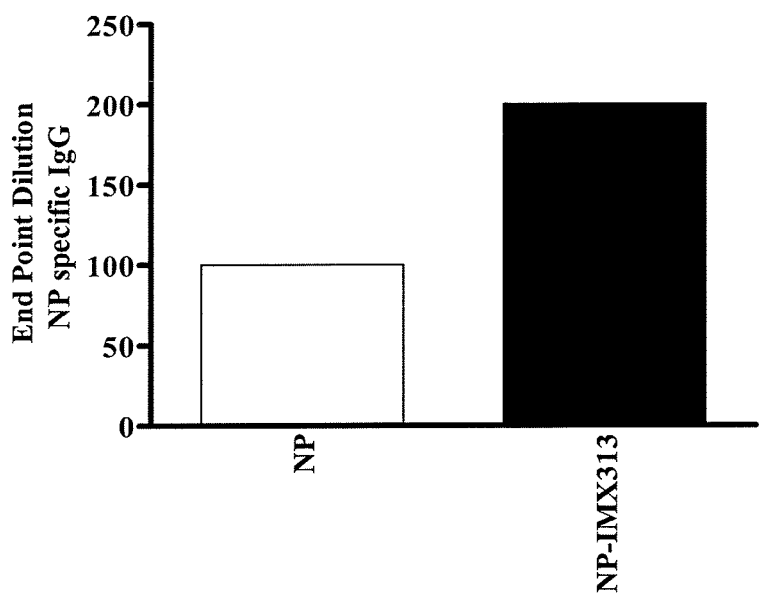
FIG. 13: Comparison of IgG antibody responses to recombinant NP induced by DNA plasmids encoding either NP or NP fused to IMX313

FIG. 13 shows that fusing the NP gene to the IMX313 gene improves IgG antibody responses to the NP antigen.

11.5.5. Sera were also examined for the presence of NP-specific IgG1 and IgG2a antibodies (representative of Th2 and Th1 types of response in Balb/C mice, respectively). NP-specific IgG1 and IgG2a antibody isotypes were detected in the sera of the NP-IMX313 immunized mice; however serum samples from mice given NP alone showed only low levels of IgG1 and IgG2a Ab (FIG. 14).

Figure 14:
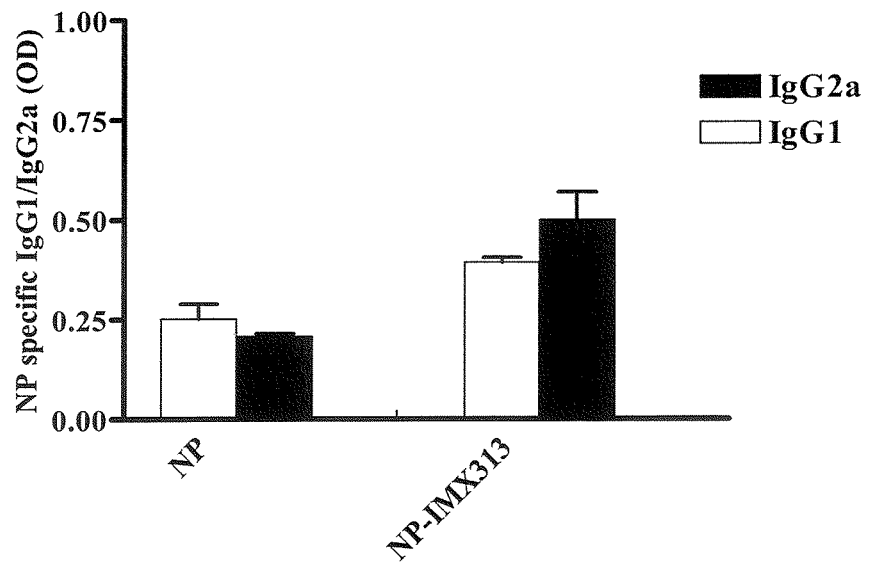
FIG. 14: Comparison of IgG antibody subclass responses to recombinant NP induced by DNA plasmids encoding either NP or NP fused to IMX313.

FIG. 14 shows the subclass distributions of the antibodies induced against the NP antigen. Fusion to the IMX313 gene improved the IgG2A response more than the IgG1 response, converting a Th2-biased response against NP to a Th1-biased response against NP-IMX313.

11.6—Production of Recombinant NP-M-IMX313T Protein

A synthetic gene encoding the protein NP-M-IMX313T was synthesized with codons optimized for expression in *Escherichia coli*. This synthetic gene was cloned into a T7-based expression vector pIMX04 (this is the vector pRsetC from Invitrogen in which the f1 origin has been replaced by the par locus of the plasmid pSC101). Expression was induced in several standard media (LB, Studier's Auto-Induction medium) and the overexpressed protein was purified initially as described by Ye (30) and by Tarus (31) for the clarification and ion-exchange steps, but in a final step the fusion protein was purified by affinity on Heparin Sepharose, as described above.

11.7. The Recombinant Protein NP-M-IMX313T is Used for Immunizations as Follows:

Groups of five female BALB/C mice are immunized intramuscularly twice, 14 days apart, with various protein preparations (with or without formulation with TLR ligands), using 2 nanomoles of protein per injection. Immune responses are measured on day 28, to determine antigen-specific T-cell responses, (measured by ELISPOTs), using splenocytes. Pre-immune and day 28 antibody responses were measured by ELISAs with NP as antigen.

Figure 15:
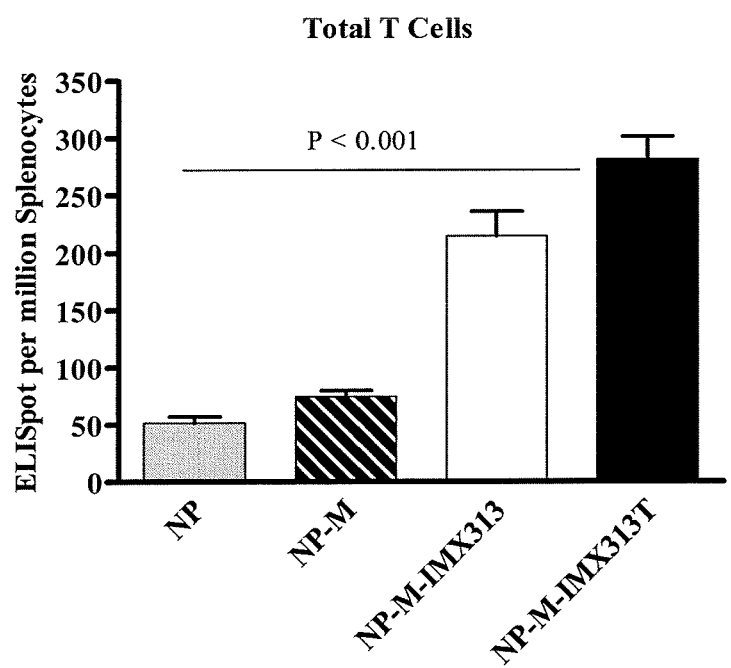
FIG. 15: Comparison of total T cell responses to plasmids encoding NP, monomeric NP (NP-M), monomeric NP fused to IMX313 (NP-M-IMX313) and monomeric NP fused to IMX313T (NP-M-IMX313T).

Results:

FIG. 15 shows that monomerisation of NP improves its immunogenicity slightly, that this is further improved by fusion to the IMX313 gene, but that the largest improvement is obtained by fusing the monomeric NP to the IMX313T gene.

Figure 16:
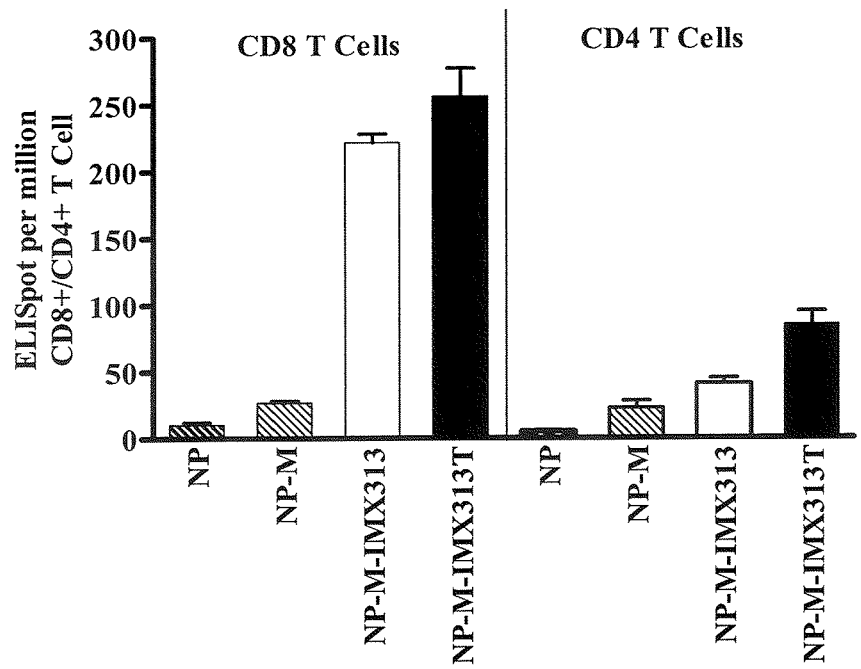
FIG. 16: Comparison of CD8+ and CD4+ T cell responses to plasmids encoding NP, monomeric NP (NP-M), monomeric NP fused to IMX313 (NP-M-IMX313) and monomeric NP fused to IMX313T (NP-M-IMX313T).

FIG. 16 shows that, on analysis of the CD4+ and CD8+ responses, the same rank ordering as in FIG. 6 is seen: monomerisation of NP improves NPs immunogenicity slightly; this is further improved by fusion to the IMX313 gene, but that the largest improvement is obtained by fusing the monomeric NP to the IMX313T gene.

Figure 17:
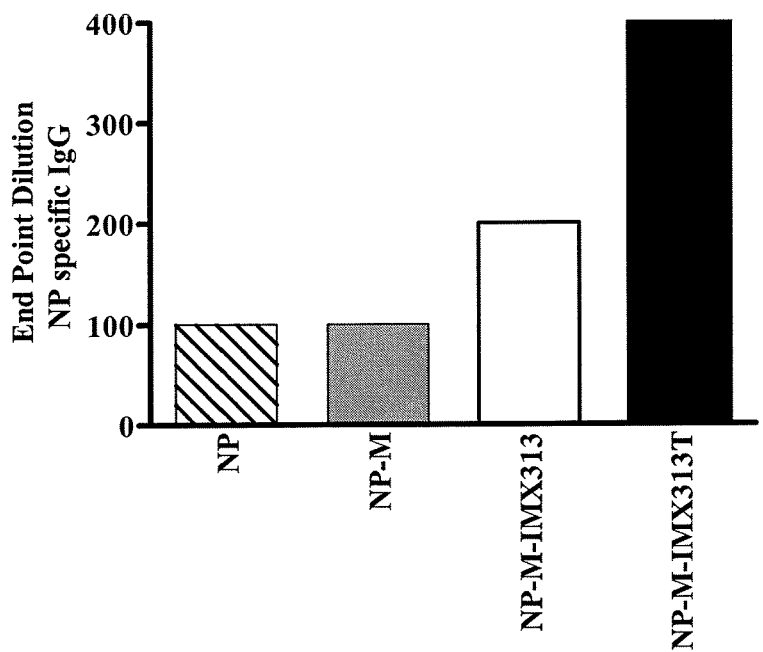
FIG. 17: Comparison of IgG antibody responses, measured by ELISA using recombinant NP, to plasmids encoding NP, monomeric NP (NP-M), monomeric NP fused to IMX313 and monomeric NP fused to IMX313T.

FIG. 17 shows that the same rank ordering is seen for B cell responses as was seen for T cell responses (both CD4+ and CD8+) in FIGS. 6 and 7. Total IgG responses against NP were higher with IMX313T than with IMX313.

Figure 18:
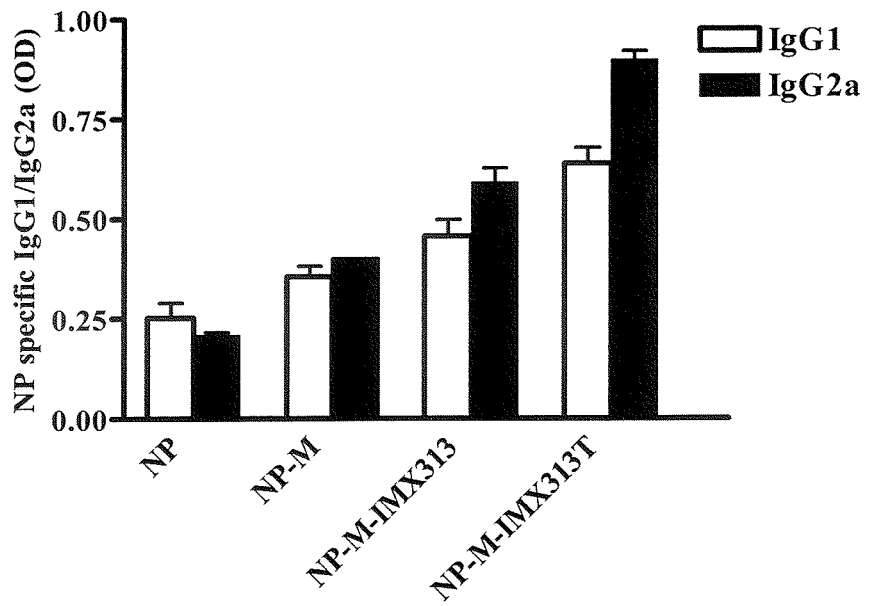
FIG. 18: Comparison of IgG antibody subclass responses, measured using recombinant NP, to plasmids encoding NP, monomeric NP (NP-M), monomeric NP fused to IMX313 and monomeric NP fused to IMX313T.

FIG. 18 shows the subclass distributions of the antibodies induced against the monomeric NP antigen. As with NP, fusion to the IMX313 gene augmented the IgG2A response more than the IgG1 response, converting a Th2-biased response against NP to a Th1-biased response against NP-IMX313. Of particular interest, this reversal of a Th2 to a Th1 bias was amplified by fusion to IMX313T rather than to IMX313. Expression of IgG2a antibodies in the influenza vaccines is a correlated with clearance of virus and increased protection against lethal influenza challenge. Increased induction of both antibody isotypes as measured by ELISA was a better correlate for vaccine efficacy than neutralization alone (32).

11.8—Secretion of the NP Antigen Improved its Immunogenicity

A series of NP DNA vaccine constructs containing the tissue plasminogen activator (tPA) secretory signal sequence was made: tPA-NP, tPA-NP-M, tPA-NP-M-IMX313, and tPA-NP-M-IMX313T. The effects of the fusion of tPA to NP on the humoral and cellular immune responses from the immunized animals were analyzed.

Mice immunized with tPA containing constructs showed significantly higher IFN responses compared with those of the NP immunized mice and confirmed the ability of IMX313T and the monomerizing mutations to increase T cell responses.

Figure 19:
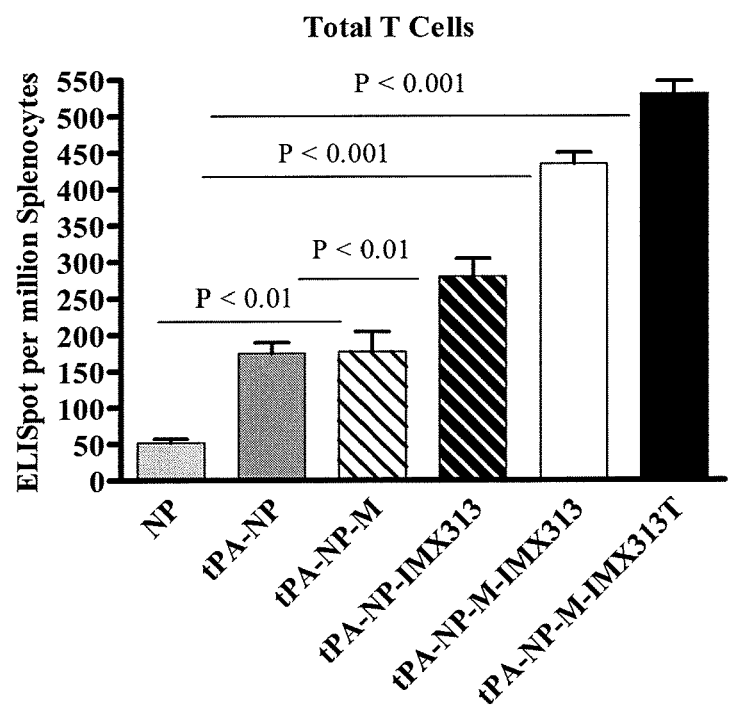
FIG. 19: Influence of the secretion, by the tPA signal peptide, of the various NP fusion proteins. Total T cells were measured by IFNγ ELISpots comparing NP, secreted NP (tPA-NP), secreted monomeric NP (tPA-NP-M), secreted NP fused to IMX313 (tPA-NP-IMX313), secreted monomeric NP fused to IMX313, and secreted monomeric NP fused to IMX313T (tPA-NP-M-IMX313T).

FIG. 19 shows that forcing the secretion of the NP antigen improved its immunogenicity (NP versus tPA-NP), whether it was monomeric or not (tPA-NP versus tPA-NP-M). However, fusion to IMX313 showed that use of a monomeric version of NP was more immunogenic than use of the unmodified antigen (tPA-NP-IMX313 versus tPA-NP-M-IMX313). And substitution of IMX313 by IMX313T further improved the immunogenicity of NP (tPA-NP-M-IMX313 versus tPA-NP-M-IMX313T).

Figure 20:
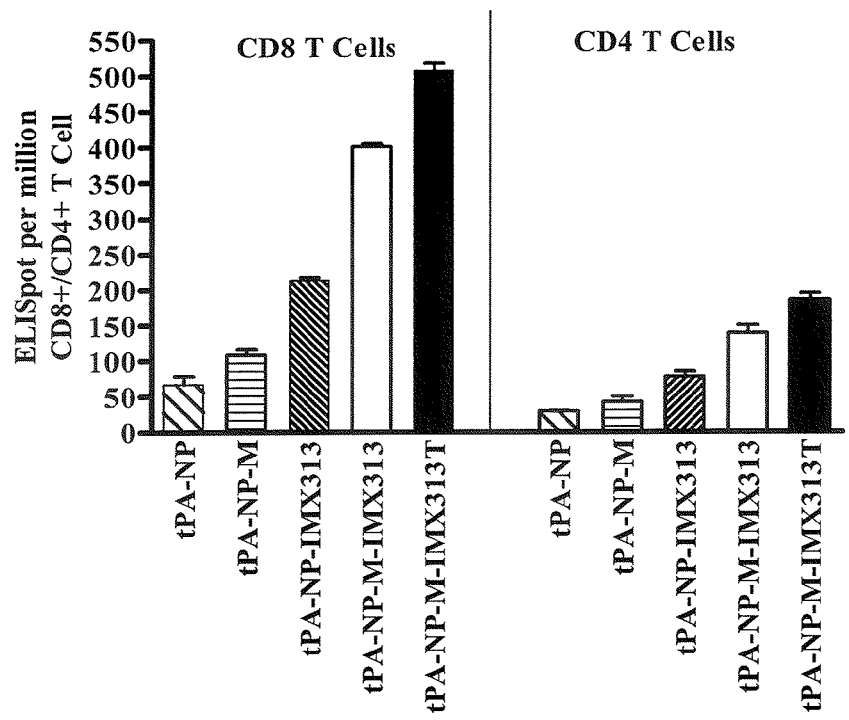
FIG. 20: Influence of the secretion, by the tPA signal peptide, on the CD8+ and CD4+ responses to various NP fusion proteins, measured by IFNγ ELISpots comparing: NP, secreted NP (tPA-NP), secreted monomeric NP (tPA-NP-M), secreted NP fused to IMX313 (tPA-NP-IMX313), secreted monomeric NP fused to IMX313, and secreted monomeric NP fused to IMX313T (tPA-NP-M-IMX313T).

FIG. 20 shows the CD8+ and CD4+ responses to the different secreted versions of NP. The same rank ordering as in FIG. 19 is seen, and the utility of monomerising the antigen is once again pronounced when IMX313 is added. As in the preceding figures, the largest immune responses are seen when IMX313T is used rather than IMX313.

Figure 21:
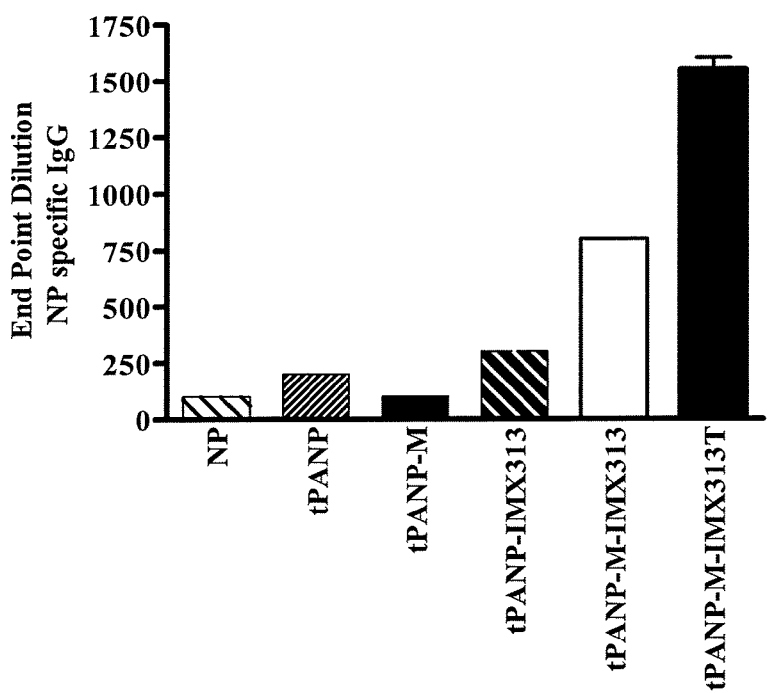
FIG. 21: Influence of the secretion, by the tPA signal peptide, of the IgG responses to various NP fusion proteins, measured by ELISAs comparing: NP, secreted NP (tPA-NP), secreted monomeric NP (tPA-NP-M), secreted NP fused to IMX313 (tPA-NP-IMX313), secreted monomeric NP fused to IMX313, and secreted monomeric NP fused to IMX313T (tPA-NP-M-IMX313T).

FIG. 21 shows the total IgG responses to the antigen NP and invites the same conclusions as FIG. 20 for T cell responses: the largest responses are seen when IMX313T is used, but secretion (NP versus tPA-NP) and monomerisation (tPA-NP-IMX313 versus tPA-NP-M-IMX313) are also important contributions.

Mice immunized with NP alone had no or very low levels of anti-NP IgG antibody in their sera (FIG. 21) Mice immunized with NP-M-IMX313, tPA-NP-M-IMX313, NP-M-IMX313T or tPA-NP-M-IMX313T on the other hand, showed high levels of systemic NP-specific IgG antibody responses; however, the tPA-NP-M-IMX313T immunized mice had significantly higher (p<0.001) IgG antibody responses compared to all the groups of immunized mice. This shows that the combination of all the modifications (monomerizing mutations, tPA and IMX313T) confers a significantly improved immunogenicity to the antigen compared to the parental sequence or other combinations.

Figure 22:
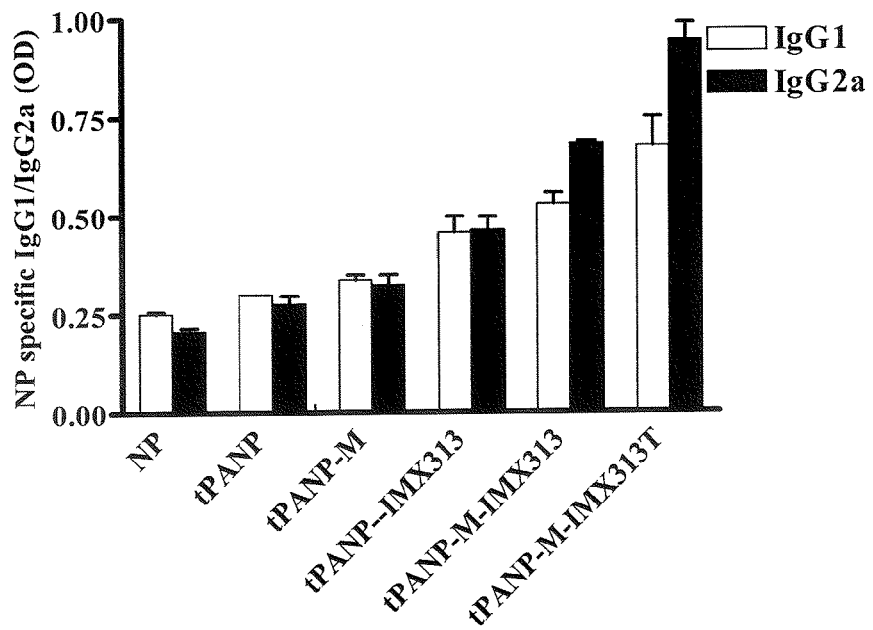
FIG. 22: Influence of the secretion, by the tPA signal peptide, on the IgG subclass responses to various NP fusion proteins, measured by ELISAs comparing: NP, secreted NP (tPA-NP), secreted monomeric NP (tPA-NP-M), secreted NP fused to IMX313 (tPA-NP-IMX313), secreted monomeric NP fused to IMX313, and secreted monomeric NP fused to IMX313T (tPA-NP-M-IMX313T).
Figure 23:
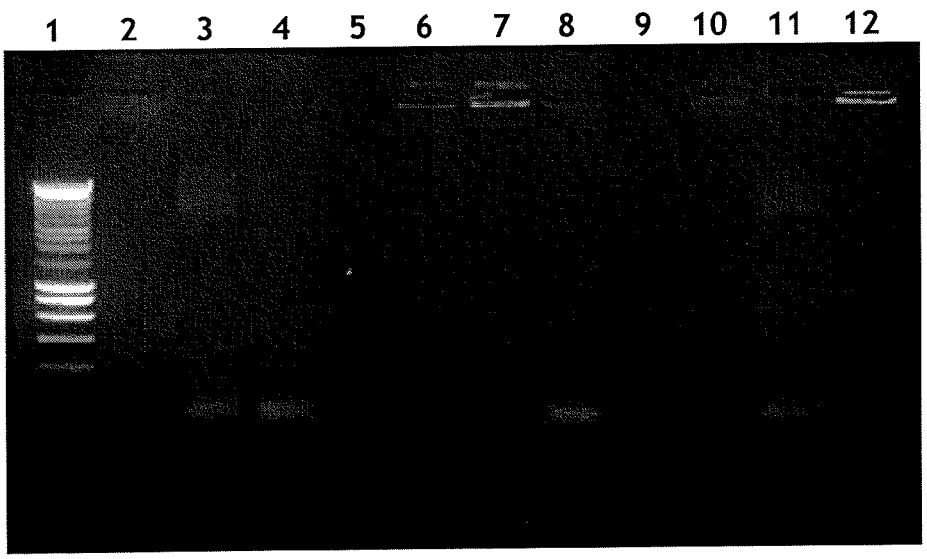
FIG. 23: This figure shows that the IMX743 protein binds a DNA oligonucleotide ODN1826 strongly, whereas the IMX744 binds only weakly to the same oligonucleotide. Agarose gel electrophoresis was carried out in 0.8% in TAE buffer. The position in the gel to which the oligonucleotide migrated is observable under ultraviolet light when the gel is stained with ethidium bromide. Different combinations of the TLR9 ligand ODN1826 and the IMX744 and IMX743 proteins were prepared, as described in the Table above the gel, and complex formation was analyzed by agarose gel electrophoresis. Complex formation was clearly detectable because the complexes migrated much more slowly than the uncomplexed ligand. As the concentration of the protein was decreased, the observed complexes became more diffuse, and a band of unbound TLR ligand became visible. The gel shows that the gel shift is reproducible with IMX743 (compare lanes 6 and 12), but that IMX744 (lanes 3-5) produces a shift that is almost imperceptible in the gel.

FIG. 22 shows the subclass analysis of the B cell responses to NP, and illustrates that the initial Th2 bias with NP alone is reversed by IMX313 and by IMX313T. While secretion has little effect on its own (NP versus tPA-NP), monomerisation (tPA-NP-IMX313 versus tPA-NP-M-IMX313) and then the replacement of IMX313 by IMX313T (tPA-NP-M-IMX313 versus tPA-NP-M-IMX313T) all contribute to the improved Th1 (IgG2a) versus Th2 (IgG1) responses. It is very important that tPA-NP-M-IMX313T on its own improves almost equivalently Th1 and Th2 responses. Fusion of NP to IMX313 shows that both Th1 and Th2 responses are both increased, and there is no significant shift in the type of response. But with IMX313T and the monomerizing mutations, the Th1 response (IgG2a) starts to predominate. The consensus among immunologists is that Th1 responses are preferable to Th2 responses (FIG. 22).

11.9—IMX313T is Not Degraded by Proteases on Passage Through Secretion Pathways

The results obtained by DNA immunizations with plasmids containing IMX313T strongly suggest that the tail of the molecule is not cleaved by proteases as it passes through the secretion pathway, where proteases are abundant. To examine this question more directly, transfection of CHO K1 cells was undertaken with the plasmid used to express NP-M-IMX313T in vivo. The transfection was carried out as described (33).

Eighteen to twenty-four hours later, the supernatants of the transfected cells was recovered by centrifugation, and filtered before being loaded onto a Heparin Sepharose column, as described above.

A small "peak C" was seen which proved on SDS-PAGE and Western Blotting to contain the protein NP-M-IMX313T.

12 Modification of a Trimeric Coiled Coil

To determine whether modification of a trimeric coiled coil could improve the immunogenicity of the antigen, two plasmids were constructed using a synthetic HA2 gene encoding the trimeric coiled coil of the influenza hemagglutinin.

The first plasmid was pIMX743, in which the HA2 coiled coil was modified by the fusion of a peptide: SPRRRRRRRRRS (SEQ ID NO 37)

The following Nde I to HindIII restriction fragment was cloned in a T7 expression vector:

```
                                         (SEQ ID NO 60)
CATATGCGGGGTTCTCATCATCATCATCATCATCATCATGGTAGTG

GTTATGCAGCCGATCAGAAAAGCACGCAAAATGCGATTAACGGCAT

TACCAACAAAGTCAATTCTGTGATCGAAAAGATGAATATCCAGTTT

ACTGCTGTAGGCAAAGAGTTCAACAAACTGGAGAAACGCATGGAAA

ACCTGAACAAGAAAGTGGATGATGGGTTTCTGGATATTTGGACCTA

TAACGCGGAATTACTTGTGCTCTTAGAAAACGAACGGACATTGGAC

TTCCATGATTCGAACGTCAAGAACCTGTATGAGAAAGTGAAAAGCC

AGCTGAAGAACAATGCCTCACCACGTCGCCGTCGTCGCCGTCGCCG

TCGCAGTTAATAAGCTT
```

The encoded protein sequence was:

```
                                         (SEQ ID NO 61)
MRGSHHHHHHHHGSGYAADQKSTQNAINGITNKVNSVIEKMNIQFT

AVGKEFNKLEKRMENLNKKVDDGFLDIWTYNAELLVLLENERTLDF

HDSNVKNLYEKVKSQLKNNASPRRRRRRRRRS**
```

The control plasmid pIMX744 was created by deleting the peptide using the oligonucleotide primers IMX203:5' GTTAGCAGCCGGATCAAGCTTATTAG-GCATTGTTCTTCAGCTGGC 3' (SEQ ID NO 62) and T7F to amplify the HA2 insert which was then reinserted into the parental plasmid.

The nucleotide sequence was:

```
                                         (SEQ ID NO 63)
CATATGCGGGGTTCTCATCATCATCATCATCATCATGGTAGTGGTTATG

CAGCCGATCAGAAAAGCACGCAAAATGCGATTAACGGCATTACCAA

CAAAGTCAATTCTGTGATCGAAAAGATGAATATCCAGTTTACTGCT

GTAGGCAAAGAGTTCAACAAACTGGAGAAACGCATGGAAACCTGA

ACAAGAAAGTGGATGATGGGTTTCTGGATATTTGGACCTATAACGC

GGAATTACTTGTGCTCTTAGAAAACGAACGGACATTGGACTTCCAT
```

-continued
```
GATTCGAACGTCAAGAACCTGTATGAGAAAGTGAAAAGCCAGCTGA

AGAACAATGCCTAATAAGCTT
```

And the encoded protein sequence was:

```
                                        (SEQ ID NO 64)
MRGSHHHHHHGSGYAADQKSTQNAINGITNKVNSVIEKMNIQFTAV

GKEFNKLEKRMENLNKKVDDGFLDIWTYNAELLVLLENERTLDFHD

SNVKNLYEKVKSQLKNNA**
```

Both proteins were then purified first on an IMAC affinity column, and then on a heparin Sepharose column. The IMX743 protein eluted at a higher salt (NaCl) concentration than the IMX744 protein: the IMX743 protein eluted at a salt concentration of 1.4 M (sic) whereas the IMX744 protein eluted at a salt concentration of 600 mM.

Both proteins were then used to immunize four groups of 5-6 week old female BALB/c mice, on days 0 and 14, with 20 µg per injection. Sera and spleens were collected for ELISAs and ELISPOTs on day 21. Two groups received the protein in the adjuvant Addavax, while the other two groups were immunized without an adjuvant. The protein IMX744 was used as the ELISA antigen, and also to stimulate the splenic cells.

The results are shown in Table 4 below:

| Immunogen | Adjuvant | IgG Response Serial Dilution | Th Pattern | Cellular Response INFγ ELISPOT ($\times 10^6$ Splenocytes) |
|---|---|---|---|---|
| 744 | none | 100 | Th2 | 115 |
| 744 | MF59 | 900 | Th1 = Th2 | 417 |
| 743 | none | 500 | Th1 | 305 |
| 743 | MF59 | 8000 | Th1 | 733 |

The results clearly show that the positively charged peptide (SEQ ID NO 37),—present only in the IMX743 protein—, makes the IMX743 protein much more immunogenic than the otherwise identical protein IMX744, whether an adjuvant is used or not. Furthermore, the use of an adjuvant further improves the immunogenicity of the coiled coil containing antigen.

13. Modification of the Murine C4bp Oligomerisation Domain IMX108

The coiled coil of the fusion protein DsbA-IMX108, described in reference 16, was modified to determine whether it too acquired improved properties conferred on IMX313. To modify it, the DsbA-IMX108 gene was amplified with the oligonucleotide IMX212: 5' GGAGCGACGGCGACGCG-GAGActggagctgtagtagttcaacctcc 3' (SEQ ID NO 65) and T7F, and inserted (29) into the plasmid expressing IMX313T, in place of IMX313. The protein was purified by ion-exchange chromatography, and then on a heparin-Sepharose column, to which it bound, whereas the parental construct DsbA-IMX108 did not.

The parental IMX108 sequence (SEQ ID NO 66) is aligned here to the IMX108T sequence (SEQ ID NO 67);

```
IMX108:
EASEDLKPALTGNKTMQYVPNSHDVKMALEIYKLTLEVELLQLQIQ
KEKHTEAH*
```

```
IMX108T:
EASEDLKPALTGNKTMQYVPNSHDVKMALEIYKLTLEVELLQLQSP
RRRRS*
```

The modified IMX108 protein is useful for immunizing poultry, where potential auto-immune effects of using modified IMX313 fusion proteins should be avoided (16). Other mammalian C4bp oligomerisation domains (listed in reference 16, and WO 2007/062819) can also be modified as described herein for this purpose.

14. Fusion Proteins Comprising the N-Terminus of *Staphylococcal* Hemolysin Alpha and Modified IMX313 Proteins To demonstrate that fusion to the modified IMX313 proteins could improve the immunogenicity of the N-terminal domain of the *staphylococcal* toxin hemolysin alpha (Hla), the truncated hemolysin gene was amplified from genomic DNA of the Newman strain and cloned into a T7 expression vector. The oligonucleotides used were:

```
IMX056:
                                        (SEQ ID NO 68)
5' GTTTAACTTTAAGAAGGAGATATAcatatggcagattctgata
ttaatattaaaaccgg 3'
and IMX057:
                                        (SEQ ID NO 69)
5' GTTAGCAGCCGGATCAAGCTTATTAatcgattttatatctttc
tgaagaacgatctgtc 3'.
```

To fuse the N-terminal sixty-three amino acids of the mature toxin to a modified IMX313 protein, IMX313T was amplified with the primers:

IMX110: 5' AGAACGAAAGGTACCATTGCTGGATC-CAAGAAGCAAGGTGATGCT 3' (SEQ ID NO 70) and IMX139: 5' GGGCGATCGGTGCGGGCCTCTTCGC 3' (SEQ ID NO 44) from the IMX313T expression plasmid and the PCR product was used to truncate further the Hla toxin gene, while fusing amino acid 63 to the modified IMX313 gene. The resulting plasmid expresses the fusion protein, called Hla63-IMX313T, which has the following protein sequence:

ADSDINIKTGTTDIGSNTTVKTGDLVTY-DKENGMHKKVFYSFIDDKNHNKKLLVIRTKG TIAG-SKKQGDADVCGEVAYIQSVVSDCHVP-TAELRTLLEIRKLFLEIQKLKVELQSPRRR RS (SEQ ID NO 71) and is encoded by the following nucleotide sequence:

```
                                        (SEQ ID NO 72)
ATGGCAGATTCTGATATTAATATTAAAACCGGTACTACAGATATTG

GAAGCAATACTACAGTAAAAACAGGTGATTTAGTCACTTATGATAA

AGAAAATGGCATGCACAAAAAAGTATTTTATAGTTTTATCGATGAT

AAAAATCATAATAAAAAACTGCTAGTTATTAGAACGAAAGGTACCA

TTGCTGGATCCAAGAAGCAAGGTGATGCTGATGTGTGCGGAGAGGT

TGCTTATATTCAGAGCGTCGTCTCCGATTGCCACGTGCCTACAGCG

GAACTGCGTACTCTGCTGGAAATACGAAAACTCTTCCTGGAGATTC

AAAAACTGAAGGTGGAACTGCAGTCTCCGCGTCGCCGTCGCTCCTA

A.
```

To produce this protein, a 500 ml culture of the strain C43(DE3) was induced with 1 mM IPTG and grown overnight. The harvested bacteria were lysed by sonication, and the insoluble protein was resuspended in 50 mM Tris pH 7.5, 150 mM NaCl and 6 M Urea (buffer A). This was loaded onto a Hi-Trap SP FF column, and eluted with Buffer A containing 1 M NaCl. The partially purified protein was dialyzed against the buffer 50 mM Tris pH 7.5, 150 mM NaCl, and loaded onto a Heparin Sepharose column, from which it was eluted with an NaCl gradient (50 mM Tris pH 7.5, 1 M NaCl). The eluted protein was dialyzed against PBS and further purified by gel filtration.

The N-terminal fragment (lacking IMX313T) was modified by cloning a C-terminal 6 His tag, and purified by IMAC Nickel affinity chromatography and gel filtration.

Both purified proteins were then used to immunize mice, in the presence and absence of an adjuvant.

Four groups of five female BALB/c mice aged 5-6 weeks were immunised with 5 mmoles of either the Hla63 protein or the same antigen fused to IMX313T on days 0 & 14. On day 28, sera and spleens were collected for ELISAs and ELISPOTs. The protein 63 Hla 6 His was used as the ELISA antigen, and also to stimulate the splenic cells.

The results are shown in Table 5:

| Immunogen | Adjuvant | IgG Response Serial Dilution | Cellular Response INFγ ELISPOT ($\times 10^6$ Splenocytes) |
|---|---|---|---|
| 63 HLA | None | — | 17 |
| 63 HLA | ISA 51 | 100 | 68 |
| 63 HLA-IMX313T | none | 100 | 47 |
| 63 HLA-IMX313T | ISA 51 | 600 | 128 |

The results clearly show that the N-terminus of hemolysin alpha (HLA) is more immunogenic when fused to the IMX313T protein, whether an adjuvant is used or not.

15. Full Length *Staphylococcal* Protein A Fused to Modified IMX313 Proteins

To determine whether IMX313T and IMX313P could improve the immunogenicity of the full-length *Staphylococcal* protein A antigen (SpA), a synthetic gene encoding the five homologous domains (mutated as described in reference 44) was cloned as an Nde I-Hind III fragment in a T7 expression vector. The nucleotide sequence was as follows:

```
                                        (SEQ ID NO 73)
CATATGGCGCAACACGATGAAGCTCAAGCGAATGCATTCTACCAGG

TTCTGAACATGCCGAATTTGAATGCGGACCAACGTAATGGCTTTAT

TCAATCCCTGAAGGACGCACCGTCCCAAAGCGCAAACGTTCTGGGT

GAAGCGCAAAAACTGAATGATAGCCAGGCCCCGAAAGCCGATGCCC

AGCAGAACAAGTTCAATAAGGATCAGGCCTCTGCGTTCTATGAGAT

TTTGAATATGCCGAACTTGAATGAGGAGCAACGCAACGGCTTTATC

CAAAGCCTGAAAGATGCACCAAGCCAAAGCACGAACGTTCCTGGGTG

AGGCAAAGAAACTGAACGAGAGCCAGGCGCCGAAAGCGGACAACAA

TTTCAATAAAGAGCAAGCGAACGCCTTTTACGAAATTCTGAATATG

CCTAACCTGAACGAAGAACAACGTAACGGCTTCATCCAGAGCTTGA

AGGACGCGCCGTCGCAAAGCGCGAATCTGCTGGCCGAGGCGAAAAA

GCTGAATGAGAGCCAAGCGCCGAAGGCGGACAATAAGTTTAACAAA

GAACAGGCGAACGCATTCTATGAAATCCTGCATCTGCCGAATCTGA

ATGAAGAACAGCGCAATGGTTTTATCCAGAGCCTGAAGGATGCGCC

AAGCCAGAGCGCAAACCTGTTGGCTGAGGCCAAGAAGCTGAACGAT

GCGCAGGCTCCGAAAGCTGACAACAAATTCAACAAAGAGCAGGCCA

ACGCTTTTTACGAGATTCTGCACTTGCCGAACCTGACCGAAGAACA

GCGTAATGGTTTCATCCAGTCTCTGAAAGACGCACCGAGCGTGAGC

AAAGAGATTCTGGCAGAGGCGAAGAAGTTGAACGACGCGCAGGCAC

CGAAAGGATCCCATCACCACCACCATCACTAATAAGCTT
```

And the encoded protein sequence was:

```
                                        (SEQ ID NO 74)
MAQHDEAQANAFYQVLNMPNLNADQRNGFIQSLKDAPSQSANVLGE

AQKLNDSQAPKADAQQNKFNKDQASAFYEILNMPNLNEEQRNGFIQ

SLKDAPSQSTNVLGEAKKLNESQAPKADNNFNKEQANAFYEILNMP

NLNEEQRNGFIQSLKDAPSQSANLLAEAKKLNESQAPKADNKFNKE

QANAFYEILHLPNLNEEQRNGFIQSLKDAPSQSANLLAEAKKLNDA

QAPKADNKFNKEQANAFYEILHLPNLTEEQRNGFIQSLKDAPSVSK

EILAEAKKLNDAQAPKGSHHHHHH*
```

To fuse the antigen to the IMX313T and IMX313P proteins, the BamH I-Hind III fragment encoding the C-terminal His tag was replaced by BamH I-Hind III fragments encoding the 313 proteins.

Proteins were purified as follows: SpA-6His was produced in the bacterial strain BLR, and the bacterial pellet was lysed in buffer A (1× PBS, 1M NaCl, 20 mM Imidazole, 1 mM PMSF), the bacterial lysate was heated to 75° C. for 15 minutes, and then clarified by centrifugation before being loaded on an IMAC Nickel affinity column. The protein was eluted with a gradient of Imidazole in buffer B (1× PBS, 500 mM Imidazole). The protein was further purified by gel filtration.

SpA-IMX313T and SpA-IMX313P were also expressed in the strain BLR, and the bacterial lysates were heated to 75° C. for 15 minutes, and clarified by centrifugation. Both proteins were then purified on an SP ion exchange column, and then on a heparin Sepharose column.

These three proteins were used to immunize six groups of 5-6 week old Balb/c female mice on days 0 & 14. 5 mmoles of each protein was used per immunisation, with or without the adjuvant AddaVax. On day 28, sera and spleens were collected for ELISAs and ELISPOTs. The SpA-6His protein was used as the ELISA antigen, and also to stimulate the splenic cells.

The results are shown in table 6 below. The antigen SpA fused to IMX313T or P is clearly more immunogenic than the unfused antigen, and the IMX313P version is slightly more immunogenic than the IMX313T version.

TABLE 6

| Immunogen | Adjuvant | IgG Response Serial Dilution | Th pattern | Cellular Response INFγ ELISPOT ($\times 10^6$ Splenocytes) |
|---|---|---|---|---|
| SpA | None | 100 | Th1 = Th2 | 15 |
| SpA | AddaVax | 1,300 | Th1 = Th2 | 29 |

TABLE 6-continued

| Immunogen | Adjuvant | IgG Response Serial Dilution | Th pattern | Cellular Response INFγ ELISPOT (×10⁶ Splenocytes) |
|---|---|---|---|---|
| SpA-IMX313T | None | 1,200 | Th1 | 77 |
| SpA-IMX313T | AddaVax | 7,800 | Th1 | 150 |
| SpA-IMX313P | None | 2,700 | Th1 | 117 |
| SpA-IMX313P | AddaVax | 12,800 | Th1 | 207 |

16. Fusion Proteins of ClfB and Modified IMX313 Proteins

To improve the immunogenicity of the *Staphylococcal* antigen ClfB, the N2N3 domains was amplified with the following oligos:

IMX239:
(SEQ ID NO 75)
5' CATCATCATCATCATCACggtGCTGAACCGGTAGTAAATGCTG
CTGATGCTAAAGG 3'
and IMX240:  5'  ccccaaggggttatgctagttaATT-TACTGCTGAATCACCATCagcacttccaccacc 3' (SEQ ID NO 76) and the PCR product was cloned into a T7 expression vector with an N-terminal His tag (27).

The nucleotide sequence of the N2N3 fragment is:

(SEQ ID NO 77)
ATGCGGGGTTCTCATCATCATCATCATCATCATGGTgctgaac cggtagtaaatgctgctgatgctaaaggtacaaatgtaaatgataa agttacggcaagtaatttcaagttagaaaagactacatttgaccct aatcaaagtggtaacacatttatggcggcaaattttacagtgacag ataaagtgaaatcaggggattattttacagcgaagttaccagatag tttaactggtaatggagacgtggattattctaattcaaataatacg atgccaattgcagacattaaaagtacgaatggcgatgttgtagcta aagcaacatatgatatcttgactaagacgtatacatttgtctttac agattatgtaaataataaagaaaatattaacggacaattttcatta cctttatttacagaccgagcaaaggcacctaaatcaggaacatatg atgcgaatattaatattgcggatgaaatgtttaataataaaattac ttataactatagttcgccaattgcaggaattgataaaccaaatggc gcgaacatttcttctcaaattattggtgtagatacagcttcaggtc aaaacacatacaagcaaacagtatttgttaaccctaagcaacgagt tttaggtaatacgtgggtgtatattaaaggctaccaagataaaatc gaagaaagtagcggtaaagtaagtgctacagatacaaaactgagaa ttttgaagtgaatgatacatctaaattatcagatagctactatgc agatccaaatgactctaaccttaaagaagtaacagaccaatttaaa aatagaatctattatgagcatccaaatgtagctagtattaaatttg gtgatattactaaaacatatgtagtattagtagaagggcattacga caatacaggtaagaacttaaaaactcaggttattcaagaaaatgtt gatcctgtaacaaatagagactacagtattttcggttggaataatg agaatgttgtacgttatggtggtggaagtgctgatggtgattcagc agtaaattaa and the protein sequence is:
(SEQ ID NO 78)
MRGSHHHHHHHHGAEPVVNAADAKGTNVNDKVTASNFKLEKTTFDP

NQSGNTFMAANFTVTDKVKSGDYFTAKLPDSLTGNGDVDYSNSNNT

MPIADIKSTNGDVVAKATYDILTKTYTFVFTDYVNNKENINGQFSL

PLFTDRAKAPKSGTYDANINIADEMFNNKITYNYSSPIAGIDKPNG

ANISSQIIGVDTASGQNTYKQTVFVNPKQRVLGNTWVYIKGYQDKI

EESSGKVSATDTKLRIFEVNDTSKLSDSYYADPNDSNLKEVTDQFK

NRIYYEHPNVASIKFGDITKTYVVLVEGHYDNTGKNLKTQVIQENV

DPVTNRDYSIFGWNNENVVRYGGGSADGDSAVN*

Subsequently, the IMX313T and IMX313P domains were amplified with the oligonucleotides:
IMX248:  5'  gctgatggtgattcagcagtaaatg-gatccaagaagcaaggtgatgctgatg 3' (SEQ ID NO 79) and IMX139 and cloned C-terminal to the N3 domain. The unmodified N2N3 domains, and the fusion proteins N2N3-IMX313T and IMX313P are expressed as follows:

500 ml cultures of the strain C43(DE3) were induced with 1 mM IPTG and after overnight induction, the bacterial pellets was lysed in buffer A (1×PBS, 1M NaCl, 20 mM Imidazole, 1 mM PMSF), and then clarified by centrifugation before being loaded on an IMAC Nickel affinity column. The protein was eluted with a gradient of Imidazole in buffer B (1×PBS, 500 mM Imidazole). The fusion proteins are further purified by affinity chromatography on Heparin-Sepharose, followed by Sephacryl S-300 HR gel filtration, while the unfused protein is further purified by gel filtration on an S-75 gel filtration column.

17. Fusion Proteins of Sortase A and Modified IMX313 Proteins

To improve the immunogenicity of the *Staphylococcal* protease known as sortase A, or SrtA, an inactivated version was cloned in frame to IMX313, IMX313T and IMX313P as follows: the wild type sortase A gene was amplified from Newman strain genomic DNA with the oligonucleotides
IMX005  5'  GTTTAACTTTAAGAAGGAGATATA-CATatgCAAGCTAAACCTCAAATTCC 3' (SEQ ID NO 80) and
IMX1275  5'  GTTAGCAGCCGGATCAAGCTTAT-TATTTGACTTCTGTAGCTACAA 3' (SEQ ID NO 81) and cloned into a T7 expression vector. The active site cysteine residue was then mutated to serine with the oligonucleotide IMX215:  5'  GATAAACAATTAACATTAATTACTTCT-GATGATTACAATGAAAAGACAGGCG 3' (SEQ ID NO 82).

The IMX313, 313T and 313P genes were then amplified with the oligonucleotides IMX006: 5' TTGTAGCTACA-GAAGTCAAAAAGAAGCAAGGTGATGCTGATG 3' (SEQ ID NO 83) and IMX139: 5' GGGCGATCGGT-GCGGGCCTCTTCGC 3' (SEQ ID NO 44) from their respective expression vectors, and inserted in-frame with the inactivated protease gene (29).

The IMX313T and IMX313P fusion proteins were purified by ion-exchange on an SP column, and then on a Heparin Sepharose column.

18. CP15 DNA Immunization

To determine whether modified IMX313 proteins could further improve the immunogenicity of the cryptosporidial antigen CP15, beyond the improvement obtained by using IMX313 itself, three plasmids designed to express Cp15, Cp15-IMX313 and IMX313T in *Escherichia coli* were used to prepare pcDNA3 vectors as DNA vaccines. The primers used to amplify the three genes from the T7 expression vectors for insertion into pcDNA3 downstream of the tPA signal peptide were:

IMX092:
(SEQ ID NO 84)
5' ggaaatccatgcccgattcagaagaGCGCGTGTTCTGATCAAA
GAGAAGC 3'
and IMX093:
(SEQ ID NO 85)
5' gccagtgtgatggatggcggtagttattgctcagcggtgg 3'.

The three PCR products were inserted separately into a pcDNA3 vector, which contained an N-terminal tPA signal peptide.

The three coding sequences were:

For Cp15:
(SEQ ID NO 86)
ATGGATGCAATGAAGAGAGGGCTCTGCTGTGTGCTGCTGCTGTGTG

GAGCAGTCTTCGTTTCGCCCAGCCAggaaatccatgcccgattcag aagaGCGCGTGTTCTGATCAAAGAGAAGCAGAATATGGGCAATCTC

AAAAGCTGTTGTTCCTTTGCTGACGAACACTCATTGACCAGCACTC

AACTGGTTGTAGGAAATGGCTCTGGTGCCTCTGAAACCGCAAGCAA

TCATCCACAGGAAGAAGTGAACGACATTAACACGTTTAACGTGAAA

CTGATCATGCAAGATCGCTCCAAACTGGATTGTGAGGTCGTCTTTG

ACAGTACCAGCATCAGTCTGAGTGGTGATGGCAAATGCCGCAATAT

CGCGTTAGACGAGATTCACCAGCTTCTGTATTCGAAGGAGGAATTA

AGCCGTGTGGAATCTTCAGCTGGGATTTCCGATAGCGATAACTGCG

TAGCCATTCACCTGAAAGAATCGGGTAACTGCATTCCGTTGTTCTT

CAACAATTCGCAGGATAAAGAACGCTTTGTGGCAACAGCGAATAAG

TTCAAACCGAACTTTAACCATCATCACCATCATCATTAA

For Cp15-IMX313:
(SEQ ID NO 87)
ATGGATGCAATGAAGAGAGGGCTCTGCTGTGTGCTGCTGCTGTGTG

GAGCAGTCTTCGTTTCGCCCAGCCAggaaatccatgcccgattcag aagaGCGCGTGTTCTGATCAAAGAGAAGCAGAATATGGGCAATCTC

AAAAGCTGTTGTTCCTTTGCTGACGAACACTCATTGACCAGCACTC

AACTGGTTGTAGGAAATGGCTCTGGTGCCTCTGAAACCGCAAGCAA

TCATCCACAGGAAGAAGTGAACGACATTAACACGTTTAACGTGAAA

CTGATCATGCAAGATCGCTCCAAACTGGATTGTGAGGTCGTCTTTG

ACAGTACCAGCATCAGTCTGAGTGGTGATGGCAAATGCCGCAATAT

CGCGTTAGACGAGATTCACCAGCTTCTGTATTCGAAGGAGGAATTA

AGCCGTGTGGAATCTTCAGCTGGGATTTCCGATAGCGATAACTGCG

TAGCCATTCACCTGAAAGAATCGGGTAACTGCATTCCGTTGTTCTT

CAACAATTCGCAGGATAAAGAACGCTTTGTGGCAACAGCGAATAAG

TTCAAACCGAACTTTAACGGATCCAAGAAGCAAGGTGATGCTGATG

TGTGCGGAGAGGTTGCTTATATTCAGAGCGTCGTCTCCGATTGCCA

CGTGCCTACAGCGGAACTGCGTACTCTGCTGGAAATACGAAAACTC

TTCCTGGAGATTCAAAAACTGAAGGTGCACCATCACCATTAA

And for CP15-IMX313T:
(SEQ ID NO 88)
ATGGATGCAATGAAGAGAGGGCTCTGCTGTGTGCTGCTGCTGTGTG GAGCAGTCTTCGTTTCGCCCAGCCAggaaatccatgcccgattcag aagaGCGCGTGTTCTGATCAAAGAGAAGCAGAATATGGGCAATCTC

AAAAGCTGTTGTTCCTTTGCTGACGAACACTCATTGACCAGCACTC

AACTGGTTGTAGGAAATGGCTCTGGTGCCTCTGAAACCGCAAGCAA

TCATCCACAGGAAGAAGTGAACGACATTAACACGTTTAACGTGAAA

CTGATCATGCAAGATCGCTCCAAACTGGATTGTGAGGTCGTCTTTG

ACAGTACCAGCATCAGTCTGAGTGGTGATGGCAAATGCCGCAATAT

CGCGTTAGACGAGATTCACCAGCTTCTGTATTCGAAGGAGGAATTA

AGCCGTGTGGAATCTTCAGCTGGGATTTCCGATAGCGATAACTGCG

TAGCCATTCACCTGAAAGAATCGGGTAACTGCATTCCGTTGTTCTT

CAACAATTCGCAGGATAAAGAACGCTTTGTGGCAACAGCGAATAAG

TTCAAACCGAACTTTAACGGATCCAAGAAGCAAGGTGATGCTGATG

TGTGCGGAGAGGTTGCTTATATTCAGAGCGTCGTCTCCGATTGCCA

CGTGCCTACAGCGGAACTGCGTACTCTGCTGGAAATACGAAAACTC

TTCCTGGAGATTCAAAAACTGAAGGTGGAACTGCAGTCTCCGCGTC

GCCGTCGCTCCTAA

The pcDNA3 vector with no insert was used as a control plasmid. These four plasmids were used to immunize four groups of 5-6 week old Balb/c female mice on days 0 & 14. Twenty-five micrograms of each plasmid was injected intramuscularly for each immunisation. On day 28, sera and spleens were collected for ELISAs and ELISPOTs. The Cp15-6His protein, purified from *Escherichia coli* was used as the ELISA antigen, and also to stimulate the splenic cells.

The results of the ELISAs and ELISPOTs are shown in Table 7, below.

| Immunogen | IgG Response Optical Density (405) | TH Pattern | Cellular Response INF ELISPOT ($\times 10^6$ Splenocytes) |
| --- | --- | --- | --- |
| Cp15 | 0.159 | Th1 = Th2 | 35 |
| Cp15-IMX313 | 0.358 | Th1 = Th2 | 117 |
| Cp15-IMX313T | 0.697 | Th1 = Th2 | 175 |
| Empty Vector | 0.087 | — | 12 |

These results show that IMX313 improves both antibody titers and Interferon γ responses to the Cp15 antigen, but these responses are further improved by the use of IMX313T instead of IMX313.

19. Immunisation with Self-Antigens and Modified IMX313 Protein Fusions: GnRH-IMX313T To further improve antibody responses induced by the self-antigen GnRH when fused to IMX313, the protein GnRH-IMX313T was prepared. The protein coding sequence was:

```
                                                         (SEQ ID NO 89)
ATGGAACATTGGAGCTATGGCCTGCGTCCGGGCGGATCCAAGAAGC

AAGGTGATGCTGATGTGTGCGGAGAGGTTGCTTATATTCAGAGCGT

CGTCTCCGATTGCCACGTGCCTACAGCGGAACTGCGTACTCTGCTG

GAAATACGAAAACTCTTCCTGGAGATTCAAAAACTGAAGGTGGAAC

TGCAGTCTCCGCGTCGCCGTCGCTCCTAATAA
``` and the protein sequence was:

```
                                                         (SEQ ID NO 90)
MEHWSYGLRPGGSKKQGDADVCGEVAYIQSVVSDCHVPTAELRTLL

EIRKLFLEIQKLKVELQSPRRRRS**
```

20. Synergy of Adjuvants with Modified IMX313 Proteins and Antigens

To determine whether the improved immunogenicity obtained by the use of modified IMX313 proteins could be further improved by the use of a classical adjuvant, and indeed by the use of two adjuvants, the following proteins were formulated: PAm, PAm-IMX313 and PAm-IMX313T (prepared as described in Example 6 above), as indicated in the column "Adjuvant" in the table below. The formulated proteins were then used to immunize seven groups of 5-6 week old Balb/c female mice on days 0 & 14. 5 mmoles of each protein was used per immunisation, with or without the adjuvant AddaVax, and with or without the TLR ligand poly I:C. In the seventh group, the TLR ligand poly I:C was first formulated with the protein PAm-IMX313T, and then with the adjuvant AddaVax.

On day 28, sera and spleens were collected for ELISAs and ELISPOTs. The PAm protein was used as the ELISA antigen, and also to stimulate the splenic cells.

The results are tabulated below (Table 8).

| Immunogen | Adjuvant | IgG Response Serial Dilution | Cellular Response INF ELISPOT (×10⁶ Splenocytes) |
|---|---|---|---|
| PAm | None | | 15 |
| PAm | Addavax | 100 | 28 |
| PAm-IMX313 | None | 400 | 63 |
| PAm-IMX313 | Addavax | 900 | 177 |
| PAm-IMX313T | None | 800 | 105 |
| PAm-IMX313T | Addavax | 6400 | 307 |
| PAm-IMX313T | Addavax + poly I:C | 6000 | 395 |

Clearly, there is an advantage to using an adjuvant with the modified IMX313 protein, and the immunogenicity can be further improved by using a second adjuvant, poly I:C.

REFERENCES

1) Odgren P R, Harvie L W Jr, Fey E G. 1996. Phylogenetic occurrence of coiled coil proteins: implications for tissue structure in metazoan via coiled coil tissue matrix. *Proteins* 24:467-484.
2) Rose A, Schraegle S J, Stahlberg E A, Meier I. 2005. Coiled-coil protein composition of 22 proteomes—differences and common themes in subcellular infrastructure and traffic control. *BMC Evol Biol.* 5:66.
3) Burkhard P, Stetefeld J, Strelkov S V. 2001. Coiled coils: a highly versatile protein folding motif. Trends Cell Biol. 11:82-88.
4) Tavano R, Capecchi B, Montanari P, Franzoso S, Marin O, Sztukowska M, Cecchini P, Segat D, Scarselli M, Aricò B, Papini E. 2011. Mapping of the *Neisseria meningitidis* NadA cell-binding site: relevance of predicted {alpha}-helices in the NH2-terminal and dimeric coiled-coil regions. *J Bacteriol.* 193:107-115.
5) El Tahir Y, & Skurnik M. 2001. YadA, the multifaceted *Yersinia* adhesin. *Int. J. Med. Microbiol.* 291:209-218.
6) Cotter S E, Surana N K, St. Geme III J W. 2005. Trimeric autotransporters: a distinct subfamily of autotransporter proteins. *Trends Microbiol.* 13:199-205.
7) Szczesny P, Linke D, Ursinus A, Bär K, Schwarz H, Riess T M, Kempf V A, Lupas A N, Martin J, Zeth K. 2008. Structure of the head of the *Bartonella* adhesin BadA. *PLoS Pathog.* 4:e1000119.
8) Serruto D, Spadafina T, Scarselli M, Bambini S, Comanducci M, Höhle S, Kilian M, Veiga E, Cossart P, Oggioni M R, Savino S, Ferlenghi I, Taddei A R, Rappuoli R, Pizza M, Masignani V, Aricò B. 2009. HadA is an atypical new multifunctional trimeric coiled-coil adhesin of *Haemophilus influenzae* biogroup *aegyptius*, which promotes entry into host cells. *Cell Microbiol.* 11:1044-1063.
9) Chen J, Wharton S A, Weissenhorn W, Calder L J, Hughson F M, Skehel J J, Wiley D C. 1995. A soluble domain of the membrane-anchoring chain of influenza virus hemagglutinin (HA2) folds in *Escherichia coli* into the low-pH-induced conformation. *Proc Natl Acad Sci USA.* 92:12205-12209.
10) Swanson K A, Settembre E C, Shaw C A, Dey A K, Rappuoli R, Mandl C W, Dormitzer P R, Carfi A. 2011. Structural basis for immunization with postfusion respiratory syncytial virus fusion F glycoprotein (RSV F) to elicit high neutralizing antibody titers. *Proc Natl Acad Sci USA.* 108:9619-9624.
11) Tan K, Liu J, Wang J, Shen S, Lu M.1997. Atomic structure of a thermostable subdomain of HIV-1 gp41. *Proc Natl Acad Sci USA.* 94:12303-12308.
12) Chen Y H, Christiansen A, Böck G, Dierich M P. 1995. HIV-2 transmembrane protein gp36 like HIV-1 gp41 binds to human lymphocytes and monocytes. *AIDS* 9:1193-1194.
13) Lee J E, Fusco M L, Hessell A J, Oswald W B, Burton D R, Saphire E O. 2008. Structure of the Ebola virus glycoprotein bound to an antibody from a human survivor. *Nature* 454:177-182.
14) Yuan P, Swanson K A, Leser G P, Paterson R G, Lamb R A, Jardetzky T S. 2011. Structure of the Newcastle disease virus hemagglutinin-neuraminidase (HN) ectodomain reveals a four-helix bundle stalk. *Proc Natl Acad Sci USA.* 108:14920-14925.
15) Chambers R S, Johnston S A. (2003) High-level generation of polyclonal antibodies by genetic immunization. *Nat Biotechnol.* 21:1088-1092.
16) Ogun S A, Dumon-Seignovert L, Marchand J B, Holder A A, Hill F. 2008. The oligomerization domain of C4-binding protein (C4bp) acts as an adjuvant, and the fusion protein comprised of the 19-kilodalton merozoite surface protein 1 fused with the murine C4bp domain protects mice against malaria. *Infect Immun.* 76:2817-3823.
17) Sassenfeld H M & Brewer S J. 1984. A polypeptide fusion designed for the purification of recombinant proteins. *Biotechnology.* 2:76-81.
18) Smith J C, Derbyshire R B, Cook E, Dunthorne L, Viney J, Brewer S J, Sassenfeld H M, Bell L D. 1984. Chemical synthesis and cloning of a poly(arginine)-coding gene fragment designed to aid polypeptide purification. *Gene.* 32:321-327.

19) Stempfer G, Höll-Neugebauer B, Rudolph R. 1996. Improved refolding of an immobilized fusion protein. *Nat Biotechnol.* 14:329-334.
20) Stempfer G, Höll-Neugebauer B, Kopetzki E, Rudolph R. 1996. A fusion protein designed for noncovalent immobilization: stability, enzymatic activity, and use in an enzyme reactor. *Nat Biotechnol.* 14:481-484.
21) Suzuki M. 1989. SPKK, a new nucleic acid-binding unit of protein found in histone. *EMBO J.* 8:797-804.
22) Fuchs S M & Raines R T. 2005. Polyarginine as a multifunctional fusion tag. *Protein Science* 14:1538-1544.
23) Blasius A L & Beutler B. 2010. Intracellular Toll-like Receptors. *Immunity* 32:305-315.
24) Akira S, Uematsu S, Takeuchi O. 2006. Pathogen recognition and innate immunity. *Cell* 124:783-801.
25) Ewald S E, Lee B L, Lau L, Wickliffe K E, Shi G P, Chapman H A, Barton G M. 2008. The ectodomain of Toll-like receptor 9 is cleaved to generate a functional receptor. *Nature* 456:658-662.
26) Mendlowski B, Field A K, Tytell A A, Hilleman M R. 1975. Safety assessment of poly I:C in NZB/NZW mice. *Proc Soc Exp Biol Med.* 148:476-483.
27) Kim H K, Cheng A G, Kim H Y, Missiakas D M, Schneewind O. 2010. Nontoxigenic protein A vaccine for methicillin-resistant *Staphylococcus aureus* infections in mice. *J Exp Med.* 207:1863-1870.
28) Spencer A J, Hill F, Honeycutt J D, Cottingham M G, Bregu M, Rollier C S, Furze J, Draper S J, Søgaard K C, Gilbert S C, Wyllie D H, 2012. Fusion of the *Mycobacterium tuberculosis* antigen 85A to an oligomerization domain enhances its immunogenicity in both mice and non-human primates. *PLoS One* 7:e33555.
29) Geiser M, Cèbe R; Drewello D, Schmitz R. 2001. Integration of PCR fragments at any specific site within cloning vectors without the use of restriction enzymes and DNA ligase. *Biotechniques* 31:88-92.
30) Ye Q, Krug R M, Tao Y J. (2006) The mechanism by which influenza A virus nucleoprotein forms oligomers and binds RNA. *Nature.* 444:1078-1082.
31) Tarus B, Bakowiez O, Chenavas S, Duchemin L, Estrozi L F, Bourdieu C, Lejal N, Bernard J, Moudjou M, Chevalier C, Delmas B, Ruigrok R W, Di Primo C, Slama-Schwok A. (2012) Oligomerization paths of the nucleoprotein of influenza A virus. *Biochimie.* 94:776-785.
32) Huber V C, McKeon R M, Brackin M N, Miller L, Keating R, Brown S A, Makarova N, Perez D R, MacDonald G H, McCullers J A. 2006 Distinct Contributions of Vaccine-Induced Immunoglobulin G1 (IgG1) and IgG2a Antibodies to Protective Immunity against Influenza. *CLINICAL AND VACCINE IMMUNOLOGY* 13: 981-990.
33) Krammer F, Pontiller J, Tauer C, Palmberger D, Maccani A, Baumann M, Grabherr R. (2010) Evaluation of the influenza A replicon for transient expression of recombinant proteins in mammalian cells. *PLoS One.* 5:e13265.
34) Yang Y, Ringler P, Müller S A, Burkhard P. (2012) Optimizing the refolding conditions of self-assembling polypeptide nanoparticles that serve as repetitive antigen display systems. *J Struct Biol.* 177:168-176.
35) Parry D A, Fraser R D, Squire J M. (2008) Fifty years of coiled-coils and alpha-helical bundles: a close relationship between sequence and structure. *J Struct Biol.* 163:258-269.
36) Bommakanti G, Citron M P, Hepler R W, Callahan C, Heidecker G J, Najar T A, Lu X, Joyce J G, Shiver J W, Casimiro D R, ter Meulen J, Liang X, Varadarajan R. (2010) Design of an HA2-based *Escherichia coli* expressed influenza immunogen that protects mice from pathogenic challenge. *Proc Natl Acad Sci USA.* 107: 13701-13706.
37) Bommakanti G, Lu X, Citron M P, Najar T A, Heidecker G J, ter Meulen J, Varadarajan R, Liang X. (2012) Design of *Escherichia coli*-expressed stalk domain immunogens of H1N1 hemagglutinin that protect mice from lethal challenge. *J Virol.* 86:13434-13444.
38) Birnbaum F, Nassal M. (1990) Hepatitis B virus nucleocapsid assembly: primary structure requirements in the core protein. *J Virol.* 64:3319-3330.
39) Mulcahy M E, Geoghegan J A, Monk I R, O'Keeffe K M, Walsh E J, Foster T J, McLoughlin R M. (2012) Nasal colonisation by *Staphylococcus aureus* depends upon clumping factor B binding to the squamous epithelial cell envelope protein loricrin. *PLoS Pathog.* 8(12): e1003092.
40) Shibagaki N, Okamoto T, Mitsui H, Inozume T, Kanzaki M, Shimada S. (2010) Novel immunotherapeutic approaches to skin cancer treatments using protein transduction technology. *J Dermatol Sci.* 61:153-161.
41) Mitsui H, Okamoto T, Kanzaki M, Inozume T, Shibagaki N, Shimada S. (2010) Intradermal injections of polyarginine-containing immunogenic antigens preferentially elicit Tc1 and Th1 activation and antitumour immunity. *Br J Dermatol.* 162:29-41
42) Mitsui H, Inozume T, Kitamura R, Shibagaki N, Shimada S. (2006) Polyarginine-mediated protein delivery to dendritic cells presents antigen more efficiently onto MHC class I and class II and elicits superior antitumor immunity. *J Invest Dermatol.* 126:1804-1812.
43) Shibagaki N, Udey M C. (2002) Dendritic cells transduced with protein antigens induce cytotoxic lymphocytes and elicit antitumor immunity. *J Immunol.* 168: 2393-2401.
44) O'Seaghdha M, van Schooten C J, Kerrigan S W, Emsley J, Silverman G J, Cox D, Lenting P J, Foster T J. (2006) *Staphylococcus aureus* protein A binding to von Willebrand factor A1 domain is mediated by conserved IgG binding regions. *FEBS J.* 273:4831-4841.
45) Arnau J, Lauritzen C, Petersen G E, Pedersen J. (2006) Current strategies for the use of affinity tags and tag removal for the purification of recombinant proteins. *Protein Expr Pur* 48:1-13.
46) Fromm J R, Hileman R E, Caldwell E E, Weiler J M, Linhardt R J. (1995) Differences in the interaction of heparin with arginine and lysine and the importance of these basic amino acids in the binding of heparin to acidic fibroblast growth factor. *Arch Biochem Biophys.* 323:279-287.
47) Chudasama S L, Espinasse B, Hwang F, Qi R, Joglekar M, Afonina G, Wiesner M R, Welsby I J, Ortel T L, Arepally G M. (2010) Heparin modifies the immunogenicity of positively charged proteins. *Blood.* 116:6046-6053.

Patent References

WO 2007/062819
WO 2007/100908
WO 2011/045612
WO 2008/122817

The invention claimed is:

1. A modified protein comprising (i) a protein having a coiled coil domain and (ii) at least one positively charged peptide directly linked or linked via a linker to the coiled coil domain, the positively charged peptide consisting of the sequence SEQ ID NO 1: ZXBBBBZ wherein:

Z is any amino acid or is absent;

X is any amino acid;

B is an arginine (R) or a lysine (K).

2. The modified protein of claim 1, wherein the positively charged peptide has a sequence selected from the group consisting of the peptides of sequences depicted in SEQ ID NO 2, SEQ ID NO 3, SEQ ID NO 4, SEQ ID NO 5, SEQ ID NO 36, SEQ ID NO 37 and SEQ ID NO 40.

3. The modified protein of claim 1, wherein the positively charged peptide is a fusion of two or more positively charged peptides of SEQ ID NO 1.

4. The modified protein of claim 3, wherein the fusion of two or more positively charged peptides of SEQ ID NO 1 has a sequence selected from the group consisting of the peptides of sequences SEQ ID NO 37 and SEQ ID NO 40.

5. The modified protein of claim 1, wherein the protein having a coiled coil domain has a function of carrier protein.

6. The modified protein of claim 5, wherein the coiled coil protein forms heptamers.

7. The modified protein of claim 6, wherein the coiled coil protein is SEQ ID NO: 6 or SEQ ID NO: 66.

8. The modified protein of claim 7 having the sequence as shown in SEQ ID NO 42 or in SEQ ID NO 7.

9. The modified protein of claim 1, wherein the protein having the coiled coil domain is an antigen.

10. The modified protein of claim 9, wherein the antigen is selected from the group consisting of the influenza hemagglutinin HA2 protein, the F glycoprotein of Respiratory Syncytial virus, the gp41 glycoproteins of HIV-1, the gp41 glycoproteins of HIV-2, the gp1 and gp2 glycoproteins of Ebolavirus, NadA from *Neisseria meningitidis*, YadA from *Yersinia enterocolitica*, UspA2 from *Moraxella catarrhalis*, BadA from *Bartonella henselae* and HadA from *Haemophilus influenza*.

11. A method of inducing an immune response in an individual comprising administering to the individual a modified protein according to claim 1.

12. The modified protein of claim 5, wherein the protein having the coiled coil domain is fused to an antigen.

13. An immunogenic composition comprising a modified protein according to claim 1 and an adjuvant.

14. An immunogenic composition comprising a modified protein according to claim 8 and an adjuvant.

15. The immunogenic composition of claim 14, wherein the adjuvant is nucleic acid ligands for intracellular TLRs.

16. The method of inducing an immune response of claim 11 wherein the protein having the coiled coil domain is an antigen.

* * * * *

SEQUENCE LISTING

<160> NUMBER OF SEQ ID NOS: 90

<210> SEQ ID NO 1
<211> LENGTH: 7
<212> TYPE: PRT
<213> ORGANISM: artificial
<220> FEATURE:
<223> OTHER INFORMATION: Positively charged peptide
<220> FEATURE:
<221> NAME/KEY: misc_feature
<222> LOCATION: (1)..(1)
<223> OTHER INFORMATION: X is any amino acid or is absent
<220> FEATURE:
<221> NAME/KEY: misc_feature
<222> LOCATION: (2)..(2)
<223> OTHER INFORMATION: X is any amino acid
<220> FEATURE:
<221> NAME/KEY: misc_feature
<222> LOCATION: (3)..(6)
<223> OTHER INFORMATION: X is an arginine (R) or a lysine (K)
<220> FEATURE:
<221> NAME/KEY: misc_feature
<222> LOCATION: (7)..(7)
<223> OTHER INFORMATION: X is any amino acid or is absent

<400> SEQUENCE: 1

Xaa Xaa Xaa Xaa Xaa Xaa Xaa
1               5

<210> SEQ ID NO 2
<211> LENGTH: 7
<212> TYPE: PRT
<213> ORGANISM: artificial
<220> FEATURE:
<223> OTHER INFORMATION: Positively charged peptide

<400> SEQUENCE: 2

Ser Pro Arg Arg Arg Arg Ser
1               5

<210> SEQ ID NO 3
<211> LENGTH: 5
<212> TYPE: PRT
<213> ORGANISM: artificial
<220> FEATURE:
<223> OTHER INFORMATION: Positively charged peptide

<400> SEQUENCE: 3

Gly Arg Arg Arg Arg
1               5

<210> SEQ ID NO 4
<211> LENGTH: 6
<212> TYPE: PRT
<213> ORGANISM: artificial
<220> FEATURE:
<223> OTHER INFORMATION: Positively charged peptide

<400> SEQUENCE: 4

Ser Pro Lys Lys Lys Lys
1               5

<210> SEQ ID NO 5
<211> LENGTH: 5
<212> TYPE: PRT
<213> ORGANISM: artificial
<220> FEATURE:
<223> OTHER INFORMATION: Positively charged peptide

<400> SEQUENCE: 5

Gly Lys Lys Lys Lys
1               5

<210> SEQ ID NO 6
<211> LENGTH: 55
<212> TYPE: PRT
<213> ORGANISM: Gallus gallus

<400> SEQUENCE: 6

Lys Lys Gln Gly Asp Ala Asp Val Cys Gly Glu Val Ala Tyr Ile Gln
1               5                   10                  15

Ser Val Val Ser Asp Cys His Val Pro Thr Ala Glu Leu Arg Thr Leu
            20                  25                  30

Leu Glu Ile Arg Lys Leu Phe Leu Glu Ile Gln Lys Leu Lys Val Glu
        35                  40                  45

Leu Gln Gly Leu Ser Lys Glu
    50                  55

<210> SEQ ID NO 7
<211> LENGTH: 57
<212> TYPE: PRT
<213> ORGANISM: artificial
<220> FEATURE:
<223> OTHER INFORMATION: Modified protein IMX313T

<400> SEQUENCE: 7

Lys Lys Gln Gly Asp Ala Asp Val Cys Gly Glu Val Ala Tyr Ile Gln
1               5                   10                  15

Ser Val Val Ser Asp Cys His Val Pro Thr Ala Glu Leu Arg Thr Leu
            20                  25                  30

Leu Glu Ile Arg Lys Leu Phe Leu Glu Ile Gln Lys Leu Lys Val Glu
        35                  40                  45

Leu Gln Ser Pro Arg Arg Arg Arg Ser
    50                  55

<210> SEQ ID NO 8
<211> LENGTH: 184
<212> TYPE: DNA
<213> ORGANISM: artificial
<220> FEATURE:
<223> OTHER INFORMATION: Oligonucleotide

<400> SEQUENCE: 8
catatgtcaa agaagcaagg tgatgctgat gtgtgcggag aggttgctta tattcagagc      60
gtcgtctccg attgccacgt gcctacagcg gaactgcgta ctctgctgga aatacgaaaa     120
ctcttcctgg agattcaaaa actgaaggtg gaattgcaag gactgagcaa ggagtaataa     180
gctt                                                                 184

<210> SEQ ID NO 9
<211> LENGTH: 57
<212> TYPE: PRT
<213> ORGANISM: artificial
<220> FEATURE:
<223> OTHER INFORMATION: IMX313 before removal of Met and Ser

<400> SEQUENCE: 9

Met Ser Lys Lys Gln Gly Asp Ala Asp Val Cys Gly Glu Val Ala Tyr
1               5                   10                  15

Ile Gln Ser Val Val Ser Asp Cys His Val Pro Thr Ala Glu Leu Arg
            20                  25                  30

Thr Leu Leu Glu Ile Arg Lys Leu Phe Leu Glu Ile Gln Lys Leu Lys
             35                  40                  45
Val Glu Leu Gln Gly Leu Ser Lys Glu
     50                  55

<210> SEQ ID NO 10
<211> LENGTH: 7
<212> TYPE: PRT
<213> ORGANISM: artificial
<220> FEATURE:
<223> OTHER INFORMATION: C-terminus sequence replaced in IMX313

<400> SEQUENCE: 10

Leu Gln Gly Leu Ser Lys Glu
1               5

<210> SEQ ID NO 11
<211> LENGTH: 9
<212> TYPE: PRT
<213> ORGANISM: artificial
<220> FEATURE:
<223> OTHER INFORMATION: Positively charged peptide

<400> SEQUENCE: 11

Leu Gln Ser Pro Arg Arg Arg Arg Ser
1               5

<210> SEQ ID NO 12
<211> LENGTH: 27
<212> TYPE: DNA
<213> ORGANISM: artificial
<220> FEATURE:
<223> OTHER INFORMATION: oligonucleotide

<400> SEQUENCE: 12
gtctccgcgt cgccgtcgct cctaata                                        27

<210> SEQ ID NO 13
<211> LENGTH: 35
<212> TYPE: DNA
<213> ORGANISM: artificial
<220> FEATURE:
<223> OTHER INFORMATION: oligonucleotide

<400> SEQUENCE: 13
agcttattag gagcgacggc gacgcggaga ctgca                               35

<210> SEQ ID NO 14
<211> LENGTH: 183
<212> TYPE: DNA
<213> ORGANISM: artificial
<220> FEATURE:
<223> OTHER INFORMATION: IMX313T

<400> SEQUENCE: 14
atgtcaaaga agcaaggtga tgctgatgtg tgcggagagg ttgcttatat tcagagcgtc    60
gtctccgatt gccacgtgcc tacagcggaa ctgcgtactc tgctggaaat acgaaaactc   120
ttcctggaga ttcaaaaact gaaggtggaa ctgcagtctc cgcgtcgccg tcgctcctaa   180
taa                                                                 183

<210> SEQ ID NO 15
<211> LENGTH: 45
<212> TYPE: DNA

<210> SEQ ID NO 15
<211> LENGTH: 45
<212> TYPE: DNA
<213> ORGANISM: artificial
<220> FEATURE:
<223> OTHER INFORMATION: Oligonucleotide

<400> SEQUENCE: 15
ctttaagaag gagatataca tatggctgat gcgcaacaaa ataac        45

<210> SEQ ID NO 16
<211> LENGTH: 51
<212> TYPE: DNA
<213> ORGANISM: artificial
<220> FEATURE:
<223> OTHER INFORMATION: Oligonucleotide

<400> SEQUENCE: 16
ccgcacacat cagcatcacc ttgctttttt ggtgcttgag catcatttag c        51

<210> SEQ ID NO 17
<211> LENGTH: 32
<212> TYPE: DNA
<213> ORGANISM: artificial
<220> FEATURE:
<223> OTHER INFORMATION: Oligonucleotide

<400> SEQUENCE: 17
cttcaacaaa gaaaaaaga acgccttcta tg        32

<210> SEQ ID NO 18
<211> LENGTH: 33
<212> TYPE: DNA
<213> ORGANISM: artificial
<220> FEATURE:
<223> OTHER INFORMATION: Oligonucleotide

<400> SEQUENCE: 18
gcgctttggc ttggagccgc ttttaagctt tgg        33

<210> SEQ ID NO 19
<211> LENGTH: 339
<212> TYPE: DNA
<213> ORGANISM: artificial
<220> FEATURE:
<223> OTHER INFORMATION: Mutated protein A

<400> SEQUENCE: 19
atggctgatg cgcaacaaaa taacttcaac aaaggaaaaa agaacgcctt ctatgaaatc        60
ttgaatatgc taacttaaa cgaagaacaa cgcaatggtt tcatccaaag cttaaaagcg        120
gctccaagcc aaagcgctaa ccttttagca gaagctaaaa agctaaatga tgctcaagca        180
ccaaaaaagc aaggtgatgc tgatgtgtgc ggagaggttg cttatattca gagcgtcgtc        240
tccgattgcc acgtgcctac agcggaactg cgtactctgc tggaaatacg aaaactcttc        300
ctggagattc aaaaactgaa ggtggaattg caataataa        339

<210> SEQ ID NO 20
<211> LENGTH: 111
<212> TYPE: PRT
<213> ORGANISM: artificial
<220> FEATURE:
<223> OTHER INFORMATION: Mutated protein A fused to IMX313

<400> SEQUENCE: 20

Met Ala Asp Ala Gln Gln Asn Asn Phe Asn Lys Gly Lys Lys Asn Ala
 1               5                  10                  15

```
Phe Tyr Glu Ile Leu Asn Met Pro Asn Leu Asn Glu Glu Gln Arg Asn
                 20                  25                  30

Gly Phe Ile Gln Ser Leu Lys Ala Ala Pro Ser Gln Ser Ala Asn Leu
         35                  40                  45

Leu Ala Glu Ala Lys Lys Leu Asn Asp Ala Gln Ala Pro Lys Lys Gln
 50                  55                  60

Gly Asp Ala Asp Val Cys Gly Glu Val Ala Tyr Ile Gln Ser Val Val
 65                  70                  75                  80

Ser Asp Cys His Val Pro Thr Ala Glu Leu Arg Thr Leu Leu Glu Ile
                 85                  90                  95

Arg Lys Leu Phe Leu Glu Ile Gln Lys Leu Lys Val Gly Leu Gln
            100                 105                 110

<210> SEQ ID NO 21
<211> LENGTH: 39
<212> TYPE: DNA
<213> ORGANISM: artificial
<220> FEATURE:
<223> OTHER INFORMATION: Oligonucleotide

<400> SEQUENCE: 21
gcagccggat caagcttatt attttggtgc ttgagcatc                    39

<210> SEQ ID NO 22
<211> LENGTH: 20
<212> TYPE: DNA
<213> ORGANISM: artificial
<220> FEATURE:
<223> OTHER INFORMATION: Oligonucleotide

<400> SEQUENCE: 22
taatacgact cactataggg                                         20

<210> SEQ ID NO 23
<211> LENGTH: 27
<212> TYPE: DNA
<213> ORGANISM: artificial
<220> FEATURE:
<223> OTHER INFORMATION: Oligonucleotide

<400> SEQUENCE: 23
gtctccgcgt cgccgtcgct cctaata                                 27

<210> SEQ ID NO 24
<211> LENGTH: 35
<212> TYPE: DNA
<213> ORGANISM: artificial
<220> FEATURE:
<223> OTHER INFORMATION: Oligonucleotide

<400> SEQUENCE: 24
agcttattag gagcgacggc gacgcggaga ctgca                        35

<210> SEQ ID NO 25
<211> LENGTH: 13
<212> TYPE: DNA
<213> ORGANISM: artificial
<220> FEATURE:
<223> OTHER INFORMATION: ssRNA40
<220> FEATURE:
<221> NAME/KEY: misc_binding
<222> LOCATION: (1)..(13)
<223> OTHER INFORMATION: Nucleotides are linked by phosphothioate

<400> SEQUENCE: 25
```

-continued

```
gcccgcgggg acc                                              13

<210> SEQ ID NO 26
<211> LENGTH: 20
<212> TYPE: DNA
<213> ORGANISM: artificial
<220> FEATURE:
<223> OTHER INFORMATION: ODN1826

<400> SEQUENCE: 26
tccatgacgt tcctgacgtt                                       20

<210> SEQ ID NO 27
<211> LENGTH: 14
<212> TYPE: PRT
<213> ORGANISM: artificial
<220> FEATURE:
<223> OTHER INFORMATION: IMX313 variant

<400> SEQUENCE: 27

Ile Arg Lys Leu Phe Leu Glu Ile Gln Lys Leu Lys Val Glu
1               5                   10

<210> SEQ ID NO 28
<211> LENGTH: 18
<212> TYPE: PRT
<213> ORGANISM: artificial
<220> FEATURE:
<223> OTHER INFORMATION: IMX313 variant

<400> SEQUENCE: 28

Thr Leu Leu Glu Ile Arg Lys Leu Phe Leu Glu Ile Gln Lys Leu Lys
1               5                   10                  15

Val Glu

<210> SEQ ID NO 29
<211> LENGTH: 47
<212> TYPE: DNA
<213> ORGANISM: artificial
<220> FEATURE:
<223> OTHER INFORMATION: Oligonucleotide

<400> SEQUENCE: 29
gaagcccgac ctgcaacgtg gatccatacg aaaactcttc ctggaga        47

<210> SEQ ID NO 30
<211> LENGTH: 43
<212> TYPE: DNA
<213> ORGANISM: artificial
<220> FEATURE:
<223> OTHER INFORMATION: Oligonucleotide

<400> SEQUENCE: 30
gaagcccgac ctgcaacgtg gatccactct gctggaaata cga            43

<210> SEQ ID NO 31
<211> LENGTH: 56
<212> TYPE: DNA
<213> ORGANISM: artificial
<220> FEATURE:
<223> OTHER INFORMATION: Oligonucleotide

<400> SEQUENCE: 31 agggcccctct agatgcatgc tcgagcggcc gcttattatt ccaccttcag tttttg    56
```

<210> SEQ ID NO 32
<211> LENGTH: 24
<212> TYPE: DNA
<213> ORGANISM: artificial
<220> FEATURE:
<223> OTHER INFORMATION: Oligonucleotide

<400> SEQUENCE: 32
cagaatagaa tgacacctac tcag                                           24

<210> SEQ ID NO 33
<211> LENGTH: 42
<212> TYPE: DNA
<213> ORGANISM: artificial
<220> FEATURE:
<223> OTHER INFORMATION: Oligonucleotide

<400> SEQUENCE: 33
gaagcccgac ctgcaacgtt aataagcggc cgctcgagca tg                       42

<210> SEQ ID NO 34
<211> LENGTH: 52
<212> TYPE: DNA
<213> ORGANISM: artificial
<220> FEATURE:
<223> OTHER INFORMATION: Oligonucleotide

<400> SEQUENCE: 34
gtgcctacag aggacgtgaa aatgctgctg gaaatacgaa aactcttcct gg            52

<210> SEQ ID NO 35
<211> LENGTH: 59
<212> TYPE: DNA
<213> ORGANISM: artificial
<220> FEATURE:
<223> OTHER INFORMATION: Oligonucleotide

<400> SEQUENCE: 35
agggccctct agatgcatgc tcgagcggcc gcttattagg agcgacggcg acgcggaga     59

<210> SEQ ID NO 36
<211> LENGTH: 7
<212> TYPE: PRT
<213> ORGANISM: artificial
<220> FEATURE:
<223> OTHER INFORMATION: Positively charged peptide

<400> SEQUENCE: 36

Gly Arg Arg Arg Arg Arg Ser
1               5

<210> SEQ ID NO 37
<211> LENGTH: 12
<212> TYPE: PRT
<213> ORGANISM: artificial
<220> FEATURE:
<223> OTHER INFORMATION: Positively charged peptide

<400> SEQUENCE: 37

Ser Pro Arg Arg Arg Arg Arg Arg Arg Arg Arg Ser
1               5                   10

<210> SEQ ID NO 38
<211> LENGTH: 6
<212> TYPE: PRT
<213> ORGANISM: artificial

```
<220> FEATURE:
<223> OTHER INFORMATION: Positively charged peptide

<400> SEQUENCE: 38

Ser Pro Arg Arg Arg Arg
1               5

<210> SEQ ID NO 39
<211> LENGTH: 6
<212> TYPE: PRT
<213> ORGANISM: artificial
<220> FEATURE:
<223> OTHER INFORMATION: Positively charged peptide

<400> SEQUENCE: 39

Arg Arg Arg Arg Arg Ser
1               5

<210> SEQ ID NO 40
<211> LENGTH: 12
<212> TYPE: PRT
<213> ORGANISM: artificial
<220> FEATURE:
<223> OTHER INFORMATION: Positively charged peptide

<400> SEQUENCE: 40

Gly Arg Arg Arg Arg Arg Arg Arg Arg Arg Ser
1               5                   10

<210> SEQ ID NO 41
<211> LENGTH: 6
<212> TYPE: PRT
<213> ORGANISM: artificial
<220> FEATURE:
<223> OTHER INFORMATION: Positively charged peptide

<400> SEQUENCE: 41

Gly Arg Arg Arg Arg Arg
1               5

<210> SEQ ID NO 42
<211> LENGTH: 55
<212> TYPE: PRT
<213> ORGANISM: artificial
<220> FEATURE:
<223> OTHER INFORMATION: IMX313P

<400> SEQUENCE: 42

Lys Lys Gln Gly Asp Ala Asp Val Cys Gly Glu Val Ala Tyr Ile Gln
1               5                   10                  15

Ser Val Val Ser Asp Cys His Val Pro Thr Ala Glu Leu Arg Thr Leu
            20                  25                  30

Leu Glu Ile Arg Lys Leu Phe Leu Glu Ile Gln Lys Leu Lys Val Glu
        35                  40                  45

Gly Arg Arg Arg Arg Arg Ser
    50                  55

<210> SEQ ID NO 43
<211> LENGTH: 46
<212> TYPE: DNA
<213> ORGANISM: artificial
<220> FEATURE:
<223> OTHER INFORMATION: oligonucleotide IMX205

<400> SEQUENCE: 43
```
ggagattcaa aaactgaagg tggaaggtcg ccgtcgccgt cgctcc    46

```
<210> SEQ ID NO 44
<211> LENGTH: 25
<212> TYPE: DNA
<213> ORGANISM: artificial
<220> FEATURE:
<223> OTHER INFORMATION: oligonucleotide IMX139

<400> SEQUENCE: 44
```
gggcgatcgg tgcgggcctc ttcgc    25

```
<210> SEQ ID NO 45
<211> LENGTH: 174
<212> TYPE: DNA
<213> ORGANISM: artificial
<220> FEATURE:
<223> OTHER INFORMATION: IMX313P

<400> SEQUENCE: 45
```
atgtcaaaga agcaaggtga tgctgatgtg tgcggagagg ttgcttatat tcagagcgtc    60
gtctccgatt gccacgtgcc tacagcggaa ctgcgtactc tgctggaaat acgaaaactc    120
ttcctggaga ttcaaaaact gaaggtggaa ggtcgccgtc gccgtcgctc ctaa    174

```
<210> SEQ ID NO 46
<211> LENGTH: 58
<212> TYPE: DNA
<213> ORGANISM: artificial
<220> FEATURE:
<223> OTHER INFORMATION: Primer IMX206

<400> SEQUENCE: 46
```
ggagattcaa aaactgaagg tggaaggtcg ccgtcgccgt taataagctt gatccggc    58

```
<210> SEQ ID NO 47
<211> LENGTH: 50
<212> TYPE: DNA
<213> ORGANISM: artificial
<220> FEATURE:
<223> OTHER INFORMATION: Primer IMX207

<400> SEQUENCE: 47
```
ctgaaggtgg aatctccgaa aaagaaaaag taataagctt gatccggctg    50

```
<210> SEQ ID NO 48
<211> LENGTH: 58
<212> TYPE: DNA
<213> ORGANISM: artificial
<220> FEATURE:
<223> OTHER INFORMATION: Primer IMX208

<400> SEQUENCE: 48
```
ggagattcaa aaactgaagg tggaaggtaa aaagaaaaag taataagctt gatccggc    58

```
<210> SEQ ID NO 49
<211> LENGTH: 25
<212> TYPE: DNA
<213> ORGANISM: artificial
<220> FEATURE:
<223> OTHER INFORMATION: Primer IMX139

<400> SEQUENCE: 49
```
gggcgatcgg tgcgggcctc ttcgc    25

```
<210> SEQ ID NO 50
<211> LENGTH: 55
<212> TYPE: PRT
<213> ORGANISM: Artificial
<220> FEATURE:
<223> OTHER INFORMATION: IMX427

<400> SEQUENCE: 50

Met Ser Lys Lys Gln Gly Asp Ala Asp Val Cys Gly Glu Val Ala Tyr
1               5                   10                  15

Ile Gln Ser Val Val Ser Asp Cys His Val Pro Thr Ala Glu Leu Arg
            20                  25                  30

Thr Leu Leu Glu Ile Arg Lys Leu Phe Leu Glu Ile Gln Lys Leu Lys
        35                  40                  45

Val Glu Gly Arg Arg Arg
    50                  55

<210> SEQ ID NO 51
<211> LENGTH: 56
<212> TYPE: PRT
<213> ORGANISM: Artificial
<220> FEATURE:
<223> OTHER INFORMATION: IMX428

<400> SEQUENCE: 51

Met Ser Lys Lys Gln Gly Asp Ala Asp Val Cys Gly Glu Val Ala Tyr
1               5                   10                  15

Ile Gln Ser Val Val Ser Asp Cys His Val Pro Thr Ala Glu Leu Arg
            20                  25                  30

Thr Leu Leu Glu Ile Arg Lys Leu Phe Leu Glu Ile Gln Lys Leu Lys
        35                  40                  45

Val Glu Ser Pro Lys Lys Lys Lys
    50                  55

<210> SEQ ID NO 52
<211> LENGTH: 55
<212> TYPE: PRT
<213> ORGANISM: Artificial
<220> FEATURE:
<223> OTHER INFORMATION: IMX429

<400> SEQUENCE: 52

Met Ser Lys Lys Gln Gly Asp Ala Asp Val Cys Gly Glu Val Ala Tyr
1               5                   10                  15

Ile Gln Ser Val Val Ser Asp Cys His Val Pro Thr Ala Glu Leu Arg
            20                  25                  30

Thr Leu Leu Glu Ile Arg Lys Leu Phe Leu Glu Ile Gln Lys Leu Lys
        35                  40                  45

Val Glu Gly Lys Lys Lys Lys
    50                  55

<210> SEQ ID NO 53
<211> LENGTH: 50
<212> TYPE: DNA
<213> ORGANISM: Artificial
<220> FEATURE:
<223> OTHER INFORMATION: Primer IMX1289

<400> SEQUENCE: 53
caatgcagag gagtacgaca atggatccaa gaagcaaggt gatgctgatg            50

<210> SEQ ID NO 54
```

```
<211> LENGTH: 47
<212> TYPE: DNA
<213> ORGANISM: Artificial
<220> FEATURE:
<223> OTHER INFORMATION: Primer IMX1290

<400> SEQUENCE: 54
gtagaaacaa gggtattttt ctttattact ccttgctcag tccttgc                    47

<210> SEQ ID NO 55
<211> LENGTH: 42
<212> TYPE: DNA
<213> ORGANISM: Artificial
<220> FEATURE:
<223> OTHER INFORMATION: Primer IMX1305

<400> SEQUENCE: 55
cactgagtga catcaaaatc atggatgcaa tgaagagagg gc                         42

<210> SEQ ID NO 56
<211> LENGTH: 53
<212> TYPE: DNA
<213> ORGANISM: Artificial
<220> FEATURE:
<223> OTHER INFORMATION: Primer IMX1306

<400> SEQUENCE: 56
cgtaagaccg tttggtgcct tggctagctc ttctgaatcg ggcatggatt tcc             53

<210> SEQ ID NO 57
<211> LENGTH: 29
<212> TYPE: DNA
<213> ORGANISM: Artificial
<220> FEATURE:
<223> OTHER INFORMATION: Primer IMX1287

<400> SEQUENCE: 57
ccattctgcc gcatttgcag atctaagag                                        29

<210> SEQ ID NO 58
<211> LENGTH: 29
<212> TYPE: DNA
<213> ORGANISM: Artificial
<220> FEATURE:
<223> OTHER INFORMATION: Primer IMX1288

<400> SEQUENCE: 58
caaaagggag atttgcctgt actgagaac                                        29

<210> SEQ ID NO 59
<211> LENGTH: 44
<212> TYPE: DNA
<213> ORGANISM: Artificial
<220> FEATURE:
<223> OTHER INFORMATION: Primer IMX051

<400> SEQUENCE: 59
gtagaaacaa gggtattttt ctttattagg agcgacggcg acgc                       44

<210> SEQ ID NO 60
<211> LENGTH: 385
<212> TYPE: DNA
<213> ORGANISM: Artificial
<220> FEATURE:
<223> OTHER INFORMATION: T7 expression vector

<400> SEQUENCE: 60
```

```
catatgcggg gttctcatca tcatcatcat catcatcatg gtagtggtta tgcagccgat    60
cagaaaagca cgcaaaatgc gattaacggc attaccaaca aagtcaattc tgtgatcgaa   120
aagatgaata tccagtttac tgctgtaggc aaagagttca acaaactgga gaaacgcatg   180
gaaaacctga caagaaagt ggatgatggg tttctggata tttggaccta taacgcggaa   240
```

(Note: actual line at 240 reads: `gaaaacctga caagaaagt ggatgatggg tttctggata tttggaccta taacgcggaa`)

```
ttacttgtgc tcttagaaaa cgaacggaca ttggacttcc atgattcgaa cgtcaagaac   300
ctgtatgaga aagtgaaaag ccagctgaag aacaatgcct caccacgtcg ccgtcgtcgc   360
cgtcgccgtc gcagttaata agctt                                         385
```

<210> SEQ ID NO 61
<211> LENGTH: 124
<212> TYPE: PRT
<213> ORGANISM: Artificial
<220> FEATURE:
<223> OTHER INFORMATION: T7 expression vector

<400> SEQUENCE: 61

```
Met Arg Gly Ser His His His His His His Gly Ser Gly Tyr
1               5                   10                  15

Ala Ala Asp Gln Lys Ser Thr Gln Asn Ala Ile Asn Gly Ile Thr Asn
            20                  25                  30

Lys Val Asn Ser Val Ile Glu Lys Met Asn Ile Gln Phe Thr Ala Val
        35                  40                  45

Gly Lys Glu Phe Asn Lys Leu Glu Lys Arg Met Glu Asn Leu Asn Lys
    50                  55                  60

Lys Val Asp Asp Gly Phe Leu Asp Ile Trp Thr Tyr Asn Ala Glu Leu
65                  70                  75                  80

Leu Val Leu Leu Glu Asn Glu Arg Thr Leu Asp Phe His Asp Ser Asn
                85                  90                  95

Val Lys Asn Leu Tyr Glu Lys Val Lys Ser Gln Leu Lys Asn Asn Ala
            100                 105                 110

Ser Pro Arg Arg Arg Arg Arg Arg Arg Arg Ser
        115                 120
```

<210> SEQ ID NO 62
<211> LENGTH: 45
<212> TYPE: DNA
<213> ORGANISM: Artificial
<220> FEATURE:
<223> OTHER INFORMATION: Primer IMX203

<400> SEQUENCE: 62

```
gttagcagcc ggatcaagct tattaggcat tgttcttcag ctggc                    45
```

<210> SEQ ID NO 63
<211> LENGTH: 343
<212> TYPE: DNA
<213> ORGANISM: Artificial
<220> FEATURE:
<223> OTHER INFORMATION: HA2 insert

<400> SEQUENCE: 63

```
catatgcggg gttctcatca tcatcatcat catggtagtg gttatgcagc cgatcagaaa    60
agcacgcaaa atgcgattaa cggcattacc aacaaagtca attctgtgat cgaaaagatg   120
aatatccagt ttactgctgt aggcaaagag ttcaacaaac tggagaaacg catggaaaac   180
ctgaacaaga aagtggatga tgggtttctg gatatttgga cctataacgc ggaattactt   240
```

```
gtgctcttag aaaacgaacg gacattggac ttccatgatt cgaacgtcaa gaacctgtat    300
gagaaagtga aaagccagct gaagaacaat gcctaataag ctt                      343
```

<210> SEQ ID NO 64
<211> LENGTH: 110
<212> TYPE: PRT
<213> ORGANISM: Artificial
<220> FEATURE:
<223> OTHER INFORMATION: HA2 insert

<400> SEQUENCE: 64

```
Met Arg Gly Ser His His His His His Gly Ser Gly Tyr Ala Ala
1               5                   10                  15

Asp Gln Lys Ser Thr Gln Asn Ala Ile Asn Gly Ile Thr Asn Lys Val
            20                  25                  30

Asn Ser Val Ile Glu Lys Met Asn Ile Gln Phe Thr Ala Val Gly Lys
        35                  40                  45

Glu Phe Asn Lys Leu Glu Lys Arg Met Glu Asn Leu Asn Lys Lys Val
50                  55                  60

Asp Asp Gly Phe Leu Asp Ile Trp Thr Tyr Asn Ala Glu Leu Leu Val
65                  70                  75                  80

Leu Leu Glu Asn Glu Arg Thr Leu Asp Phe His Asp Ser Asn Val Lys
                85                  90                  95

Asn Leu Tyr Glu Lys Val Lys Ser Gln Leu Lys Asn Asn Ala
            100                 105                 110
```

<210> SEQ ID NO 65
<211> LENGTH: 46
<212> TYPE: DNA
<213> ORGANISM: Artificial
<220> FEATURE:
<223> OTHER INFORMATION: Primer IMX212

<400> SEQUENCE: 65

```
ggagcgacgg cgacgcggag actggagctg tagtagttca acctcc                    46
```

<210> SEQ ID NO 66
<211> LENGTH: 54
<212> TYPE: PRT
<213> ORGANISM: Artificial
<220> FEATURE:
<223> OTHER INFORMATION: IMX108

<400> SEQUENCE: 66

```
Glu Ala Ser Glu Asp Leu Lys Pro Ala Leu Thr Gly Asn Lys Thr Met
1               5                   10                  15

Gln Tyr Val Pro Asn Ser His Asp Val Lys Met Ala Leu Glu Ile Tyr
            20                  25                  30

Lys Leu Thr Leu Glu Val Glu Leu Leu Gln Leu Gln Ile Gln Lys Glu
        35                  40                  45

Lys His Thr Glu Ala His
    50
```

<210> SEQ ID NO 67
<211> LENGTH: 51
<212> TYPE: PRT
<213> ORGANISM: Artificial
<220> FEATURE:
<223> OTHER INFORMATION: IMX108T

<400> SEQUENCE: 67

```
Glu Ala Ser Glu Asp Leu Lys Pro Ala Leu Thr Gly Asn Lys Thr Met
1               5                   10                  15

Gln Tyr Val Pro Asn Ser His Asp Val Lys Met Ala Leu Glu Ile Tyr
            20                  25                  30

Lys Leu Thr Leu Glu Val Glu Leu Leu Gln Leu Gln Ser Pro Arg Arg
        35                  40                  45

Arg Arg Ser
    50

<210> SEQ ID NO 68
<211> LENGTH: 59
<212> TYPE: DNA
<213> ORGANISM: Artificial
<220> FEATURE:
<223> OTHER INFORMATION: IMX056

<400> SEQUENCE: 68
gtttaacttt aagaaggaga tatacatatg gcagattctg atattaatat taaaaccgg      59

<210> SEQ ID NO 69
<211> LENGTH: 59
<212> TYPE: DNA
<213> ORGANISM: Artificial
<220> FEATURE:
<223> OTHER INFORMATION: IMX057

<400> SEQUENCE: 69
gttagcagcc ggatcaagct tattaatcga ttttatatct ttctgaagaa cgatctgtc      59

<210> SEQ ID NO 70
<211> LENGTH: 45
<212> TYPE: DNA
<213> ORGANISM: Artificial
<220> FEATURE:
<223> OTHER INFORMATION: Primer IMX110

<400> SEQUENCE: 70
agaacgaaag gtaccattgc tggatccaag aagcaaggtg atgct                     45

<210> SEQ ID NO 71
<211> LENGTH: 121
<212> TYPE: PRT
<213> ORGANISM: Artificial
<220> FEATURE:
<223> OTHER INFORMATION: Hla63-IMX313T fusion protein

<400> SEQUENCE: 71

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Ser
    50                  55                  60

Lys Lys Gln Gly Asp Ala Asp Val Cys Gly Glu Val Ala Tyr Ile Gln
65                  70                  75                  80

Ser Val Val Ser Asp Cys His Val Pro Thr Ala Glu Leu Arg Thr Leu
                85                  90                  95

Leu Glu Ile Arg Lys Leu Phe Leu Glu Ile Gln Lys Leu Lys Val Glu
            100                 105                 110
```

Leu Gln Ser Pro Arg Arg Arg Arg Ser
        115                 120

<210> SEQ ID NO 72
<211> LENGTH: 369
<212> TYPE: DNA
<213> ORGANISM: Artificial
<220> FEATURE:
<223> OTHER INFORMATION: Hla63-IMX313T fusion protein

<400> SEQUENCE: 72

```
atggcagatt ctgatattaa tattaaaacc ggtactacag atattggaag caatactaca    60
gtaaaaacag gtgatttagt cacttatgat aagaaaatg gcatgcacaa aaaagtattt    120
tatagtttta tcgatgataa aaatcataat aaaaaactgc tagttattag aacgaaaggt   180
accattgctg atccaagaa gcaaggtgat gctgatgtgt gcggagaggt tgcttatatt    240
cagagcgtcg tctccgattg ccacgtgcct acagcggaac tgcgtactct gctggaaata   300
cgaaaactct tcctggagat tcaaaaactg aaggtggaac tgcagtctcc gcgtcgccgt   360
cgctcctaa                                                          369
```

<210> SEQ ID NO 73
<211> LENGTH: 913
<212> TYPE: DNA
<213> ORGANISM: Artificial
<220> FEATURE:
<223> OTHER INFORMATION: Synthetic gene encoding the 5 homologouos
        domains of SpA

<400> SEQUENCE: 73

```
catatggcgc aacacgatga agctcaagcg aatgcattct accaggttct gaacatgccg    60
aatttgaatg cggaccaacg taatggcttt attcaatccc tgaaggacgc accgtcccaa   120
agcgcaaacg ttctgggtga agcgcaaaaa ctgaatgata gccaggcccc gaaagccgat   180
gcccagcaga acaagttcaa taaggatcag gcctctgcgt tctatgagat tttgaatatg   240
ccgaacttga atgaggagca acgcaacggc tttatccaaa gcctgaaaga tgcaccaagc   300
caaagcacga acgtcctggg tgaggcaaag aaactgaacg agagccaggc gccgaaagcg   360
gacaacaatt tcaataaaga gcaagcgaac gccttttacg aaattctgaa tatgcctaac   420
ctgaacgaag aacaacgtaa cggcttcatc cagagcttga aggacgcgcc gtcgcaaagc   480
gcgaatctgc tggccgaggc gaaaaagctg aatgagagcc aagcgccgaa ggcggacaat   540
aagtttaaca agaacaggc gaacgcattc tatgaaatcc tgcatctgcc gaatctgaat   600
gaagaacagc gcaatggttt tatccagagc ctgaaggatg cgccaagcca gagcgcaaac   660
ctgttggctg aggccaagaa gctgaacgat gcgcaggctc cgaaagctga caacaaattc   720
aacaaagagc aggccaacgc tttttacgag attctgcact tgccgaacct gaccgaagaa   780
cagcgtaatg gtttcatcca gtctctgaaa gacgcaccga gcgtgagcaa agagattctg   840
gcagaggcga agaagttgaa cgacgcgcag gcaccgaaag atcccatca ccaccaccat    900
cactaataag ctt                                                     913
```

<210> SEQ ID NO 74
<211> LENGTH: 300
<212> TYPE: PRT
<213> ORGANISM: Artificial
<220> FEATURE:
<223> OTHER INFORMATION: Synthetic protein comprising the 5 homologouos
        domains of SpA

<400> SEQUENCE: 74

```
Met Ala Gln His Asp Glu Ala Gln Ala Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Asp Ala Pro Ser Gln Ser Ala Asn Val Leu Gly Glu Ala Gln
        35                  40                  45

Lys Leu Asn Asp Ser Gln Ala Pro Lys Ala Asp Ala Gln Gln Asn Lys
    50                  55                  60

Phe Asn Lys Asp Gln Ala Ser Ala Phe Tyr Glu Ile Leu Asn Met Pro
65                  70                  75                  80

Asn Leu Asn Glu Glu Gln Arg Asn Gly Phe Ile Gln Ser Leu Lys Asp
                85                  90                  95

Ala Pro Ser Gln Ser Thr Asn Val Leu Gly Glu Ala Lys Lys Leu Asn
            100                 105                 110

Glu Ser Gln Ala Pro Lys Ala Asp Asn Asn Phe Asn Lys Glu Gln Ala
        115                 120                 125

Asn Ala Phe Tyr Glu Ile Leu Asn Met Pro Asn Leu Asn Glu Glu Gln
    130                 135                 140

Arg Asn Gly Phe Ile Gln Ser Leu Lys Asp Ala Pro Ser Gln Ser Ala
145                 150                 155                 160

Asn Leu Leu Ala Glu Ala Lys Lys Leu Asn Glu Ser Gln Ala Pro Lys
                165                 170                 175

Ala Asp Asn Lys Phe Asn Lys Glu Gln Ala Asn Ala Phe Tyr Glu Ile
            180                 185                 190

Leu His Leu Pro Asn Leu Asn Glu Glu Gln Arg Asn Gly Phe Ile Gln
        195                 200                 205

Ser Leu Lys Asp Ala Pro Ser Gln Ser Ala Asn Leu Leu Ala Glu Ala
    210                 215                 220

Lys Lys Leu Asn Asp Ala Gln Ala Pro Lys Ala Asp Asn Lys Phe Asn
225                 230                 235                 240

Lys Glu Gln Ala Asn Ala Phe Tyr Glu Ile Leu His Leu Pro Asn Leu
                245                 250                 255

Thr Glu Glu Gln Arg Asn Gly Phe Ile Gln Ser Leu Lys Asp Ala Pro
            260                 265                 270

Ser Val Ser Lys Glu Ile Leu Ala Glu Ala Lys Lys Leu Asn Asp Ala
        275                 280                 285

Gln Ala Pro Lys Gly Ser His His His His His
    290                 295                 300
```

<210> SEQ ID NO 75
<211> LENGTH: 56
<212> TYPE: DNA
<213> ORGANISM: Artificial
<220> FEATURE:
<223> OTHER INFORMATION: Primer IMX239

<400> SEQUENCE: 75
catcatcatc atcatcacgg tgctgaaccg gtagtaaatg ctgctgatgc taaagg   56

<210> SEQ ID NO 76
<211> LENGTH: 58
<212> TYPE: DNA
<213> ORGANISM: Artificial
<220> FEATURE:
<223> OTHER INFORMATION: Primer IMX240

<400> SEQUENCE: 76 cccccaagggg ttatgctagt taatttactg ctgaatcacc atcagcactt ccaccacc    58

<210> SEQ ID NO 77
<211> LENGTH: 1068
<212> TYPE: DNA
<213> ORGANISM: Artificial
<220> FEATURE:
<223> OTHER INFORMATION: N2N3 fragment

<400> SEQUENCE: 77

```
atgcggggtt ctcatcatca tcatcatcat catcatggtg ctgaaccggt agtaaatgct     60
gctgatgcta aaggtacaaa tgtaaatgat aaagttacgg caagtaattt caagttagaa    120
aagactacat tgaccctaa tcaaagtggt aacacattta tggcggcaaa ttttacagtg    180
acagataaag tgaaatcagg ggattatttt acagcgaagt taccagatag tttaactggt    240
aatggagacg tggattattc taattcaaat aatacgatgc caattgcaga cattaaaagt    300
acgaatggcg atgttgtagc taaagcaaca tatgatatct tgactaagac gtatacatt    360
gtctttacag attatgtaaa aataaagaa aatattaacg acaattttc attacccttta    420
tttacagacc gagcaaaggc acctaaatca ggaacatatg atgcgaatat taatattgcg    480
gatgaaatgt ttaataataa aattacttat aactatagtt cgccaattgc aggaattgat    540
aaaccaaatg cgcgaacat ttcttctcaa attattggtg tagatacagc ttcaggtcaa    600
aacacataca agcaaacagt atttgttaac cctaagcaac gagttttagg taatacgtgg    660
gtgtatatta aaggctacca agataaaatc gaagaaagta gcggtaaagt aagtgctaca    720
gatacaaaac tgagaatttt tgaagtgaat gatacatcta aattatcaga tagctactat    780
gcagatccaa atgactctaa ccttaaagaa gtaacgaccc aatttaaaaa tagaatctat    840
tatgagcatc caaatgtagc tagtattaaa tttggtgata ttactaaaac atatgtagta    900
ttagtagaag gcattacga caatacaggt aagaacttaa aaactcaggt tattcaagaa    960
aatgttgatc ctgtaacaaa tagagactac agtatttcg gttggaataa tgagaatgtt   1020
gtacgttatg gtgtggaag tgctgatggt gattcagcag taaattaa                1068
```

<210> SEQ ID NO 78
<211> LENGTH: 355
<212> TYPE: PRT
<213> ORGANISM: Artificial
<220> FEATURE:
<223> OTHER INFORMATION: N2N3 fragment

<400> SEQUENCE: 78

```
Met Arg Gly Ser His His His His His His Gly Ala Glu Pro
1               5                   10                  15

Val Val Asn Ala Ala Asp Ala Lys Gly Thr Asn Val Asn Asp Lys Val
            20                  25                  30

Thr Ala Ser Asn Phe Lys Leu Glu Lys Thr Thr Phe Asp Pro Asn Gln
        35                  40                  45

Ser Gly Asn Thr Phe Met Ala Ala Asn Phe Thr Val Thr Asp Lys Val
    50                  55                  60

Lys Ser Gly Asp Tyr Phe Thr Ala Lys Leu Pro Asp Ser Leu Thr Gly
65                  70                  75                  80

Asn Gly Asp Val Asp Tyr Ser Asn Ser Asn Asn Thr Met Pro Ile Ala
                85                  90                  95

Asp Ile Lys Ser Thr Asn Gly Asp Val Val Ala Lys Ala Thr Tyr Asp
```

```
            100                 105                 110
Ile Leu Thr Lys Thr Tyr Thr Phe Val Phe Thr Asp Tyr Val Asn Asn
        115                 120                 125

Lys Glu Asn Ile Asn Gly Gln Phe Ser Leu Pro Leu Phe Thr Asp Arg
    130                 135                 140

Ala Lys Ala Pro Lys Ser Gly Thr Tyr Asp Ala Asn Ile Asn Ile Ala
145                 150                 155                 160

Asp Glu Met Phe Asn Asn Lys Ile Thr Tyr Asn Tyr Ser Ser Pro Ile
                165                 170                 175

Ala Gly Ile Asp Lys Pro Asn Gly Ala Asn Ile Ser Ser Gln Ile Ile
            180                 185                 190

Gly Val Asp Thr Ala Ser Gly Gln Asn Thr Tyr Lys Gln Thr Val Phe
        195                 200                 205

Val Asn Pro Lys Gln Arg Val Leu Gly Asn Thr Trp Val Tyr Ile Lys
    210                 215                 220

Gly Tyr Gln Asp Lys Ile Glu Glu Ser Ser Gly Lys Val Ser Ala Thr
225                 230                 235                 240

Asp Thr Lys Leu Arg Ile Phe Glu Val Asn Asp Thr Ser Lys Leu Ser
                245                 250                 255

Asp Ser Tyr Tyr Ala Asp Pro Asn Asp Ser Asn Leu Lys Glu Val Thr
            260                 265                 270

Asp Gln Phe Lys Asn Arg Ile Tyr Tyr Glu His Pro Asn Val Ala Ser
        275                 280                 285

Ile Lys Phe Gly Asp Ile Thr Lys Thr Tyr Val Val Leu Val Glu Gly
    290                 295                 300

His Tyr Asp Asn Thr Gly Lys Asn Leu Lys Thr Gln Val Ile Gln Glu
305                 310                 315                 320

Asn Val Asp Pro Val Thr Asn Arg Asp Tyr Ser Ile Phe Gly Trp Asn
                325                 330                 335

Asn Glu Asn Val Val Arg Tyr Gly Gly Gly Ser Ala Asp Gly Asp Ser
            340                 345                 350

Ala Val Asn
        355

<210> SEQ ID NO 79
<211> LENGTH: 52
<212> TYPE: DNA
<213> ORGANISM: Artificial
<220> FEATURE:
<223> OTHER INFORMATION: Primer IMX248

<400> SEQUENCE: 79
gctgatggtg attcagcagt aaatggatcc aagaagcaag gtgatgctga tg         52

<210> SEQ ID NO 80
<211> LENGTH: 50
<212> TYPE: DNA
<213> ORGANISM: Artificial
<220> FEATURE:
<223> OTHER INFORMATION: Primer IMX005

<400> SEQUENCE: 80
gtttaacttt aagaaggaga tatacatatg caagctaaac ctcaaattcc           50

<210> SEQ ID NO 81
<211> LENGTH: 45
<212> TYPE: DNA
<213> ORGANISM: Artificial
```

<220> FEATURE:
<223> OTHER INFORMATION: Primer IMX1275

<400> SEQUENCE: 81
gttagcagcc ggatcaagct tattatttga cttctgtagc tacaa                45

<210> SEQ ID NO 82
<211> LENGTH: 52
<212> TYPE: DNA
<213> ORGANISM: Artificial
<220> FEATURE:
<223> OTHER INFORMATION: Primer IMX215

<400> SEQUENCE: 82
gataaacaat taacattaat tacttctgat gattacaatg aaaagacagg cg         52

<210> SEQ ID NO 83
<211> LENGTH: 42
<212> TYPE: DNA
<213> ORGANISM: Artificial
<220> FEATURE:
<223> OTHER INFORMATION: Primer IMX006

<400> SEQUENCE: 83
ttgtagctac agaagtcaaa aagaagcaag gtgatgctga tg                    42

<210> SEQ ID NO 84
<211> LENGTH: 50
<212> TYPE: DNA
<213> ORGANISM: Artificial
<220> FEATURE:
<223> OTHER INFORMATION: Primer IMX092

<400> SEQUENCE: 84
ggaaatccat gcccgattca gaagagcgcg tgttctgatc aaagagaagc             50

<210> SEQ ID NO 85
<211> LENGTH: 40
<212> TYPE: DNA
<213> ORGANISM: Artificial
<220> FEATURE:
<223> OTHER INFORMATION: Primer IMX093

<400> SEQUENCE: 85
gccagtgtga tggatggcgg tagttattgc tcagcggtgg                       40

<210> SEQ ID NO 86
<211> LENGTH: 591
<212> TYPE: DNA
<213> ORGANISM: Artificial
<220> FEATURE:
<223> OTHER INFORMATION: Cp15

<400> SEQUENCE: 86
atggatgcaa tgaagagagg gctctgctgt gtgctgctgc tgtgtggagc agtcttcgtt    60
tcgcccagcc aggaaatcca tgcccgattc agaagagcgc gtgttctgat caaagagaag   120
cagaatatgg gcaatctcaa aagctgttgt tcctttgctg acgaacactc attgaccagc   180
actcaactgg ttgtaggaaa tggctctggt gcctctgaaa ccgcaagcaa tcatccacag   240
gaagaagtga acgacattaa cacgtttaac gtgaaactga tcatgcaaga tcgctccaaa   300
ctggattgtg aggtcgtctt tgacagtacc agcatcagtc tgagtggtga tgcaaatgc    360 cgcaatatcg cgttagacga gattcaccag cttctgtatt cgaaggagga attaagccgt   420

```
gtggaatctt cagctgggat ttccgatagc gataactgcg tagccattca cctgaaagaa    480
tcgggtaact gcattccgtt gttcttcaac aattcgcagg ataaagaacg ctttgtggca    540
acagcgaata agttcaaacc gaactttaac catcatcacc atcatcatta a             591
```

<210> SEQ ID NO 87
<211> LENGTH: 732
<212> TYPE: DNA
<213> ORGANISM: Artificial
<220> FEATURE:
<223> OTHER INFORMATION: Cp15-IMX313

<400> SEQUENCE: 87

```
atggatgcaa tgaagagagg gctctgctgt gtgctgctgc tgtgtggagc agtcttcgtt     60
tcgcccagcc aggaaatcca tgcccgattc agaagagcgc gtgttctgat caaagagaag    120
cagaatatgg gcaatctcaa aagctgttgt tcctttgctg acgaacactc attgaccagc    180
actcaactgg ttgtaggaaa tggctctggt gcctctgaaa ccgcaagcaa tcatccacag    240
gaagaagtga acgacattaa cacgtttaac gtgaaactga tcatgcaaga tcgctccaaa    300
ctggattgtg aggtcgtctt tgacagtacc agcatcagtc tgagtggtga tggcaaatgc    360
cgcaatatcg cgttagacga gattcaccag cttctgtatt cgaaggagga attaagccgt    420
gtggaatctt cagctgggat ttccgatagc gataactgcg tagccattca cctgaaagaa    480
tcgggtaact gcattccgtt gttcttcaac aattcgcagg ataaagaacg ctttgtggca    540
acagcgaata agttcaaacc gaactttaac ggatccaaga agcaaggtga tgctgatgtg    600
tgcggagagg ttgcttatat tcagagcgtc gtctccgatt gccacgtgcc tacagcggaa    660
ctgcgtactc tgctggaaat acgaaaactc ttcctggaga ttcaaaaact gaaggtgcac    720
catcaccatt aa                                                       732
```

<210> SEQ ID NO 88
<211> LENGTH: 750
<212> TYPE: DNA
<213> ORGANISM: Artificial
<220> FEATURE:
<223> OTHER INFORMATION: CP15-IMX313T

<400> SEQUENCE: 88

```
atggatgcaa tgaagagagg gctctgctgt gtgctgctgc tgtgtggagc agtcttcgtt     60
tcgcccagcc aggaaatcca tgcccgattc agaagagcgc gtgttctgat caaagagaag    120
cagaatatgg gcaatctcaa aagctgttgt tcctttgctg acgaacactc attgaccagc    180
actcaactgg ttgtaggaaa tggctctggt gcctctgaaa ccgcaagcaa tcatccacag    240
gaagaagtga acgacattaa cacgtttaac gtgaaactga tcatgcaaga tcgctccaaa    300
ctggattgtg aggtcgtctt tgacagtacc agcatcagtc tgagtggtga tggcaaatgc    360
cgcaatatcg cgttagacga gattcaccag cttctgtatt cgaaggagga attaagccgt    420
gtggaatctt cagctgggat ttccgatagc gataactgcg tagccattca cctgaaagaa    480
tcgggtaact gcattccgtt gttcttcaac aattcgcagg ataaagaacg ctttgtggca    540
acagcgaata agttcaaacc gaactttaac ggatccaaga agcaaggtga tgctgatgtg    600
tgcggagagg ttgcttatat tcagagcgtc gtctccgatt gccacgtgcc tacagcggaa    660
ctgcgtactc tgctggaaat acgaaaactc ttcctggaga ttcaaaaact gaaggtggaa    720
ctgcagtctc cgcgtcgccg tcgctcctaa                                    750
```

-continued

```
<210> SEQ ID NO 89
<211> LENGTH: 216
<212> TYPE: DNA
<213> ORGANISM: Artificial
<220> FEATURE:
<223> OTHER INFORMATION: GnRH-IMX313T

<400> SEQUENCE: 89
atggaacatt ggagctatgg cctgcgtccg ggcggatcca agaagcaagg tgatgctgat      60
gtgtgcggag aggttgctta tattcagagc gtcgtctccg attgccacgt gcctacagcg     120
gaactgcgta ctctgctgga aatacgaaaa ctcttcctgg agattcaaaa actgaaggtg     180
gaactgcagt ctccgcgtcg ccgtcgctcc taataa                               216

<210> SEQ ID NO 90
<211> LENGTH: 70
<212> TYPE: PRT
<213> ORGANISM: Artificial
<220> FEATURE:
<223> OTHER INFORMATION: GnRH-IMX313T

<400> SEQUENCE: 90

Met Glu His Trp Ser Tyr Gly Leu Arg Pro Gly Gly Ser Lys Lys Gln
1               5                   10                  15

Gly Asp Ala Asp Val Cys Gly Glu Val Ala Tyr Ile Gln Ser Val Val
            20                  25                  30

Ser Asp Cys His Val Pro Thr Ala Glu Leu Arg Thr Leu Leu Glu Ile
        35                  40                  45

Arg Lys Leu Phe Leu Glu Ile Gln Lys Leu Lys Val Glu Leu Gln Ser
    50                  55                  60

Pro Arg Arg Arg Arg Ser
65                  70
```